(12) United States Patent
Hirano et al.

(10) Patent No.: US 6,303,797 B1
(45) Date of Patent: Oct. 16, 2001

(54) SESTERTERPENE DERIVATIVES EXHIBITING ANTIFUNGAL ACTIVITIES

(75) Inventors: Atsushi Hirano; Eiji Sugiyama; Hisao Kondo; Hiroyuki Suda, all of Tsukuba; Hidenori Ogawa; Katsuhisa Kojiri, both of Tokyo, all of (JP)

(73) Assignee: Banyu Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/744,765

(22) PCT Filed: Aug. 4, 1999

(86) PCT No.: PCT/JP99/04198

§ 371 Date: Jan. 30, 2001

§ 102(e) Date: Jan. 30, 2001

(87) PCT Pub. No.: WO00/08010

PCT Pub. Date: Feb. 17, 2000

(30) Foreign Application Priority Data

Aug. 7, 1998 (JP) .................................................. 10-236415

(51) Int. Cl.$^7$ ...................... C07D 307/93; C07D 311/78; C07D 311/94; A61K 31/366
(52) U.S. Cl. ............................................ 549/276; 514/453
(58) Field of Search ............................... 549/276; 514/453

(56) References Cited

U.S. PATENT DOCUMENTS

| | | | |
|---|---|---|---|
| 5,233,062 | 8/1993 | Horn et al. | 554/109 |
| 5,928,910 | 7/1999 | Kushida et al. | 435/125 |

FOREIGN PATENT DOCUMENTS

WO 97/19186   5/1997   (WO) .

OTHER PUBLICATIONS

Iwata Fungi, Fungous Diseases and Chemotherapy pp 123–135 and 156–157 (1994).
Denning et al European J. of Clinical Microbiology & Infectious Disease vol. 16, No. 4, pp 261–280 1997.
Wang et al Helv. Chim. Acta vol. 81 (1998) pp. 2031–2042 "Conformation and Relative Configuration of a Very Potent Glycosylphosphatidylinositol–Anchoring Inhibitor etc".
Sutterlin et al The EMBO Jj vol. 16, No. 21, pp 6374–6383, 1997,"Identification of a Species=specific inhibitor of glycosylphosphatidylinositol synthesis".

*Primary Examiner*—Ba K. Trinh
(74) *Attorney, Agent, or Firm*—Nixon & Vanderhye

(57) ABSTRACT

A compound represented by the formula [I]

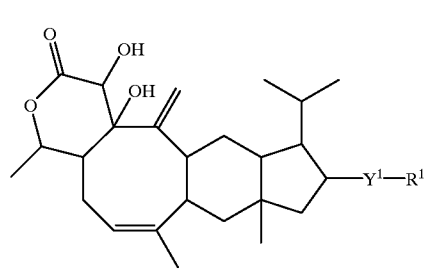

wherein
$Y^1$ represents an oxygen atom, or a group represented by NH, O—CO, O—SO$_2$, O—CO—NH, O—CS—NH, NH—CO, NH—SO$_2$, NH—CO—NH or NH—CS—NH, $R^1$ represents an alkyl group, an alkenyl group, an alkynyl group, an aryl group, an aralkyl group, an arylalkenyl group, an arylalkynyl group, a cycloalkyl group, a cycloalkylalkyl group, an alkylcarbonyl group, an alkoxycarbonyl group, an arylcarbonyl group or a heterocyclic group, each optionally having a substituent, or a pharmacologically acceptable salt or ester thereof.

The compound shows an excellent antifungal activity on fungi on which existing antifungal agents cannot sufficiently display their effects, and thus is useful as an antifungal agent.

11 Claims, No Drawings

SESTERTERPENE DERIVATIVES EXHIBITING ANTIFUNGAL ACTIVITIES

This application is a 371 of PCT/JP99/04198 dated Aug. 4, 1999.

TECHNICAL FIELD

This invention is useful in the field of pharmaceuticals, and more specifically relates to a novel antifungal agent.

BACKGROUND ART

In the field of antifungal agents, many compounds have already been put to practical use as pharmaceuticals. For example, flucytosine is known to be a less poisonous antifungal agent since it is specifically taken into certain species of fungi and exerts its antifungal activity, but it has the disadvantages that the species of fungi on which it is effective are limited and moreover, it should be used, at present, together with another antifungal agent because of early emergence of resistant fungi [Shinkin, Shinkin-sho, Kagaku Ryoho (Fungi, Fungous Diseases and Chemotherapy) written by Kazuo IWATA, pages 129–130 (1994), Soft Science Co.] (hereinafter, referred to as Reference A). Amphotericin B is an antifungal agent having a strong antifungal activity and capable of exerting the effect on wide species of fungi, but has the disadvantage that it has strong toxicity because it also acts on human cell membrane sterols (Reference A, pages 156–157). In view of the disadvantages of flucytosine and amphotericin B, azole-type antifungal agents such as miconazole, fluconazole and itraconazole, exerting their antifungal activities by inhibiting the ergosterol synthesis pathway of fungi, are now generally used. However, as a result of frequent use of these various azole-type antifungal agents in treatment and prophylaxis of fungous diseases, the problem of emergence of fungi resistant to azole-type antifungal agents arose (Reference A, pages 123–135). Since azole-type antifungal agents are the same in their action mechanisms and have similar chemical structures, the emergence of fungi resistant thereto caused the serious problem that, on fungi which acquired resistance to one of azole-type antifungal agents, other azole-type antifungal agents cannot exert a sufficient effect [Denning D W. et al., European Journal of Clinical Microbiology & Infectious Disease, volume 16, No. 4, pages 261–280, 1997].

Compounds analogous to the compounds of the invention in structure are disclosed in an international application published based on Patent Cooperation Treaty (International Publication No. WO97/19186, International Publication Date: May 29, 1997) and an European published patent application corresponding thereto, EP 0877091 A1, and it is disclosed therein that the compounds have novel structures and exert an excellent antifungal activity on some fungi. However, the compounds are poor in extent of chemical structure since they are secondary metabolites of microorganisms, and in the international application, only such limited compounds are disclosed that in the general formula [I], not only $Y^1$ is limited to a group represented by O—CO, but $R^1$ is limited to a $C_7$–$C_9$ alkyl group or a $C_7$ aralkyl group and the substituent of $R^1$ is almost always a hydroxyl group.

Namely, in compounds of the general formula [1] of the invention, compounds wherein $Y^1$ is other than O—CO, specifically $Y^1$ represents an oxygen atom, NH, O—$SO_2$, NH—CO, O—CO—NH, O—CS—NH, NH—$SO_2$, NH—CO—NH or NH—CS—NH, or compounds wherein even when $Y^1$ is O—CO, $R^1$ is other than a $C_7$–$C_9$ alkyl group or a $C_7$ aralkyl group, specifically $R^1$ represents a $C_1$–$C_5$ alkyl group, a $C_2$–$C_{10}$ alkenyl group, a $C_3$–$C_6$ alkynyl group, a $C_6$–$C_{12}$ aryl group, a $C_8$–$C_{15}$ aralkyl group, a $C_9$–$C_{15}$ arylalkenyl group, a $C_9$–$C_{15}$ arylalkynyl group, a $C_3$–$C_6$ cycloalkyl group, a $C_3$–$C_6$ cycloalkyl $C_1$–$C_{16}$ alkyl group, a $C_1$–$C_{16}$ alkylcarbonyl group, a $C_1$–$C_{16}$ alkoxycarbonyl group, a $C_6$–$C_{12}$ arylcarbonyl group or a heterocyclic group; or a $C_1$–$C_5$ alkyl group, a $C_2$–$C_{10}$ alkenyl group, a $C_3$–$C_6$ alkynyl group, a $C_6$–$C_{12}$ aryl group, a $C_7$–$C_{15}$ aralkyl group, a $C_9$–$C_{15}$ arylalkenyl group, a $C_9$–$C_{15}$ arylalkynyl group, a $C_3$–$C_6$ cycloalkyl group, a $C_3$–$C_6$ cycloalkyl $C_1$–$C_{16}$ alkyl group, a $C_1$–$C_{16}$ alkylcarbonyl group, a $C_1$–$C_{16}$ alkoxycarbonyl group, a $C_6$–$C_{12}$ arylcarbonyl group or a heterocyclic group, each having 1 to 5 substituents selected from the group consisting of a halogen atom, a cyano group, a hydroxy group, a $C_1$–$C_{16}$ alkyl group (excluding the case where $R^1$ is a $C_1$–$C_5$ alkyl group), a $C_1$–$C_{16}$ alkoxy group, a $C_1$–$C_{16}$ alkylcarbonyloxy group, an amino group, a mono-$C_1$–$C_{16}$ alkylamino group, a di-$C_1$–$C_{16}$ alkylamino group, a carboxyl group, a $C_1$–$C_{16}$ alkoxycarbonyl group, an aminocarbonyl group, a sulfo group, a $C_6$–$C_{12}$ aryloxy group, a $C_7$–$C_{15}$ aralkyloxy group and a hetersocyclic group, are novel compounds not disclosed in literatures, and these compounds and their use are not specifically disclosed nor suggested. Further, it cannot readily be conceived by a person skilled in the art that the compounds of the invention exert good antifungal activity on fungi against which the effects of the above compounds could not be exerted.

DISCLOSURE OF INVENTION

The effects of existing antifungal agents on various kinds of harmful fungi are not always sufficient, and emergence of fungi resistant to these antifungal agents, especially fungi resistant to azole-type antifungal agents being frequently used gets to be clinically a large problem. Thus, development of medicaments effective on harmful fungi and resistant fugi against which these existing antifungal agents cannot sufficiently exert their effects has been desired, and this invention aims to provide novel antifungal agent capable of meeting the desire, and it is the problem to be solved by the invention to provide a medicament exerting an antifungal effect on not only various fungi but also resistant fungi.

The present inventors have intensely studied for solving the problem, and as a result, they found that a compound represented by the general formula [I], or a pharmacologically acceptable salt or ester thereof has an excellent antifungal activity, and completed the invention. More specifically, the invention relates to a compound represented by the formula [I]

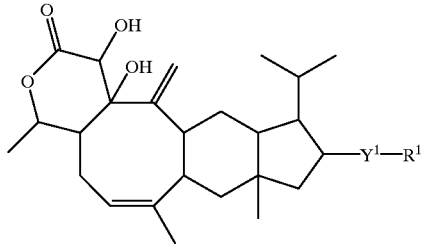

wherein $Y^1$ represents an oxygen atom, or a group represented by NH, O—CO, O—$SO_2$, NH—CO, O—CO—NH, O—CS—NH, NH—SO$_2$, NH—CO—NH or NH—CS—NH, $R^1$ represents a group selected from the group consisting of, each unsubstituted, a $C_1$–$C_{16}$ alkyl group, a $C_2$–$C_{10}$ alkenyl group, a $C_3$–$C_6$ alkynyl group, a $C_6$–$C_{12}$ aryl group, a $C_7$–$C_{15}$ aralkyl group, a $C_9$–$C_{15}$ arylalkenyl group, a $C_9$–$C_{15}$ arylalkynyl group, a $C_3$–$C_6$ cycloalkyl group, a $C_3$–$C_6$ cycloalkyl $C_1$–$C_{16}$ alkyl group, a $C_1$–$C_{16}$ alkylcarbonyl group, a $C_1$–$C_{16}$ alkoxycarbonyl group, a $C_6$–$C_{12}$ arylcarbonyl group and a heterocyclic group; or a group selected from the group consisting of a $C_1$–$C_{16}$ alkyl group, a $C_2$–$C_{10}$ alkenyl group, a $C_3$–$C_6$ alkynyl group, a $C_6$–$C_{12}$ aryl group, a $C_7$–$C_{15}$ aralkyl group, a $C_9$–$C_{15}$ arylalkenyl group, a $C_9$–$C_{15}$ arylalkynyl group, a $C_3$–$C_6$ cycloalkyl group, a $C_3$–$C_6$ cycloalkyl $C_1$–$C_{16}$ alkyl group, a $C_1$–$C_{16}$ alkylcarbonyl group, a $C_1$–$C_{16}$ alkoxycarbonyl group, a $C_6$–$C_{12}$ arylcarbonyl group and a heterocyclic group, each having 1 to 5 substituents selected from the group consisting of a halogen atom, a cyano group, a hydroxy group, a $C_1$–$C_{16}$ alkyl group (excluding the case where $R^1$ is a $C_1$–$C_{16}$ alkyl group), a $C_1$–$C_{16}$ alkoxy group, a $C_1$–$C_{16}$ alkylcarbonyloxy group, an amino group, a mono-$C_1$–$C_{16}$ alkylamino group, a di-$C_1$–$C_{16}$ alkylamino group, a carboxyl group, a $C_1$–$C_{16}$ alkoxycarbonyl group, an aminocarbonyl group, a sulfo group, a $C_6$–$C_{12}$ aryloxy group, a $C_7$–$C_{15}$ aralkyloxy group, a $C_1$–$C_{16}$ alkylcarbonyl group, a $C_1$–$C_{16}$ alkoxycarbonyl group, a $C_6$–$C_{12}$ arylcarbonyl group and a heterocyclic group;

with the proviso that when $Y^1$ represents O—CO, $R^1$ does not represent a 2,4-dimethylhexyl group, a 2-hydroxy-2,4-dimethylhexyl group, a 1,2-dihydroxy-2,4-dimethylhexyl group, a 1-hydroxy-3,5-dimethylheptyl group, a 1,2-dihydroxy-5-methylheptyl group, a 1,2-dihydroxy-3,5-dimethylheptyl group or a 1-hydroxy-1-phenylmethyl group, or a pharmacologically acceptable salt or ester thereof; and an antifungal agent containing it as an effective ingredient.

BEST MODE FOR CARRYING OUT THE INVENTION

Description is made on symbols and terminology used in the specification.

The $C_1$–$C_{16}$ alkyl group means a straight-chain or branched alkyl group having 1 to 16 carbon atoms, and there can, for example, be mentioned a methyl group, an ethyl group, a propyl group, an isopropyl group, a butyl group, an isobutyl group, a sec-butyl group, a tert-butyl group, a pentyl group, an isopentyl group, a neopentyl group, a hexyl group, a decyl group, a dodecyl group, a hexadecyl group, etc. Among these alkyl groups, $C_1$–$C_5$ alkyl groups are preferred, and $C_3$–$C_5$ alkyl groups are further preferred.

The $C_2$–$C_{10}$ alkenyl group means a straight-chain or branched alkenyl group having 2 to 10 carbon atoms and containing 1 to 5, preferably 1 to 2, more preferably 1 double bonds, and there can, for example, be mentioned a propenyl group, a 2-butenyl group, a 3-butenyl group, a 3-pentenyl group, a 4-hexenyl group, a 1,3-hexadienyl group, etc. Among these alkenyl groups, $C_3$–$C_5$ alkyl groups are preferred.

The $C_3$–$C_6$ alkynyl group means a straight-chain or branched alkynyl group having 3 to 6 carbon atoms and containing 1 to 3, preferably 1 triple bonds, and there can, for example, be mentioned a propynyl group, a 2-butynyl group, a 3-butynyl group, a 3-pentynyl group, a 4-hexynyl group, a 1-decynyl group, etc.

The $C_6$–$C_{12}$ aryl group means a monocyclic or polycyclic aryl group having 6 to 12 carbon atoms, and there can, for example, be mentioned a phenyl group, a naphthyl group, a tetrahydronaphthyl group, etc.

The $C_9$–$C_{15}$ arylalkenyl group means an alkenyl group having 3 to 5 carbon atoms substituted with the above-mentioned $C_6$–$C_{12}$ aryl group, provided that the arylalkenyl group has 9 to 15 carbon atoms as a whole, and there can, for example, be mentioned a phenylpropenyl group, a phenylpentenyl group, etc.

The $C_9$–$C_{15}$ arylalkynyl group means an alkynyl group having 3 to 5 carbon atoms substituted with the above-mentioned $C_6$–$C_{12}$ aryl group, provided that the arylalkynyl group has 9 to 15 carbon atoms as a whole, and there can, for example, be mentioned a phenylpropynyl group, a phenylpentyn-3-yl group, etc.

The $C_6$–$C_{12}$ arylcarbony group means a group wherein the above-mentioned $C_6$–$C_{12}$ aryl group is bonded to a carbonyl group, and there can, for example, be mentioned a benzoyl group, a naphthoyl group, a tetrahydronaphthoyl group, etc.

The $C_6$–$C_{12}$ aryloxy group means a group wherein the abovementioned $C_6$–$C_{12}$ aryl group is bonded to an oxygen atom, and there can, for example, be mentioned a phenyloxy group, a naphthyloxy group, a tetrahydronaphthyloxy group, etc.

As the halogen atom, there can be mentioned a fluorine atom, a chlorine atom, a bromine atom and an iodine atom.

The $C_1$–$C_{16}$, alkoxy group means a group wherein the above-mentioned $C_1$–$C_{16}$, preferably $C_1$–$C_6$ alkyl group is bonded to an oxygen atom, and there can, for example, be mentioned a methoxy group, an ethoxy group, a propoxy group, an isopropoxy group, a butoxy group, an isobutoxy group, a sec-butoxy group, a tert-butoxy group, a pentyloxy group, an isopentyloxy group, a neopentyloxy group, a hexyloxy group, a decyloxy group, a dodecyloxy group, a hexadecyloxy group, etc.

The $C_1$–$C_{16}$ alkoxycarbonyl group means a group wherein the above-mentioned $C_1$–$C_{16}$, preferably $C_1$–$C_6$ alkoxy group is bonded to a carbonyl group, and there can, for example, be mentioned a methoxycarbonyl group, an ethoxycarbonyl group, a propoxycarbonyl group, an isopropoxycarbonyl group, a butoxycarbonyl group, an isobutoxycarbonyl group, a sec-butoxycarbonyl group, a tert-butoxycarbonyl group, a pentyloxycarbonyl group, an isopentyloxycarbonyl group, a neopentyloxycarbonyl group, a hexyloxycarbonyl group, a decyloxycarbonyl group, a dodecyloxycarbonyl group, a hexadecyloxycarbonyl group, etc.

The $C_1$–$C_{16}$ alkylcarbonyl group means a group wherein the above-mentioned $C_1$–$C_{16}$, preferably $C_1$–$C_5$ alkyl group is bonded to a carbonyl group, and there can, for example, be mentioned an acetyl group, a propionyl group, a butyryl group, a pentanoyl group, an isopentanoyl group, a hexanoyl group, a decanoyl group, a dodecanoyl group, a hexadecanoyl group, etc.

The $C_1$–$C_{16}$ alkylcarbonyloxy group means a group wherein the above-mentioned $C_1$–$C_{16}$, preferably $C_1$–$C_5$ alkylcarbonyl group is bonded to an oxygen atom, and there can, for example, be mentioned a methylcarbonyloxy group, an ethylcarbonyloxy group, a propylcarbonyloxy group, an isopropylcarbonyloxy group, a butylcarbonyloxy group, an isobutylcarbonyloxy group, a sec-butylcarbonyloxy group, a tert-butylcarbonyloxy group, a pentylcarbonyloxy group, an isopentylcarbonyloxy group, a neopentylcarbonyloxy group, a hexylcarbonyloxy group, a decylcarbonyloxy group, a dodecylcarbonyloxy group, a hexadecylcarbonyloxy group, a palmitoyloxy group, etc.

The mono-$C_1$–$C_{16}$ alkylamino group means an amino group mono-substituted with the above-mentioned $C_1$–$C_{16}$, preferably $C_1$–$C_6$ alkyl group, and there can, for example, be mentioned a methylamino group, an ethylamino group, a propylamino group, an isopropylamino group, a butylamino group, an isobutylamino group, a sec-butylamino group, a tert-butylamino group, a pentylamino group, an isopentylamino group, a neopentylamino group, a hexylamino group, etc.

The di-$C_1$–$C_{16}$ alkylamino group means an amino group di-substituted with the same or different, the above-mentioned $C_1$–$C_{16}$, preferably $C_1$–$C_6$ alkyl group, and there can, for example, be mentioned a dimethylamino group, an diethylamino group, an ethylpropylamino group, a dipropylamino group, a butylmethylaminol group, a dibutylamino group, a butylethylamino group, a methylpentylaminol group, a hexylmethylamino group, an ethylhexylamino group, etc.

The $C_3$–$C_6$ cycloalkyl group means a cycloalkyl group having 3 to 6 carbon atoms, and there can be mentioned a cyclopropyl group, a cyclobutyl group, a cyclopentyl group and a cyclohexyl group.

The $C_3$–$C_6$ cycloalkyl $C_1$–$C_{16}$ alkyl group means the above-mentioned $C_1$–$C_{16}$, preferably $C_1$–$C_6$, more preferably $C_1$–$C_4$ alkyl group substituted with the above-mentioned $C_3$–$C_6$ cycloalkyl group, and there can be mentioned a cyclopropylmethyl group, a cyclobutylmethyl group, a cyclopentylmethyl group, a cyclohexylmethyl group, a cyclopropylethyl group, a cyclobutylethyl group, a cyclopentylethyl group, a cyclohexylethyl group, a 3-cyclohexylpropyl group, a 3-cyclopentylpropyl group, a 4-cyclohexylbutyl group, a 4-cyclopentylbutyl group, etc., and the carbon number of the $C_3$–$C_6$ cycloalkyl $C_1$–$C_{16}$ alkyl group is preferably 4 to 10 in total.

The $C_7$–$C_{15}$ aralkyl group means the above-mentioned $C_1$–$C_9$ alkyl group substituted with the above-mentioned $C_1$–$C_{12}$ aryl group, provided that the aralkyl group has 7 to 15 carbon atoms in total and preferably means a phenyl $C_1$–$C_9$ alkyl group, and there can, for example, be mentioned a benzyl group, a phenethyl group, a phenylpropyl group, a phenylbutyl group, a phenylpentyl group, a naphthylmethyl group, a naphthylethyl group, etc.

The $C_7$–$C_{15}$ aralkyloxy group means a group wherein the above-mentioned $C_7$–$C_{15}$ aralkyl group, preferably the above-mentioned phenyl $C_1$–$C_9$ alkyl group is bonded to an oxygen atom, and there can, for example, be mentioned a benzyloxy group, a phenethyloxy group, a phenylpropyloxy group, a phenylbutyloxy group, a phenylpentyloxy group, a naphthylmethyloxy group, a naphthylethyloxy group, etc.

The heterocyclic group is an aromatic or nonaromatic heterocyclic group, and each of the aromatic or nonaromatic heterocyclic group is a 5- to 7-membered, preferably 5- or 6-membered monocyclic heterocyclic group containing 1 to 4, preferably 1 to 3, more preferably 1 or 2 hetero atoms selected from the group consisting of a nitrogen atom, an oxygen atom and a sulfur atom, or a condensed ring-type heterocyclic group wherein the above monocyclic heterocyclic group is condensed with preferably 1 or 2 the above-mentioned $C_3$–$C_6$ cycloalkyl group, preferably 1 or 2 the above-mentioned $C_6$–$C_{12}$ aryl group, preferably a phenyl group, or preferably 1 another monocyclic heterocyclic group which is the same or different and defined as above. In such a condensed ring-type heterocyclic group, the number of the hetero atom is preferably 1 to 4, and the nitrogen atom is not contained or can be contained in a number of 1 to 4, the oxygen atom is not contained or can be contained in a number of 1 to 2, particularly 1, and the sulfur atom is not contained or can be contained in a number of 1 or 2.

As specific example of the heterocyclic group, there can be mentioned a pyrrolyl group, a furyl group, a thienyl group, an oxazolyl group, an isoxazolyl group, a thiazolyl group, an isothiazolyl group, an imidazolyl group, a pyrazolyl group, an oxadiazolyl group, a thiadiazolyl group, a triazolyl group, a tetrazolyl group, a furazanyl group, a pyridyl group, a pyridazinyl group, a pyrimidinyl group, a pyrazinyl group, a triazinyl group, a dihydrothienyl group, a tetrahydropyranyl group, a tetrahydrofuranyl group, a tetrahydrothienyl group, a pyrrolinyl group, a pyrrolidinyl group, an imidazolidinyl group, an imidazolinyl group, a piperidinyl group, a piperazinyl group, an oxazolinyl group, an isoxazolinyl group, an isoxazolidinyl group, a thiazolinyl group, a thiazolidinyl group, an isothiazolinyl group, an isothiazolidinyl group, a 1,2-dithiolanyl group, a 1,3-dithiolanyl group, a 1,2-dithiolyl group, a 1,3-dithiolyl group, a dihydrothiopyranyl group, a tetrahydrothiopyranyl group, a 1,4-dithianyl group, a 1,4-dithiinyl group, a 1,4-oxathiinyl group, a thiomorpholinyl group, a morpholinyl group, an indolyl group, an isoindolyl group, a quinolyl group, an isoquinolyl group, a quinolizinyl group, a cinnolinyl group, a quinoxalinyl group, a phthalazinyl group, a pteridinyl group, a purinyl group, a carbazolyl group, an acridinyl group, a phenazinyl group, a benzofuryl group, a benzothienyl group, a chromanyl group, an isochromanyl group, a xanthenyl group, a benzoxazolyl group, an imidazothiazolyl group, a thieno[2,3-b]thienyl group, a 1,4-dithianaphthyl group, etc.

The $C_7$–$C_{15}$ aralkylamino group means a group wherein the above-mentioned $C_7$–$Cl_{15}$ aralkyl group, preferably a phenyl $C_1$–$C_9$ alkyl group is bonded to a nitrogen atom, and there can, for example, be mentioned a benzylamino group, a phenethylamino group, a phenylpropylamino group, a phenylbutylamino group, a phenylpentylamino group, a naphthylmethylamino group, a naphthylethylamino group, etc.

The halo-$C_1$–$C_{16}$ alkyl group means the above-mentioned $C_1$–$C_{15}$, preferably $C_1$–$C_6$, more preferably $C_1$ or $C_2$ alkyl group, each being substituted with 1 to 3 halogen atoms, and there can, for example, be mentioned a fluoromethyl group, a difluoromethyl group, a trifluoromethyl group, a 1-fluoroethyl group, a 2-fluoroethyl group, a 1,2-difluoroethyl group, a chloromethyl group, a dichloromethyl group, a 1-chloroethyl group, a 2-chloroethyl group, a 1,2-dichloroethyl group, a bromomethyl group, a dibromomethyl group, a 1-bromoethyl group, a 2-bromoethyl group, a 1,2-dibromoethyl group, etc.

The hydroxy $C_1$–$C_{16}$ alkyl group means the above-mentioned $C_1$–$C_{16}$, preferably $C_1$–$C_5$, more preferably $C_1$–$C_3$ alkyl group substituted with 1 to 3, preferably 1 or 2 hydroxyl groups, and there can, for example, be mentioned a hydroxymethyl group, a 1-hydroxyethyl group, a 2-hydroxyethyl group, a 1,2-dihydroxyethyl group, a 1-hydroxypropyl group, a 2-hydroxypropyl group, a 3-hydroxypropyl group, etc.

The amino $C_1$–$C_{16}$ alkyl group means the above-mentioned $C_1$–$C_{16}$, preferably $C_1$–$C_{16}$, more preferably $C_1$–$C_3$ alkyl group substituted with 1 to 3, preferably 1 or 2 amino groups, and there can, for example, be mentioned an aminomethyl group, a 1-aminoethyl group, a 2-aminoethyl group, a 1,2-diaminoethyl group, a 1-aminopropyl group, a 2-aminopropyl group, a 3-aminopropyl group, etc.

The carboxy-$C_1$–$C_{16}$ alkyl group means the above-mentioned $C_1$–$C_{16}$, preferably $C_1$–$C_6$, more preferably $C_1$–$C_3$ alkyl group substituted with 1 to 3, preferably 1 or 2 carboxy groups, and there can, for example, be mentioned a carboxymethyl group, a 1-carboxyethyl group, a 2-carboxyethyl group, a 1,2-dicarboxyethyl group, a 1-carboxypropyl group, a 2-carboxypropyl group, a 3-carboxypropyl group, etc.

$Y^1$ represents an oxygen atom, or a group represented by NH, O—CO, O—SO$_2$, O—CO—NH, O—CS—NH, NH—CO, NH—SO$_2$, NH—CO—NH or NH—CS—NH, and is preferably an oxygen atom, or a group represented by O—CO, O—SO$_2$, O—CO—NH, O—CS—NH or NH—CO, and more preferably a group represented by O—CO, O—CO—NH or NH—CO.

In the definition of $Y^1$, it is assumed that the atom or atomic group described on the left side is bonded to the condensed ring, and the atomic group described on the right side is bonded to $R^1$. Therefore, for example in the case of O—CO, O is bonded to the condensed ring and CO to $R^1$.

$R^1$ represents a group selected from the group consisting of, each unsubstituted, a $C_1$–$C_{16}$ alkyl group, a $C_2$–$C_{10}$ alkenyl group, a $C_3$–$C_6$ alkynyl group, a $C_6$–$C_{12}$ aryl group, a $C_7$–$C_{15}$ aralkyl group, a $C_9$–$C_{15}$ arylalkenyl group, a $C_9$–$C_{15}$ arylalkynyl group, a $C_3$–$C_6$ cycloalkyl group, a $C_3$–$C_6$ cycloalkyl $C_1$–$C_{16}$ alkyl group, a $C_1$–$C_{16}$ alkylcarbonyl group, a $C_1$–$C_{16}$ alkoxycarbonyl group, a $C_6$–$C_{12}$ arylcarbonyl group and a heterocyclic group; or a group selected from the group consisting of a $C_1$–$C_{16}$ alkyl group, a $C_2$–$C_{10}$ alkenyl group, a $C_3$–$C_6$ alkynyl group, a $C_6$–$C_{12}$ aryl group, a $C_7$–$C_{15}$ aralkyl group, a $C_9$–$C_{15}$ arylalkenyl group, a $C_9$–$C_{15}$ arylalkynyl group, a $C_3$–$C_6$ cycloalkyl group, a $C_3$–$C_6$ cycloalkyl $C_1$–$C_{16}$ alkyl group, a $C_1$–$C_{16}$ alkylcarbonyl group, a $C_1$–$C_{16}$ alkoxycarbonyl group, a $C_6$–$C_{12}$ arylcarbonyl group and a heterocyclic group, each having 1 to 5 substituents selected from the group consisting of a halogen atom, a cyano group, a hydroxy group, a $C_1$–$C_{16}$ alkyl group (excluding the case where $R^1$ is a $C_1$–$C_{16}$ alkyl group), a $C_1$–$C_{16}$ alkoxy group, a $C_1$–$C_{16}$ alkylcarbonyloxy group, an amino group, a mono-$C_1$–$C_{16}$ alkylamino group, a di-$C_1$–$C_{16}$ alkylamino group, a carboxyl group, a $C_1$–$C_{16}$ alkoxycarbonyl group, an aminocarbonyl group, a sulfo group, a $C_6$–$C_{12}$ aryloxy group, a $C_7$–$C_{15}$ aralkyloxy group and a heterocyclic group;

with the proviso that when $Y^1$ represents O—CO, $R^1$ does not represent a 2,4-dimethylhexyl group, a 2-hydroxy-2,4-dimethylhexyl group, a 1,2-dihydroxy-2,4-dimethylhexyl group, a 1-hydroxy-3,5-dimethylheptyl group, a 1,2-dihydroxy-5-methylheptyl group, a 1,2-dihydroxy-3,5-dimethylheptyl group or a 1-hydroxy-1-phenylmethyl group.

Preferably, $R^1$ is, each unsubstituted, a $C_1$–$C_5$ alkyl group, a $C_2$–$C_{10}$ alkenyl group, a $C_3$–$C_6$ alkynyl group, a $C_6$–$C_{12}$ aryl group, a $C_7$–$C_{15}$ aralkyl group, a $C_9$–$C_{15}$ arylalkenyl group, a $C_9$–$C_{15}$ arylalkynyl group, a $C_3$–$C_6$ cycloalkyl group, a $C_3$–$C_6$ cycloalkyl $C_1$–$C_{16}$ alkyl group, a $C_1$–$C_{16}$ alkylcarbonyl group, a $C_1$–$C_{16}$ alkoxycarbonyl group, a $C_6$–$C_{12}$ arylcarbonyl group or a heterocyclic group; or a $C_1$–$C_5$ alkyl group, a $C_2$–$C_{10}$ alkenyl group, a $C_3$–$C_6$ alkynyl group, a $C_6$–$C_{12}$ aryl group, a $C_7$–$C_{15}$ aralkyl group, a $C_9$–$C_{15}$ arylalkenyl group, a $C_9$–$C_{15}$ arylalkynyl group, a $C_3$–$C_6$ cycloalkyl group, a $C_3$–$C_6$ cycloalkyl $C_1$–$C_{16}$ alkyl group, a $C_1$–$C_{16}$ alkylcarbonyl group, a $C_1$–$C_{16}$ alkoxycarbonyl group, a $C_1$–$C_{12}$ arylcarbonyl group or a heterocyclic group, each having 1 to 5 substituents selected from the group consisting of a halogen atom, a cyano group, a hydroxy group, a $C_1$–$C_{16}$ alkyl group (excluding the case where $R^1$ is a $C_1$–$C_5$ alkyl group), a $C_1$–$C_{16}$ alkoxy group, a $C_1$–$C_{16}$ alkylcarbonyloxy group, an amino group, a mono-$C_3$–$C_{16}$ alkylamino group, a di-$C_1$–$C_{16}$ alkylamino group, a carboxyl group, a $C_1$–$C_{16}$ alkoxycarbonyl group, an aminocarbonyl group, a sulfo group, a $C_6$–$C_{12}$ aryloxy group, a $C_7$–$C_{15}$ aralkyloxy group and a heterocyclic group.

More preferably, $R^1$ is a group selected from the group consisting of, each unsubstituted, a $C_1$–$C_5$ alkyl group, a $C_2$–$C_{10}$, particularly $C_3$–$C_5$ alkenyl group, a phenyl group, a phenyl $C_1$–$C_9$, particularly $C_1$–$C_3$ alkyl group such as a phenylmethyl group or a phenylethyl group, a phenyl $C_3$–$C_5$ alkenyl group such as a phenylethenyl group, a $C_3$–$C_6$ cycloalkyl group, particularly a cyclopentyl group or a cyclohexyl group, a $C_1$–$C_{15}$, particularly $C_1$–$C_5$ alkylcarbonyl group, a $C_1$–$C_{16}$, particularly $C_1$–$C_6$ alkoxycarbonyl group such as an ethoxycarbonyl group, a benzoyl group and a heterocyclic group; or a group selected from the group consisting of a $C_1$–$C_5$ alkyl group, a $C_2$–$C_{10}$, particularly $C_3$–$C_5$ alkenylgroup, aphenyl group, aphenyl-$C_1$–$C_9$, particularly $C_1$–$C_3$ alkyl group such as a phenylmethyl group or a phenylethyl group, a phenyl $C_3$–$C_5$ alkenyl group such as a phenylethenyl group, a $C_3$–$C_6$ cycloalkyl group, particularly a cyclopentyl group or a cyclohexyl group, a $C_1$–$C_{16}$, particularly $C_1$–$C_5$ alkylcarbonyl group, a $C_1$–$C_{16}$, particularly $C_1$–$C_6$ alkoxycarbonyl group such as an ethoxycarbonyl group, a benzoyl group and a heterocyclic group, each having 1 or 2 substituents selected from the group consisting of a halogen atom, a cyano group, a $C_1$–$C_3$ alkoxy group and a $C_1$–$C_3$ alkyl group (excluding the case where $R^1$ is a $C_1$–$C_5$ alkyl group).

In the above, as the heterocyclic group, there can specifically be mentioned those mentioned above, but particularly preferred are a pyridyl group, a quinolyl group, a tetrahydropyranyl group, a tetrahydrofuranyl group, a benzothienyl group, a benzofuryl group and an indolyl group.

As to the substituent in the definition of $R^1$, the number of the substituent, a halogen atom, a hydroxy group, a $C_1$–$C_{16}$ alkyl group or a $C_1$–$C_{16}$ alkoxy group is preferably 1 to 3, particularly 1 to 2, and the number of another substituent is preferably 1. The total number of the same or different substituents can be 1 to 5, but is preferably 1 to 3, particularly 1 or 2.

In preparation of compounds of the invention, functional groups not taking part in the reaction are protected according to necessity, and description is made below about protective groups for such functional groups.

As protective groups for a hydroxyl group, there can be mentioned a lower alkylsilyl group such as, for example, a trimethylsilyl or a tert-butyldimethylsilyl group; a lower alkoxymethyl group such as, for example, a methoxymethyl group or a 2-methoxyethoxymethyl group; for example, a tetrahydropyranyl group; an aralkyl group such as, for example, a benzyl group, a p-methoxybenzyl group, a p-nitrobenzyl group or a trityl group; an acyl group such as, for example, a formyl group or an acetyl group; etc., and particularly preferred are a methoxymethyl group, a tetrahydropyranyl group, a trityl group, a tert-butyldimethylsilyl group, an acetyl group, etc.

As protective groups for an amino group, there can be mentioned an aralkylidene group such as, for example, a benzylidene group, a p-chlorobenzylidene group or a p-nitrobenzylidene group; an aralkyl group such as, for example, a benzyl group, a p-methoxybenzyl group, a p-nitrobenzyl group, a benzhydryl group or a trityl group; a lower alkanoyl group such as, for example, a formyl group, an actyl group, a propionyl group, a butyryl group or a pivaloyl group; a lower haloalkanoyl group such as, for example, a trifluoroacetyl group; a lower alkoxycarbonyl group such as, for example, a methoxycarbonyl group, an ethoxycarbonyl group, a propoxycarbonyl group or a tert-butoxycarbonyl group; a lower haloalkoxycarbonyl group such as, for example, a 2,2,2-trichloroethoxycarbonyl group; an alkenyloxycarbonyl group such as, for example, a 2-propenyloxycarbonyl group; an aralkyloxycarbonyl group such as, for example, a benzyloxycarbonyl group or a p-nitrobenzyloxycarbonyl group; a lower alkylsilyl group such as, for example, a trimethylsilyl group or a tert-butyldimethylsilyl group, etc., and particularly preferred are an acetyl group, a trifluoroacetyl group, a tert-butoxycarbonyl group, a benzyloxycarbonyl group, etc.

As protective groups for a carboxyl group, there can be mentioned a lower alkyl group such as, for example, a methyl group, an ethyl group, a propyl group, an isopropyl group or a tert-butyl group; a lower haloalkyl group such as, for example, a 2,2,2-trichloroethyl group; a lower alkenyl group such as, for example, a 2-propenyl group; an aralkyl group such as, for example, a benzyl group, a p-methoxybenzyl group, a p-nitrobenzyl group, a benzhydryl group or a trityl group, etc., and particularly preferred are a methyl group, an ethyl group, a tert-butyl group, a 2-propenyl group, a benzyl group, a p-methoxybenzyl group, a benzhydryl group, etc.

The salts of compounds represented by the general formula [I] means pharmacologically acceptable common ones, and there can be mentioned salts, for example, base addition salts in the acidic group in the case where the compounds have a carboxyl group or another acidic group, or acid addition salts in the amino group in the case where the compounds have an amino group or in the basic heteroaromatic ring in the case where the compounds have a basic heterocycle.

As the base addition salts, there can be mentioned an alkali metal salt such as, for example, a sodium salt or a potassium salt; an alkaline earth metal salt such as, for example, a calcium salt or amagnesium salt; for example, an ammonium salt; an organic amine salt such as, for example, a trimethylamine salt, a triethylamine salt, a dicyclohexylamine salt, an ethanolamine salt, a diethanolamine salt, a triethanolamine salt, a procaine salt or an N,N'-dibenzylethylenediamine salt, etc.

As the acid addition salts, there can be mentioned an inorganic acid salt such as, for example, hydrochloride, sulfate, nitrate, phosphate or perchlorate; an organic acid salt such as, for example, maleate, fumarate, tartrate, citrate, ascorbate or trifluoroacetate; sulfonate such as methanesulfonate, isethionate, benzenesulfonate or p-toluenesulfonate, etc.

The ester of the compound represented by the general formula [I] means pharmacologically acceptable common ones in the carboxyl group in the case of where the compound has a carboxyl group, and as examples of the ester, there can, for example, be mentioned an ester with a lower alkyl group such as a methyl group, an ethyl group, a propyl group, an isopropyl group, a butyl group, a sec-butyl group, a tert-butyl group, a pentyl group, an isopentyl group, a neopentyl group, a cyclopropyl group, a cyclobutyl group or a cyclopentyl group, an ester with an aralkyl group such as a benzyl group or a phenethyl group, an ester with a lower alkenyl group such as an allyl group or a 2-butenyl group, an ester with a lower alkoxyalkyl group such as a methoxymethyl group, a 2-methoxyethyl group or a 2-ethoxyethyl group, an ester with a lower alkanoyloxyalkyl group such as an acetoxymethyl group, a pivaloyloxymethyl group or a 1-pivaloyloxyethyl group, an ester with a lower alkoxycarbonylalkyl group such as a methoxycarbonylmethyl group or an isopropoxycarbonylmethyl group, an ester with a lower carboxyalkyl group such as a carboxymethyl group, an ester with a lower alkoxycarbonyloxyalkyl group such as a 1-(ethoxycarbonyloxy)ethyl group or a 1-(cyclohexyloxy-carbonyloxy)ethyl group, an ester with a lower carbamoyloxyalkyl group such as a carbamoyloxymethyl group, an ester with a phthalidyl group, an ester with a (5-substituted-2-oxo-1,3-dioxol-4-yl)methyl group such as a (5-methyl-2-oxo-1,3-dioxol-4-yl)methyl group, etc.

As specific examples of the compounds of the invention having a novel structure, there can be exemplified compounds having the structures represented by the following general formulae [I-8] to [I-17].

General formula [I-8]

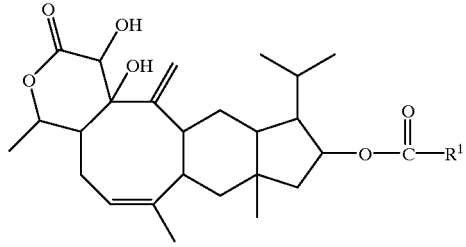

[I-8]

[wherein $R^1$ is as defined above].

Compounds represented by the formula [I-8] are included in compounds represented by the formula [I], and the compounds wherein $R^1$ is a $C_2$–$C_6$ alkyl group, a $C_2$–$C_{10}$ alkenyl group, a heterocyclic group or a hydroxy $C_2$–$C_{10}$ alkyl group; or a phenyl group or a heterocyclic group, each having a substituent are suitable, and among them, the compounds wherein $R^1$ is a $C_3$–$C_5$ alkyl group, a $C_3$–$C_5$ alkenyl group, a pyridyl group, a quinolyl group or a tetrahydrofuranyl group; or a pyridyl group, a quinolyl group, a tetrahydrofuranyl group or a phenyl group, each having 1 or 2 substituents selected from the group consisting of a halogen atom, a cyano group, a $C_1$–$C_3$ alkoxy group and a $C_1$–$C_3$ alkyl group are preferred.

General formula [I-9]

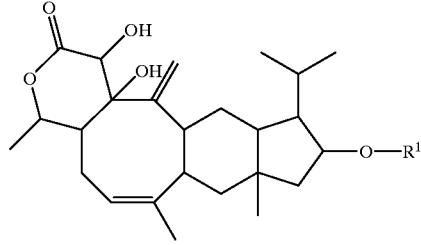

[I-9]

[wherein $R^1$ is as defined above].

Compounds represented by the formula [I-9] are included in compounds represented by the formula [I], and the compounds wherein $R^1$ is a hydroxy $C_2$–$C_{10}$ alkyl group are suitable.

General formula [I-10]

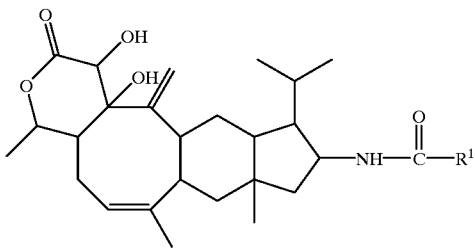

[wherein $R^1$ is as defined above].

Compounds represented by the formula [I-10] are included in compounds represented by the formula [I], and the compounds wherein $R^1$ is a hydroxy $C_2$–$C_{10}$ alkyl group; a $C_1$–$C_3$, particularly $C_1$ alkyl group substituted with a benzothienyl group, a benzofuryl group or an indolyl group; or a phenyl $C_1$–$C_3$, particularly $C_1$ alkyl group substituted with a 1 or 2 halogen atoms are suitable.

General formula [I-11]

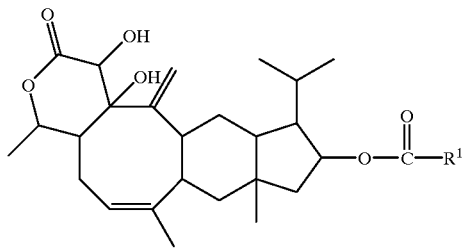

[wherein $R^1$ is as defined above].

Compounds represented by the formula [I-11] are included in compounds represented by the formula [I], and the compounds wherein $R^{1isa}$ $C_1$–$C_{10}$ alkyl group are suitable, and the compounds wherein $R^1$ is a butyl group is preferred.

General formula [I-12]

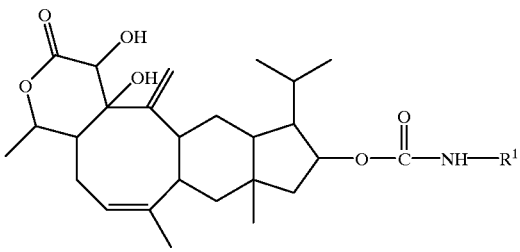

[wherein $R^1$ is as defined above].

Compounds represented by the formula [I-12] are included in compounds represented by the formula [I], and the compounds wherein $R^1$ is a $C_1$–$C_{10}$ alkyl group, a $C_2$–$C_{10}$ alkenyl group, a $C_1$–$C_{16}$ alkoxycarbonyl group, a $C_6$–$C_{10}$ aryl group, a $C_7$–$C_{15}$ aralkyl group, a heterocyclic group or a $C_3$–$C_6$ cycloalkyl group; or a $C_6$–$C_{10}$ aryl group, a heterocyclic group or a $C_7$–$C_{15}$ aralkyl group, each having a substituent are suitable, and among them, the compounds wherein $R^1$ is a $C_2$–$C_5$ alkyl group, a $C_2$–$C_5$ alkenyl group, a $C_2$–$C_5$ alkoxycarbonyl group, a cyclohexyl group, a phenyl group, a phenylmethyl group or a tetrahydropyranyl group; or a cyclohexyl group, a phenyl group, a phenylmethyl group or a tetrahydropyranyl group, each having 1 or 2 substituents selected from the group consisting of a halogen atom, a $C_1$–$C_3$ alkoxy group and a $C_1$–$C_3$ alkyl group are preferred.

General formula [I-13]

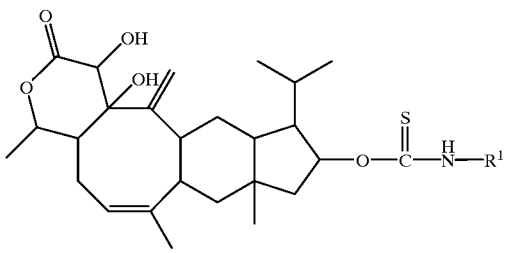

[wherein $R^1$ is as defined above].

Compounds represented by the formula [I-13] are included in compounds represented by the formula [I], and the compounds wherein $R^1$ is a $C_1$–$C_{10}$ alkyl group are suitable. General formula [I-14]

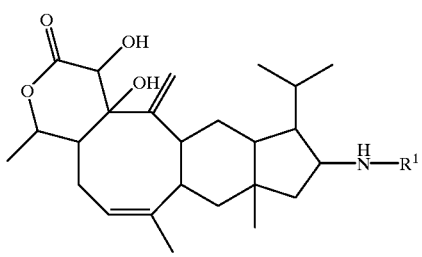

[wherein $R^1$ is as defined above].

Compounds represented by the formula [I-14] are included in compounds represented by the formula [I], and the compounds wherein $R^1$ is a $C_1$–$C_{10}$ alkyl group are suitable.

General formula [I-15]

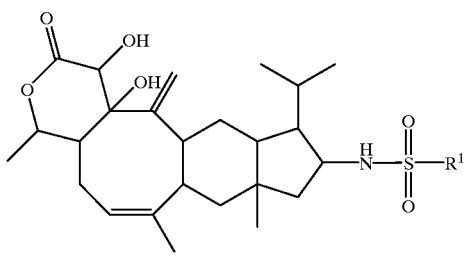

[wherein $R^1$ is as defined above].

Compounds represented by the formula [I-15] are included in compounds represented by the formula [I], and the compounds wherein $R^1$ is a $C_1$–$C_{10}$ alkyl group are suitable.

General formula [I-16]

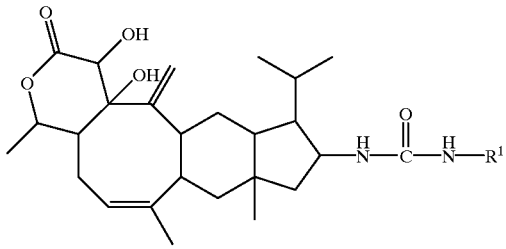

[I-16]

[wherein $R^1$ is as defined above].

Compounds represented by the formula [I-16] are included in compounds represented by the formula [I], and the compounds wherein $R^1$ is a $C_1$–$C_{10}$ alkyl group are suitable, and among them, the compound wherein $R^1$ is a butyl group is preferred.

General formula [I-17]

[I-17]

[wherein $R^1$ is as defined above].

Compounds represented by the formula [I-17] are included in compounds represented by the formula [I], and the compounds wherein $R^1$ is a $C_1$–$C_{10}$ alkyl group are suitable.

Among compounds represented by the general formula [I], compounds wherein $R^1$ is, for example, a hydrogen atom, an unsubstituted $C_1$–$C_6$ alkyl group such as, for example, an ethyl group, a propyl group, an isopropyl group, a butyl group, an isobutyl group, a tert-butyl group, a pentyl group, an isopentyl group, a hexyl group, a decyl group or a cetyl group, more preferably an ethyl group, a propyl group, a butyl group, an isobutyl group, a tert-butyl group, a pentyl group, an isopentyl group or a hexyl group; an unsubstituted $C_2$–$C_{10}$ alkenyl group such as, for example, an allyl group; an unsubstituted $C_7$–$C_{15}$ aralkyl group such as, for example, a benzyl group; a $C_1$–$C_{16}$ alkyl group having 1 to 5 substituents selected from the group consisting of a $C_6$–$C_{12}$ aryl group, a $C_6$–$C_{12}$ aryloxy group, a $C_7$–$C_{15}$ aralkyloxy group and a heterocyclic group; an unsubstituted heterocyclic group such as, for example, a pyridyl group or a quinolyl group; a heterocyclic group having 1 to 5 substituents selected from the group consisting of a $C_1$–$C_5$ alkyl group, a halogen atom and a cyano group; or a $C_6$–$C_{12}$ aryl group having 1 to 5 substituents selected from the group consisting of a $C_1$–$C_5$ alkyl group, a halogen atom and a cyano group, etc. are suitable.

A compound of the invention represented by the general formula [I] can, for example, be prepared according to the following process.

For example, by using BE-49385A as a raw material, a compound wherein $Y^1$ is an oxygen atom and $R^1$ is a hydrogen atom, among compounds represented by the general formula [I], is first prepared, and by making chemical modification thereon according to necessity, a compound wherein $Y^1$ is NH and $R^1$ is a hydrogen atom is preferred.

A compound of the invention can be prepared by arranging reaction steps so that a bonding group represented by $Y^1$ can be formed when the hydrogen atom of such a compound or the like as an intermediate is replaced with a group corresponding to $R^1$.

In the occasion, it is preferred that a functional group not participating in the reaction is protected according to necessity, and the protective group used is removed after the reaction.

In introduction of such a substituent, it is possible to use an introduction method of a substituent well known in the field of chemistry, for example, a method called alkylation, alkenylation, alkynylation, aralkylation, alkanoylation, arylation, thiocarbonylation, sulfonation, cabamatation or carbamidation.

These terms are taken in the broad senses, and include all reactions whereby substituents corresponding to $R^1$ of the compounds of the general formula [I] of the invention are introduced, for example, alkanoylation means introduction of substituted or unsubstituted alkanoyl groups included in the invention.

Alkylation, alkenylation, alkynylation or aralkylation of a compound wherein $Y^1$ is an oxygen atom or NH and $R^1$ is a hydrogen atom can be carried out according to a method known per se, using an alkylating agent, an alkenylating agent, an alkynylating agent or an aralkylating agent such as, for example, an alkylhalide, an alkenyl halide, an alkynylhalide, an aralkyl halide, an alkyl mesylate, an alkenyl mesylate, an aralkyl mesylate, an alkyl tosylate or an aralkyl tosylate.

Alkylation, alkenylation, alkynylation or aralkylation of a compound wherein $Y^1$ is an oxygen atom or NH and $R^1$ is a hydrogen atom can be carried out by making an alkylating agent, an alkenylating agent, an alkynylating agent or an aralkylating agent act on a compound wherein $Y^1$ is an oxygen atom or NH and $R^1$ is a hydrogen atom, in a suitable solvent.

As the solvent, there can be mentioned dimethylformamide, methylene chloride or dimethylsulfoxide or a mixed solvent thereof, etc.

The reaction temperature can be a temperature in the range of about −20° C. to the boiling point of the solvent, and if necessary, can be a temperature lower than that, but is preferably 2° C. to 60° C.

The reaction time can, usually, be 10 minutes to 24 hours, and if necessary, can be longer or shorter than that, but is preferably 1 hour to 12 hours.

The use amount of the alkylating agent, an alkenylating agent, an alkynylating agent or an aralkylating agent to a compound wherein $Y^1$ is an oxygen atom or NH and $R^1$ is a hydrogen atom, is not particularly limited, and can be varied over a wide range depending on the kind of the compound, the reaction condition, etc., but is usually at least 1 mole, preferably 1 to 10 moles, more preferably 2 to 5 moles per mole of a compound wherein $Y^1$ is an oxygen atom or NH and $R^1$ is a hydrogen atom.

Alkanoylaion or alkylthiocarbonylaion of a compound wherein $Y^1$ is an oxygen atom or NH and $R^1$ is a hydrogen atom can be carried out by making an acid halide, an acid anhydride or the like corresponding to the objective substituent act on a compound wherein $Y^1$ is an oxygen atom or NH and $R^1$ is a hydrogen atom, n a suitable solvent.

As the solvent, there can be mentioned dimethylformamide, pyridine, methylene chloride or dimehtylsulfoxide or a mixed solvent thereof, etc.

The reaction temperature can be a temperature in the range of about −5° C. to the boiling point of the solvent, and if necessary, can be a temperature lower than that, but is preferably 20° C. to 60° C.

The reaction time can, usually, be 30 minutes to 2 days, and if necessary, can be longer or shorter than that, but is preferably 1 hour to 24 hours.

The use amount of the acid halide, the acid anhydride or the like to a compound wherein $Y^1$ is an oxygen atom or NH and $R^1$ is a hydrogen atom, is not particularly limited, and can be varied over a wide range depending on the kind of the compound, the reaction condition, etc., but is usually at least 1 mole, preferably 1 to 5 moles, more preferably 1 to 3 moles per mole of a compound wherein $Y^1$ is an oxygen atom or NH and $R^1$ is a hydrogen atom.

Sulfonylaion of a compound wherein $Y^1$ is an oxygen atom or NH and $R^1$ is a hydrogen atom can be carried out by making an organic sulfonyl halide, an organic sulfonic acid anhydride or the like corresponding to the objective substituent act on a compound wherein $Y^1$ is an oxygen atom or NH and $R^1$ is a hydrogen atom, in a suitable solvent, in the presence or absence of a base.

As the solvent, there can be mentioned dimethylformamide, toluene, methylene chloride or dimehtylsulfoxide or a mixed solvent thereof, etc.

As the base, there can be mentioned sodium hydride, lithium hydride, etc.

The reaction temperature can be a temperature in the range of about −10° C. to about 50° C., and if necessary, can be a temperature lower than that, but is preferably 20° C. to 60° C.

The reaction time can, usually, be 30 minutes to 3 days, and if necessary, can be longer or shorter than that, but is preferably 1 hour to 24 hours.

The use amount of the organic sulfonyl halide, the organic sulfonic acid anhydride or the like to a compound wherein $Y^1$ is an oxygen atom or NH and $R^1$ is a hydrogen atom, is not particularly limited, and can be varied over a wide range depending on the kind of the compound, the reaction condition, etc., but is usually a small excess amount per mole of a compound wherein $Y^1$ is an oxygen atom or NH and $R^1$ is a hydrogen atom, and if necessary can be an amount more than or less than that, but preferably, the use amount is 1 mole to 3 moles per mole of the compound.

Carbamatation or carbamidaion of a compound wherein $Y^1$ is an oxygen atom or NH and $R^1$ is a hydrogen atom can be carried out by making an organic isocyanate or the like corresponding to the objective substituent act on a compound wherein $Y^1$ is an oxygen atom or NH and $R^1$ is a hydrogen atom, in a suitable solvent, in the presence or absence of a catalyst.

As the solvent, there can be mentioned dimethylformamide, toluene, methylene chloride or dimehtylsulfoxide or a mixed solvent thereof, etc.

As the catalyst, there can be mentioned dibutyltin diacetate, etc.

The reaction temperature can be a temperature in the range of about −10° C. to about 50° C., and if necessary, can be a temperature lower than that, but is preferably 20° C. to 60° C.

The reaction time can, usually, be 30 minutes to 3 days, and if necessary, can be longer or shorter than that, but is preferably 1 hour to 24 hours.

The use amount of the organic isocyanate or the like to a compound wherein $Y^1$ is an oxygen atom or NH and $R^1$ is a hydrogen atom, is not particularly limited, and can be varied over a wide range depending on the kind of the compound, the reaction condition, etc., but is usually a small excess amount per mole of a compound wherein $Y^1$ is an oxygen atom or NH and $R^1$ is a hydrogen atom, and if necessary can be an amount more than or less than that, but preferably, the use amount is 1 mole to 3 moles per mole of the compound.

In the above-mentioned methods, as protective groups for functional groups not participating in the reactions, there can be mentioned the above-mentioned, protective groups of a hydroxyl group, protective groups of an amino group and protective groups of a carboxyl group, or ones acting similarly.

Introduction and removal of the protective groups can be carried out using any usual methods widely known in the field of chemistry, such as, for example, methods described in literatures [see Protective Groups in Organic Synthesis, written by T. W. Greene, John Wiley & Sons Co. (1981)] or methods similar thereto.

Isolation and purification of compounds formed by the above reactions can be carried out by methods known per se in the field of organic chemistry, for example, a precipitation method, a solvent extraction method, recrystallization, chromatography, etc.

Compounds obtained by the above-mentioned reactions can be converted into pharmacologically acceptable salts or esters according to conventional methods, and conversely, conversion from salts or esters into free compounds can also be carried out by conventional methods.

BE-49385A as a raw material can be prepared, using, for example, *Paecilomyces inflatus* F49385 or a mutant thereof excellent in productivity of the compound, as described in a international publication No. WO97/19186.

*Paecilomyces inflatus* F49385 has the following microbiological characteristics 1. Morphological Characteristics Mycelia of F49385 strain are colorless, have smooth surfaces, and are 0.8 to 2.4 μm in width. Conidiophores are occasionally formed, and when formed, the length is 5.6 to 6.4 μm and the width of the basal part is 2.0 to 2.4 μm. Phialides are formed directly on the mycelia or formed at the tip parts of the conidiophores, and are flask-shaped and 5.6–15.2×2.4–3.2 μm in size, and the tips are long and thin and 0.8 μm in width. Conidia are formed in a chain state from the tips of the phialides, lemon-shaped and 2.8–4.8× 2.4–2.8 μm in size, and have smooth surfaces, and both ends thereof are rectangular and 0.4 μm in width.

2. Characteristics in Culture

Characteristics in growth in the case of culture at 25° C. for 10 days in various agar media are shown in the following Table 1. Colors in the table were expressed according to color names described in Methuen Handbook of color, third edition, 1984.

In each of the media, growth is comparatively slow and secretion is not observed on the surface of the colony. The strain does not grow at 37° C. The growth temperature range of the strain is 11to 34° C. and the optimum growth temperature is 28° C., and the growth hydrogen ion concentration range is a pH of 3.5 to 9 and the optimum growth hydrogen ion concentration is 4.5 to 6.5. From the foregoing results, F49385 strain was identified as *Paecilomyces inflatus,* and designated *Paecilomyces inflatus* F49385. This strain was deposited as an international deposit with National Institute of Bioscience and Human Technology, Agency of Industrial Science and Technology, the Ministry of International Trade and Industry, JAPAN [Post office address: 1-3, Higashi 1-chome, Tsukubashi, Ibaraki, JAPAN (Postal code 305-0046), and the accession number is FERM BP-5715 [Deposit date: Nov. 8, 1995].

The compounds of the general formula [I] provided by the invention show excellent antifungal activities, as exemplified in the following biological activities. Antifungal activities on fungi, namely minimum growth inhibition concentrations (MICs) are shown in Table 2.

TABLE 1

Characteristics of F49385

| Medium | Colony diameter (mm) | Colony color | Reverse coloration | Colony texture |
| --- | --- | --- | --- | --- |
| Czapek's agar | 12–13 | white to grayish white | white | plane, thin |
| Potato dextrose agar | 19–20 | white to pale yellowish white | gray | velvety to powdery with radial sulcate |
| Potato - carrot agar | 22–24 | white to pale yellowish white | pale yellowish white | cottony with radial sulcate |

TABLE 2

Biological activities of BE - 49385 derivatives (antifungal activities)

| Compound number[a] | MIC (μg/ml)[b] |
| --- | --- |
| Compound 5 | 6.25 |
| Compound 9 | 6.25 |
| Compound 14 | 12.5 |
| Compound 23 | 12.5 |
| Compound 26 | 3.13 |
| Compound 31 | 12.5 |
| Compound 32 | 6.25 |
| Compound 33 | 6.25 |
| Compound 39 | 3.13 |
| Compound 40 | 6.25 |
| Compound 42 | 12.5 |
| Compound 43 | 3.13 |
| Compound 46 | 12.5 |
| Compound 54 | 12.5 |
| Compound 64 | 6.25 |
| Compound 65 | 6.25 |

[a]The minimum growth inhibition concentrations (MICs) of BE-49385 A alone and amphotericin B alone under this experimental condition were 100 μg/ml or more, respectively.
[b]MIC was judged after culture of at 37° C. for 2 days, according to the agar plate dilution method using *Trichosporon cutaneum* IFO 1189 as a test fungus and an agar plate prepared by adding 1% glucose, 0./25% dipotassium hydrogenphosphate and 1.2% agar to the yeast-nitrogen base made by Difco Laboratories.

The compounds of the invention are compounds obtained by chemically modifying BE-49385 A and different from BE-49385 A in structure, and have antifungal activities on fungi against which BE-49385 A does not show an antifungal activity. Therefore, the compounds are extremely useful as antifungal agents.

A compound or an antifungal composition of the invention, in its clinical use, can be orally or parenterally administered, and can be provided as an antifungal agent by adding thereto pharmaceutically acceptable various additives according to necessity and formulating the mixture so as to conform to its administration form.

As dosage forms in formulation, there can be mentioned solid preparations such as, for example, tablets, capsules, granules, pills, troches, powders or suppositories, liquid preparations such as, for example, syrups, elixirs, suspensions or injections, and moreover, aerosols, eye drops, ointments, eye ointments, emulsions, creams, liniments, lotions, etc., and these can be prepared according to usual methods in the pharmaceutical field.

As the additives, various additives usually used in the pharmaceutical field can be used, and there can be mentioned a sugar such as, for example, lactose or glucose, a starch such as, for example, corn, wheat or rice, a vegetable oil such as, for example, soybean oil, peanut oil or sesame oil, a fatty acid such as, for example, stearic acid, an inorganic salt such as, for example, magnesium metasilicate aluminate or anhydrous calcium phosphate, a synthetic macromolecule such as, for example, polyvinylpyrrolidone or polyalkylene glycol, a fatty acid salt such as, for example, calcium stearate or magnesium stearate, an alcohol such as, for example, stearyl alcohol or benzyl alcohol, a synthetic cellulose derivative such as, for example, methylcellulose, carboxymethylcellulose, ethyl-cellulose or hydroxypropylmethylcellulose, and in addition, water, gelatin, talc, gum arabic, etc.

In the case of liquid preparation, it can be a form wherein it is dissolved or suspended in water or another suitable medium in use. Especially when it is administered by intramuscular injection, intravenous injection, subcutaneous injection or the like, as suitable media for the injections, there can, for example, be mentioned distilled water for injection, an aqueous lidocaine hydrochloride solution (for intramuscular injection), physiological saline, an aqueous glucose solution, ethanol, liquids for intravenous injection (e.g., an aqueous solution of citric acid and sodium citrate, etc.), electrolyte solutions (for drip-feed intravenous injection and for intravenous injection), etc., or mixed solutions thereof, and furthermore a buffer or a preservative can also be added. When such a preparation is the above-mentioned solid preparation, it can contain usually 0.1 to 100% by weight, preferably 5 to 100% by weight of an effective ingredient, and in the case of another preparation, it can contain 0.1 to 10% by weight, preferably 1 to 5% by weight of an effective ingredient.

An actually preferred dose of the compound or antifungal composition of the invention is varied depending on the kind of the compound to be used, the kind of the composition to be compounded, and the distinction of sex, age, weight, the degree of the symptom and the particular site to be treated, of the patient, etc., but is generally, per day on an adult, 0.1 to 100 mg/kg in the case of oral administration, and 0.01 to 100 mg/kg in the case of parenteral administration. The number of times of administration is varied depending on the administration method and the symptom, but it is preferred to administer it in divisions of 1 to 5 times per day.

As stated above, according to the invention, it is possible to provide a useful antifungal agent, and it goes without saying that it is also possible to provide a novel treatment method for infectious diseases caused by fungi, using it.

EXAMPLE

The invention is specifically described below according to examples, preparation examples and a reference example.

In the following examples, BE-49385 A obtained in the reference example is referred to as Compound (1), and the meanings of abbreviations in NMR measurement are set forth below.

s: singlet d: doublet t: triplet q: quartet m: multiplet br: broad

J: coupling constant

Hz: hertz

Example 1

Preparation of 1,10,13a-trihydroxy-11-isopropyl-4,
7,8a-trimethyl-13-methylene-2-oxo-1,2,4,4a,5,7a,8,
8a,9,10,11,11a,12,12a,13,13α-hexadecahydroindeno
[5',6':4,5]cycloocta[1,2-c]pyrane [Compound (2)]

Compound (1) (1.39 g) was dissolved in 100 ml of acetone, and 500 ml of 0.1 M morphonyl propylsulfonate buffer (pH 6.5) in which 500 mg of an esterase derived from porcine liver was dissolved in advance was added. The mixture was incubated at 37° C. for 16 hours, and 1 L of methyl ethyl ketone was added twice. The methyl ethyl ketone layer was concentrated to dryness under reduced pressure, and the residue was dissolved in 50% acetonitrile. The solution was charged onto a silica gel column (made by FUJI SILYSIA CHEMICAL LTD., Chromatorex ODS DM2035M, 4.0φ×30 cm) for reverse-phase column chromatography, and elution was made with 50%, 60% and 70% acetonitrile in this order, and fractions containing the objective substance were concentrated to obtain 873.2 mg of Compound (2).

Rf value; 0.30 [Kieselgel 60$F_{254}$ made by Merck & Co., Inc. was used; developing solvent: n-hexane-ethyl acetate (1:2)]

Mass analysis; [FAB-MS] m/z: 419 (M+H)$^+$

Nuclear magnetic resonance spectrum;

$^1$H-NMR(δ ppm,400 MHz,CDCl$_3$): 5.14(1H,d,J=1.0 Hz) ,5.04(1H,t,J=8.8 Hz),4.70(1H,s),4.42–4.34(2H,m),4.22(1H, d,J=3.9 Hz),3.17–3.06(3H,m),2.89(1H,s),2.19(1H,t,J=12.7 Hz),2.08–2.02 (3H,m),1.98–1.90(2H,m),1.81(1H,dt,J=12.7 Hz,J=3.4 Hz),1.67(1H,m),1.63(3H,s),1.51(1H,m),1.46(3H, d,J=6.4 Hz),1.34(1H,q,J=12.7 Hz),1.23(1H,dd,J=10.3 Hz,3.4 Hz),1.09(1H,t,J=12.7 Hz),1.00(3H,d,J=6.4 Hz),0.96 (3H,d,J=6.4 Hz),0.93(3H,s)

Example 2

Preparation of 13a-hydroxy-11-isopropyl-4,7,8a-trimethyl-13-methylene-1-(tetrahydro-2H-pyran-2-yloxy) -4,4a,5,7a,8,8a,9,10,11,11a,12,12a,13,13a-hexadecahydroindeno[5',61': 4,5]cycloocta[1,2-c] pyran-10-yl-3-hydroxy-3,5-dimethylheptanoate [Compound (3)]

Compound (1) (100 mg) was dissolved in 1.0 ml of dichloromethane, and 48.2 mg of pyridinium-p-toluenesulfonate and 17.5 μl of 3,4-dihydro-2H-pyrane were added, and the mixture was stirred at room temperature. 17 hours thereafter, for making the reaction progress, 6.4 μl of 3,4-dihydro-2H-pyrane was added, and the mixture was stirred for further 4 hours.

The reaction mixture was charged as such onto silica gel column (Kieselgel 60 made by Merck & Co., Inc., 1.5φ×30 cm), and developed with n-hexane-ethyl acetate (4:1). Fractions containing the objective substance were concentrated under reduced pressure to obtain 52.6 mg of Compound (3).

Rf value; 0.40 [Kieselgel 60$F_{254}$ made by Merck & Co., Inc. was used; developing solvent: n-hexane-ethyl acetate (2:1)]

Mass analysis; [FAB-MS] m/z: 659 (M+H)$^+$

Nuclear magnetic resonance spectrum;

$^1$H-NMR(δ ppm,400 MHz,CDCl$_3$): 5.30(1H,td,J=7.8 Hz,3.4 Hz),5.11(1H,s),5.03(1H,t,J=7.8 Hz),4.76(1H,s),4.65 (1H,dd,J=6.8 Hz,2.0 Hz),4.44(1H,s),4.33(1H,dq,10.7 Hz,6.4 Hz),4.15(1H,s),4.00(1H,dt,J=11.2 Hz,3.9 Hz),3.60 (1H,s),3.54(1H,td,J=8.3 Hz,2.9 Hz),3.16–3.04(2H,m),2.49 (1H,d,J=15.6 Hz),2.39(1H,d,J=15.6 Hz),2.27–2.17(2H,m), 2.04–1.68(9H,m),1.62(3H,s),1.56–1.45(5H,m),1.42(3H,d, J=6.4 Hz),1.40–1.30(3H,m),1.23(3H,s),1.21–1.12(2H,m), 1.05(1H,t,J=12.7 Hz),0.97(3H,s),0.94–0.85(12H,m)

Example 3

Preparation of 10,13a-dihydroxy-11-isopropyl-4,7,
8a-trimethyl-13-methylene-1-(tetrahydro-2H-pyran-
2-yloxy)-4,4a,5,7a,8,8a,9,10,11,11a,12,12a,13,13a-
hexadecahydroindeno[5',6':4,5]cycloocta[1,2-c]
pyran-2(1H)-one [Compound (4)]

Ten ml of 0.1 M morphonyl propylsulfonate buffer (pH 6.5) prepared in advance and 10 mg of an esterase derived from porcine liver were mixed, and 10 mg of Compound (3) dissolved in 1.0 ml of acetone was added, and the mixture was subjected to reaction at 37° C. for 16 hours.

After the reaction, 20 ml of methyl ethyl ketone and 10 ml of water were added to make extraction, and the obtained methyl ethyl ketone layer was concentrated under reduced pressure. The resulting residue was charged onto silica gel column (Kieselgel 60 made by Merck & Co., Inc., 1.5φ×30 cm), and developed with n-hexane-ethyl acetate (1:1). Fractions containing the objective substance were concentrated under reduced pressure to obtain 7.0 mg of Compound (4).

Rf value; 0.28 [Kieselgel 60$F_{254}$ made by Merck & Co., Inc. was used; developing solvent: n-hexane-ethyl acetate (1:1)]

Mass analysis; [FAB-MS] m/z: 503 (M+H)$^+$

Nuclear magnetic resonance spectrum;

$^1$H-NMR(δ ppm,400 MHz,CDCl$_3$): 5.10 (1H,d,J=1.0 Hz), 5.03(1H,t,J=8.8 Hz),4.75(1H,s),4.66(1H,dd,J=6.8 Hz,2.4 Hz),4.42 (1H,s),4.33(2H,brdq,10.7 Hz,6.3 Hz),4.15(1H,s), 3.99(1H,m),3.52(1H,m),3.15(1H,dd,J=13.2 Hz,8.8 Hz),3.07 (1H,td,J=8.8 Hz,3.4 Hz),2.19 (1H,td,J=12.2 Hz,2.9 Hz), 2.07–2.01(2H,m),1.98–1.89(4H,m),1.88–1.81(2H,m), 1.70–1.45(9H,m),1.42(3H,d,J=6.3 Hz),1.29(1H,q,J=11.2 Hz),1.21(1H,dd,J=11.2 Hz,9.3 Hz),1.07(1H,t,J=12.2 Hz), 1.00(3H,d,J=6.3 Hz),0.94(3H,d,J=6.3 Hz),0.92(3H,s)

Example 4

Preparation of 1,13a-dihydroxy-11-isopropyl-4,7,8a-
trimethyl-13-methylene-2-oxo-1,2,4,4a,5,7a,8,8a,9,
10,11,11a,12,12a,13,13a-hexadecahydroindeno[5',
6':4,5]cycloocta [1,2-c]pyran-10-yl butanoate
[Compound (5)]

Compound (2) (30 mg) was dissolved in 1.0 ml of dry pyridine, 14.1 μl of n-butyric anhydride and 10.5 mg of dimethylaminopyridine were added, and the mixture was stirred at room temperature. For making the reaction progress, after 3.5 hours, 9.1 μl of n-butyric anhydride was added, and the mixture was stirred for further 1.5 hours. The reaction mixture was concentrated under reduced pressure, and the concentrate was charged onto silica gel column (Kieselgel 60 made by Merck & Co., Inc., 1.5φ×30 cm), and developed with n-hexane-ethyl acetate (2:1). Fractions containing the objective substance were concentrated under reduced pressure to obtain 10.1 mg of Compound (5).

Rf value; 0.44 [Kieselgel 60$F_{254}$ made by Merck & Co., Inc. was used; developing solvent: n-hexane-ethyl acetate (1:1)]

Mass analysis; [FAB-MS] m/z: 489 (M+H)$^+$

Nuclear magnetic resonance spectrum;

$^1$H-NMR (δ ppm,400 MHz,CDCl$_3$): 5.23(1H,td,J=7.8 Hz,3.9 Hz),5.14(1H,d,J=1.0 Hz),5.03(1H,t,J=8.8 Hz),4.70 (1H,s),4.38(1H,dq,10.7 Hz,6.4 Hz),4.21(1H,s),3.16–3.05 (2H,m),2.25–2.16(4H,m),2.06–1.90(4H,m),1.83(1H,dt,J= 13.2 Hz,3.4 Hz),1.78–1.59(7H,m),1.45(3H,d,J=6.4 Hz), 1.36(1 H,q,J=12.7 Hz),1.12(1H,dd,J=11.7 Hz,8.3 Hz),1.08(1 H,t,J=12.7 Hz),0.97–0.92(9H,m),0.87(3H,d,J=5.9Hz)

Example 5

Preparation of 1,13a-dihydroxy-11-isopropyl-4,7,8a-trimethyl-13-methylene-2-oxo-1,2,4,4a,5,7a,8,8a,9, 10,11,11a,12,12a,13,13a-hexadecahydroindeno[5', 6':4,5]cycloocta [1,2-c]pyran-10-yl pentanoate [Compound (6)]

Compound (2) (100 mg) was dissolved in 1.2 ml of dry dimethylformamide, and 56.7 μl of valeric anhydride and 87.5 mg of dimethylaminopyridine were added, and the mixture was stirred at room temperature for 20 hours. The reaction mixture was cocentrated under reduced pressure, and the cocentrate was charged onto silica gel column (Kieselgel 60 made by Merck & Co., Inc., 1.5φ×23 cm), and developed with n-hexane-ethyl acetate (2:1). Fractions containing the objective substance were concentrated under reduced pressure to obtain 8.0 mg of Compound (6).

Rf value; 0.52 [Kieselgel 60F$_{254}$ made by Merck & Co., Inc. was used; developing solvent: n-hexane-ethyl acetate (1:1)]

Mass analysis; [FAB-MS] m/z: 503 (M+H)$^+$

Nuclear magnetic resonance spectrum;

$^1$H-NMR (δ ppm,200 MHz,CDCl$_3$): 5.22(1H,td,J=7.8 Hz,3.9 Hz),5.13(1H,d,J=1.0 Hz),5.03(1H,t,8.8 Hz),4.70(1H, s),4.38(1H,dq,J=10.7 Hz,6.4 Hz),4.22(1H,s),3.15–3.00(2H, m),2.35–2.15(4H,m),2.05–1.90(4H,m),1.85–1.50(8H,m), 1.45(3H,d,J=6.4 Hz),1.43–1.20(4H,m),1.08(1H,t,J=12.7 Hz),0.98–0.86(12H,m)

Example 6

Preparation of 1,13a-dihydroxy-11-isopropyl-4,7,8a-trimethyl-13-methylene-2-oxo-1,2,4,4a,5,7a,8,8a,9, 10,11,11a,12,12a,13,13a-hexadecahydroindeno[5', 6':4,5]cycloocta [1,2-c]pyran-10-yl hexanoate [Compound (7)]

Compound (2) (40 mg) was dissolved in 1.0 ml of dry pyridine, and 31.0 μl of n-hexanoic anhydride was added, and the mixture was stirred at room temperature. For making the reaction progress, 2 hours later, 62.0 μl of n-hexanoic anhydride was added, and further 21 hours later, 62.0 μl of n-hexanoic anhydride was added, and the mixture was stirred for further 3 hours. The reaction mixture was concentrated under reduced pressure, and the concentrate was charged onto silica gel column (Kieselgel 60 made by Merck & Co., Inc., 1.5φ×25 cm), and developed with n-hexane-ethyl acetate (3:1). Fractions containing the objective substance were concentrated under reduced pressure to obtain the objective substance in a crude state. For further purification, the crude substance was subjected to reverse-phase chromatography [Chromatorex ODS made by FUJI SILYSIA CHEMICAL LTD., 2.0φ×25 cm, water-acetonitrile (1:9), 10.0 ml/min], and fractions containing the objective substance were concentrated under reduced pressure to obtain 14.8 mg of Compound (7).

Rf value; 0.25 [Kieselgel 60F$_{254}$ made by Merck & Co., Inc. was used; developing solvent: n-hexane-ethyl acetate (2:1)]

Mass analysis; [FAB-MS] m/z: 517 (M+H)$^+$

Nuclear magnetic resonance spectrum;

$^1$H-NMR(δ ppm,400 MHz,CDCl$_3$): 5.23(1H,td,J=7.8 Hz,3.9 Hz),5.14(1H,d,J=1.0 Hz),5.04(1H,t,J=9.3 Hz),4.71 (1H,s),4.38(1H,dq,10.7 Hz,6.4 Hz),4.22(1H,s),3.16–3.05 (3H,m),2.84(1H,brs),2.26–2.16(4H,m),2.06–1.91(4H,m), 1.82(1H,dt,J=12.7 Hz,3.4 Hz),1.78–1.67(2H,m),1.63(3H,s), 1.60(2H,m),1.46(3H,d, J=6.4 Hz),1.37(1H,q,J=12.7 Hz), 1.33–1.25(4H,m),1.15–1.04(2H,m),0.97(3H,s),0.93(3H,d, J=5.9 Hz),0.89(3H,t,J=6.8 Hz),0.88(3H,d,J=5.9 Hz)

Example 7

Preparation of 1,13a-dihydroxy-11-isopropyl-4,7,8a-trimethyl-13-methylene-2-oxo-1,2,4,4a,5,7a,8,8a,9, 10,11,11, 11a,12,12a,13,13a-hexadecahydroindeno [5',6':4,5]cycloocta [1,2-c]pyran-10-yl heptanoate [Compound (8)]

Compound (2) (30 mg) was dissolved in 1.0 ml of dry pyridine, and 26.4 μl of n-heptanoic anhydride was added, and the mixture was stirred at room temperature. For making the reaction progress, 5 hours later, 26.4 μl of n-heptanoic anhydride was added, and further 18 hours later, 26.4 μl of n-heptanoic anhydride was added, and the mixture was stirred for further 8 hours. The reaction mixture was concentrated under reduced pressure, and the concentrate was charged onto silica gel column (Kieselgel 60 made by Merck & Co., Inc., 1.5φ×25 cm), and developed with n-hexane-ethyl acetate (2:1). Fractions containing the objective substance were concentrated under reduced pressure to obtain the objective substance in a crude state. For further purification, the crude substance was subjected to reverse-phase chromatography [Chromatorex ODS made by FUJI SILYSIA CHEMICAL LTD., 2.0φ×25 cm, water-acetonitrile (1:9), 10.0 ml/min], and fractions containing the objective substance were concentrated under reduced pressure to obtain 16.2 mg of Compound (8).

Rf value; 0.31 [Kieselgel 60F$_{254}$ made by Merck & Co., Inc. was used; developing solvent: n-hexane-ethyl acetate (2:1)]

Mass analysis; [FAB-MS] m/z: 531 (M+H)$^+$

Nuclear magnetic resonance spectrum;

$^1$H-NMR(δ ppm,400 MHz,CDCl$_3$): 5.23(1H,td, J=7.8 Hz,3.9 Hz),5.14(1H,d,J=1.0 Hz),5.04(1H,t,J=9.3 Hz),4.71 (1H,s),4.38(1H,dq,J=11.2 Hz,6.4 Hz),4.22(1H,s),3.16–3.05 (3H,m),2.81(1H,brs),2.27–2.17(4H,m),2.07–1.91(4H,m), 1.82(1H,dt,J=12.7 Hz,3.4 Hz),1.78–1.65(2H,m),1.63(3H,s), 1.60(2H,m),1.46(3H,d,J=6.4 Hz),1.37(1H,q,J=12.7 Hz), 1.32–1.25(6H,m), 1.15–1.04(2H,m),0.97(3H,s),0.93(3H,d, J=5.9 Hz),0.88(6H,m)

Example 8

Preparation of 1,13a-dihydroxy-11-isopropyl-4,7,8a-trimethyl-13-methylene-2-oxo-1,2,4,4a,5,7a,8,8a,9, 10,11,11a,12,12a,13,13a-hexadecahydroindeno[5', 6':4,5]cycloocta [1,2-c]pyran-10-yl 3-methylbutanoate [Compound (9)]

Compound (2) (30 mg) was dissolved in 1.0 ml of dry pyridine, and 17.1 μl of isovaleric anhydride and 10.5 mg of dimethylaminopyridine were added, and the mixture was stirred at room temperature. For making the reaction progress, 3.0 hours later, 11.4 μl of isovaleric anhydride was added, and the mixture was stirred for further 3 hours. The reaction mixture was concentrated under reduced pressure, and the concentrate was charged onto silica gel column (Kieselgel 60 made by Merck & Co., Inc., 1.5φ×30 cm), and developed with n-hexane-ethyl acetate (3:1). Fractions containing the objective substance were concentrated under reduced pressure to obtain 9.0 mg of Compound (9).

Rf value; 0.41 [Kieselgel 60F$_{254}$ made by Merck & Co., Inc. was used; developing solvent: n-hexane-ethyl acetate (1:1)]

Mass analysis; [FAB-MS] m/z: 503 (M+H)$^+$

Nuclear magnetic resonance spectrum;

$^1$H-NMR(δ ppm,400 MHz,CDCl$_3$): 5.23(1H,dt,J=7.8 Hz,3.4 Hz),5.14(1H,d,J=1.5 Hz),5.03(1H,t,J=8.8 Hz),4.70 (1H,s),4.38(1H,dq,10.8 Hz,6.4 Hz),4.21(1H,s),3.15–3.05 (2H,m),2.24(1H,dd,J=11.7 Hz,7.3 Hz),2.19(1H,dt,J=11.7 Hz,2.0 Hz),2.15–1.90(6H,m),1.83(1H,dt,J=13.2,3.4 Hz), 1.78–1.66(3H,m),1.63(3H,s),1.46(3H,d,J=6.4 Hz),1.36(1H, q,J=13.2 Hz),1.12(1H,dd,J=10.8 Hz,7.3 Hz),1.07(1H,t,J= 11.7 Hz),0.97(3H,s),0.94(6 H,d,J=6.4 Hz),0.93(3H,d,J=6.4 Hz),0.88(3H,d,J=6.4 Hz)

Example 9

Preparation of 1,13a-dihydroxy-11-isopropyl-4,7,8a-trimethyl-13-methylene-2-oxo-1,2,4,4a,5,7a,8,8a,9,10,11,11a,12,12a,13,13a-hexadecahydroindeno[5',64':4,5]cycloocta [1,2-c]pyran-10-yl crotonate [Compound (10)]

Compound (2) (30 mg) was dissolved in 1.0 ml of dry pyridine, and 12.8 μl of crotonic anhydride and 8.3 mg of dimethylaminopyridine were added, and the mixture was stirred at room temperature. For making the reaction progress, the reaction, 6 hours later, 11.4 μl of crotonic anhydride was added, and the mixture was stirred for further 12 hours. The reaction mixture was concentrated under reduced pressure, and the concentrate was charged onto silica gel column (Kieselgel 60 made by Merck & Co., Inc., 1.5φ×30 cm), and developed with n-hexane-ethyl acetate (2:1). Fractions containing the objective substance were concentrated under reduced pressure to obtain 8.7 mg of Compound (10).

Rf value; 0.43 [Kieselgel 60F$_{254}$ made by Merck & Co., Inc. was used; developing solvent: n-hexane-ethyl acetate (1:1)]

Mass analysis; [FAB-MS] m/z: 487 (M+H)$^+$

Nuclear magnetic resonance spectrum;

$^1$H-NMR(δ ppm,400 MHz,CDCl$_3$): 6.94(1H,dq,J=15.6, 6.8 Hz),5.81(1H,dq,J=15.6,1.5 Hz),5.28(1H,td,J=7.8 Hz,3.9 Hz),5.14(1H,d,J=1.5 Hz),5.03(1H,t,J=8.8 Hz),4.71(1H,s), 4.38(1H,dq,J=11.2 Hz,6.4 Hz),4.22(1H,s),3.16–3.03(2H,m), 2.94(1H,brs),2.27–2.17(2H,m),2.06–1.90(4H,m),1.87(3H, dd,J=6.8 Hz,1.5 Hz),1.85–1.66(3H,m),1.63(3H,s),1.45(3H, d,J=6.4 Hz),1.37(1H,q,J=12.7 Hz),1.16(1H,dd,J=12.2 Hz,8.8 Hz),1.07(1H,t,J=12.2 Hz),0.98(3 H,s),0.93(3H,d,J= 6.4 Hz),0.88(3H,d,J=6.4 Hz)

Example 10

Preparation of 1,13a-dihydroxy-11-isopropyl-4,7,8a-trimethyl-13-methylene-2-oxo-1,2,4,4a,5,7a,8,8a,9,10,11,11a,12,12a,13,13a-hexadecahydroindeno[5',6':4,5]cycloocta [1,2-c]pyran-10-yl (2E,4E)-2,4-hexadienoate [Compound (11)]

Compound (4) (10 mg) was dissolved in 0.2 ml of dry dichloromethane, and 5.4 mg of dicyclohexylcarbodiimide, 3.1 mg of dimethylaminopyridine and 2.4 mg of 2,4-hexadienoic acid were added, and the mixture was stirred at room temperature for 18 hours. After the reaction, the reaction mixture was filtered, the filtrate was concentrated under reduced pressure, and the concentrate was charged onto silica gel column (Kieselgel 60 made by Merck & Co., Inc., 1.5φ×23 cm), and developed successively with n-hexane-ethyl acetate (8:1→6:1→4:1). Fractions containing the objective substance were concentrated under reduced pressure to obtain 11.1 mg of a residue.

The residue (10 mg) was dissolved in 0.4 ml of methanol, and 4.2 mg of p-toluenesulfonic acid hydrate was added, and the mixture was stirred at room temperature for an hour and a half. After the reaction, the reaction mixture was concentrated under reduced pressure, and the concentrate was charged onto silica gel column (Kieselgel 60 made by Merck & Co., Inc., 1.50φ×20 cm), and developed with n-hexane-ethyl acetate (2:1). Fractions containing the objective substance were concentrated under reduced pressure to obtain 4.0 mg of Compound (11).

Rf value; 0.69 [Kieselgel 60F$_{254}$ made by Merck & Co., Inc. was used; developing solvent: n-hexane-ethyl acetate (1:1)]

Mass analysis; [FAB-MS] m/z: 513 (M+H)$^+$

Nuclear magnetic resonance spectrum;

$^1$H-NMR(δ ppm,200 MHz,CDCl$_3$3): 7.20(1H,dd,J=14.4, 8.2),6.27–6.24(2H,m),5.73(1H,d,J=14.4 Hz),5.30(1H,td,J= 7.8 Hz,3.9 Hz),5.15(1H,s),5.02(1H,t,J=8.8 Hz),4.71(1H,s), 4.38(1H,dq,J=10.7 Hz,6.4 Hz),4.21(1H,d,J=4.8 Hz), 3.15–3.10(3H,m),2.81(1H,s),2.25–2.18(2H,m),2.05–1.90 (4H,m),1.85 (3H,d,J=4.8 Hz),1.81–1.65(3H,m),1.63(3H,s), 1.45(3H,d,J=6.4 Hz),1.35–1.15(2H,m),1.08(1H,t,J=12.7 Hz),0.99(3H,s),0.92(3H,d,J=5.9 Hz),0.88(3H,d,J=5.9 Hz)

Example 11

Preparation of 1,13a-dihydroxy-11-isopropyl-4,7,8a-trimethyl-13-methylene-2-oxo-1,2,4,4a,5,7a,8,8a,9,10,11,11a,12,12a,13,13a-hexadecahydroindeno[5',6':4,5]cycloocta [1,2-c]pyran-10-yl 2-oxohexanoate [Compound (12)]

Compound (4) (20 mg) was dissolved in 2 ml of dry dichloromethane, and 10.6 mg of dicyclohexylcarbodiimide, 6.3 mg of dimethylaminopyridine and 5.7 mg of a-ketocaproic acid were added, and the mixture was stirred at room temperature. Two hours later, 10.6 mg of a-ketocaproic acid was further added. Two hours and a half later, the reaction mixture was concentrated under reduced pressure, and the concentrate was charged onto silica gel column (Kieselgel 60 made by Merck & Co., Inc., 1.5φ×25 cm), and developed successively with n-hexane-ethyl acetate (4:1→3:1). Fractions containing the objective substance were concentrated under reduced pressure to obtain 13 mg of a residue.

The residue (12.5 mg) was dissolved in 0.4 ml of methanol, and 4.2 mg of p-toluenesulfonic acid hydrate was added, and the mixture was stirred at room temperature for an hour and a half. After the reaction, the reaction mixture was concentrated under reduced pressure, and the concentrate was charged onto silica gel column (Kieselgel 60 made by Merck & Co., Inc., 1.50φ×20 cm), and developed with n-hexane-ethyl acetate (2:1). Fractions containing the objective substance were concentrated under reduced pressure to obtain 6.9 mg of Compound (12).

Rf value; 0.52 [Kieselgel 60F$_{254}$ made by Merck & Co., Inc. was used; developing solvent: n-hexane-ethyl acetate (1:1)]

Mass analysis; [FAB-MS] m/z: 531 (M+H)$^+$

Nuclear magnetic resonance spectrum;

$^1$H-NMR($\delta$ ppm,200 MHz, CDCl$_3$): 5.35(1H,td, J=7.8 Hz,3.9 Hz),5.14(1H,s),5.03(1H,t,J=8.8 Hz),4.71(1H,s),4.38 (1H,dq,J=10.8 Hz,6.4 Hz),4.22(1H,s),3.18–3.03(2H,m),2.79 (2H,t,J=6.4 Hz),2.28–1.52(14H,m),1.47(3H,d,J=6.4 Hz), 1.35–1.10(4H,m),1.08(1H,t,J=12.7 Hz),0.97–0.86(12H,m)

Example 12

Preparation of 1,13a-dihydroxy-11-isopropyl-4,7,8a-trimethyl-13-methylene-2-oxo-1,2,4,4a,5,7a,8,8a,9,10,11,11a,12,12a,13,13a-hexadecahydroindeno[5',6':4,5]cycloocta [1,2-c]pyran-10-yl 2-benzyloxyhexanoate [Compound (13)]

Compound (4) (30 mg) was dissolved in 1.0 ml of dry dichloromethane, and 12.4 mg of dicyclohexylcarbodiimide, 8.1 mg of dimethylaminopyridine and 14.6 mg of 2-benzyloxyhexanoic anhydride were added, and the mixture was stirred at room temperature for 1 hour. After the reaction, the reaction mixture was filtered, the filtrate was concentrated under reduced pressure, and the concentrate was charged onto silica gel column (Kieselgel 60 made by Merck & Co., Inc., 1.5$\phi$×30 cm), and developed with n-hexane-ethyl acetate (2:1). Fractions containing the objective substance were concentrated under reduced pressure to obtain 31 mg of a residue. The residue (28 mg) was dissolved in 2 ml of methanol, and 15.8 mg of p-toluenesulfonic acid hydrate was added, and the mixture was stirred at room temperature for 2 hours. After the reaction, the reaction mixture was concentrated under reduced pressure, and the concentrate was charged onto silica gel column (Kieselgel 60 made by Merck & Co., Inc., 1.5$\phi$×30 cm), and developed with n-hexane-ethyl acetate (1:1). Fractions containing the objective substance were concentrated under reduced pressure to obtain 23.0 mg of Compound (13).

Rf value; 0.31 [Kieselgel 60F$_{254}$ made by Merck & Co., Inc. was used; developing solvent: n-hexane-ethyl acetate (2:1)]

Mass analysis; [FAB-MS] m/z: 623 (M+H)$^+$

Nuclear magnetic resonance spectrum;

$^1$H-NMR($\delta$ ppm,400 MHz, CDCl$_3$): 7.34(4H,d,J=4.4 Hz), 7.29(1H,m),5.32(1H,dt,J=7.8 Hz,3.9 Hz),5.14(1H,s),5.04 (1H,t,J=8.8 Hz),4.71(1H,s),4.68(1H,dd,J=11.7 Hz,4.9 Hz), 4.40–4.36(2H,m),4.22(1H,s),3.87(1H,t,J=6.8 Hz),3.16–3.06 (3H,m),2.87(1H,brs),2.28(1H,ddd,J=16.6 Hz,12.2 Hz,7.3 Hz),2.20(1H,td,J=12.2 Hz,2.4 Hz),2.06–1.91(4H,m), 1.86–1.70(5H,m),1.63(3H,s),1.46(3H,d,J=6.4 Hz), 1.42–1.24(5H,m),1.19–1.05(2H,m),0.99(3H,s),0.94(3H,q, J=2.9 Hz),0.91–0.84(6H,m)

Example 13

Preparation of 1,13a-dihydroxy-11-isopropyl-4,7,8a-trimethyl-13-methylene-2-oxo-1,2,4,4a,5,7a,8,8a,9,10,11,11a,12,12a,13,13a-hexadecahydroindeno[5',6':4,5]cycloocta [1,2-c]pyran-10-yl 2-hydroxyhexanoate [Compound (14)]

Compound (13) (18 mg) was dissolved in 5 ml of methanol, and a catalytic amount of 10% palladium-carbon was added, and the mixture was stirred under a hydrogen atmosphere at room temperature for 2 hours. The reaction mixture was filtered, and the filtrate was concentrated under reduced pressure to obtain a crude product. The crude product was charged onto silica gel column (Kieselgel 60 made by Merck & Co., Inc., 1.5$\phi$×25 cm), and developed with n-hexane-ethyl acetate (2:1). Fractions containing the objective substance were concentrated under reduced pressure to obtain 14.8 mg of Compound (14).

Rf value; 0.48 [Kieselgel 60F$_{254}$ made by Merck & Co., Inc. was used; developing solvent: n-hexane-ethyl acetate (1:1)]

Mass analysis; [FAB-MS] m/z: 533 (M+H)$^+$

Nuclear magnetic resonance spectrum;

$^1$H-NMR($\delta$ ppm,400 MHz, CDCl$_3$): 5.31(1H,dtd,J=11.7 Hz,7.8 Hz,3.9 Hz),5.14(1H,s),5.04(1H,t,J=9.3 Hz),4.71(1H, s),4.38(1H,dq,J=10.7 Hz,6.4 Hz),4.22(1H,s),4.12(1H,m), 3.16–3.06(3H,m),2.81(1H,brs),2.72(1H,brs),2.30–2.17(2H, m),2.07–1.91(4H,m),1.86–1.67(5H,m),1.63(3H,s),1.46(3H, d,J=6.4 Hz),1.44–1.24(5H,m),1.21–1.00(2H,m),0.99(3H,s), 0.94(3H,d,J=6.4 Hz),0.93–0.87(6H,m)

Example 14

Preparation of 1,13a-dihydroxy-11-isopropyl-4,7,8a-trimethyl-13-methylene-2-oxo-1,2,4,4a,5,7a,8,8a,9,10,11,11 a,12,12a,13,13a-hexadecahydroindeno[5',6':4,5]cycloocta [1,2-c]pyran-10yl 4-ethylbenzoate [Compound (15)]

Compound (4) (20 mg) was dissolved in 2 ml of dry dichloromethane, and 10.6 mg of dicyclohexylcarbodiimide, 6.3 mg of dimethylaminopyridine and 7.7 mg of 4-ethylbenzoic acid were added, and the mixture was stirred at room temperature. After 19 hours and a half, the reaction mixture was concentrated under reduced pressure, and the concentrate was charged onto silica gel column (Kieselgel 60 made by Merck & Co., Inc., 1.5$\phi$×23 cm), and developed successively with n-hexane-ethyl acetate (8:1, 7:1, 6:1, 5:1, 4:1). Fractions containing the objective substance were concentrated under reduced pressure to obtain 6.1 mg of a residue.

The residue (6.0 mg) was dissolved in 0.8 ml of methanol, and 1.8 mg of p-toluenesulfonic acid hydrate was added, and the mixture was stirred at room temperature for 15 hours and a half. After the reaction, the reaction mixture was concentrated under reduced pressure, and the concentrate was charged onto silica gel column (Kieselgel 60 made by Merck & Co., Inc., 1.5$\phi$×20 cm), and developed with n-hexane-ethyl acetate (4:1). Fractions containing the objective substance were concentrated under reduced pressure to obtain 5.0 mg of Compound (15).

Rf value; 0.31 [Kieselgel 60F$_{254}$ made by Merck & Co., Inc. was used; developing solvent: n-hexane-ethyl acetate (2:1)]

Mass analysis; [FAB-MS] m/z: 551 (M+H)$^+$

Nuclear magnetic resonance spectrum;

$^1$H-NMR($\delta$ ppm,400 MHz, CDCl$_3$): 7.94(2H,d,J=4.0 Hz), 7.26(2H,d, J=7.8 Hz),5.46(1H,td,J=7.8,3.9 Hz),5.17(1H,s), 5.04(1H,t,J=8.8 Hz),4.72(1H,s),4.39(1H,dq,10.8 Hz,6.4 Hz),4.23(1H,s), 3.17–3.09(3H,m),2.84(1H,s),2.70(2H,q,J= 7.8 Hz),2.36(1H,dd,J=12.2 Hz,7.3 Hz),2.23(1H,t,J=12.2 Hz),2.13(1H,td,J=12.7Hz,2.9 Hz),2.08–1.92(4H,m),1.87 (1H,brd,J=12.7 Hz),1.76(1H,m),1.64(3H,s),1.46(3H,d,J=6.4 Hz),1.41(1H,q,J=12.7 Hz),1.25(4H,m),1.11(1H,t,J=12.7 Hz),1.03(3H,s),0.97(3H,d,J=6.4 Hz),0.92(3H,d,J=6.4 Hz)

Example 15

Preparation of 1,13a-dihydroxy-11-isopropyl-4,7,8a-trimethyl-13-methylene-2-oxo-1,2,4,4a,5,7a,8,8a,9,10,11,11a,12,12a,13,13a-hexadecahydroindeno[5',6':4,5]cycloocta [1,2-c]pyran-10yl 3-phenyl-(E)-propenoate [Compound (16)]

Compound (2) (30 mg) was dissolved in 1.0 ml of dry dichloromethane, and 14.9 mg of cinnamoyl chloride and 11.0 mg of dimethylaminopyridine were added, and the mixture was stirred at room temperature for 4 hours. The reaction mixture was concentrated under reduced pressure, and the concentrate was charged onto silica gel column (Kieselgel 60 made by Merck & Co., Inc., 1.5ϕ×30 cm), and developed successively with n-hexane-ethyl acetate (2:1). Fractions containing the objective substance were concentrated under reduced pressure to obtain 35 mg of a residue.

The residue (35 mg) was dissolved in 2 ml of methanol, and 15.8 mg of p-toluenesulfonic acid hydrate was added, and the mixture was stirred at room temperature for 2 hours. After the reaction, the reaction mixture was concentrated under reduced pressure, and the concentrate was charged onto silica gel column (Kieselgel 60 made by Merck & Co., Inc., 1.5ϕ×30 cm), and developed with n-hexane-ethyl acetate (1:1). Fractions containing the objective substance were concentrated under reduced pressure to obtain 26.6 mg of Compound (16).

Rf value; 0.52 [Kieselgel 60$F_{254}$ made by Merck & Co., Inc. was used; developing solvent: n-hexane-ethyl acetate (1:1)]

Mass analysis; [FAB-MS] m/z: 549 (M+H)$^+$

Nuclear magnetic resonance spectrum;

$^1$H-NMR(δ ppm,400 MHz, CDCl$_3$): 7.65(1H,d,J=16.1 Hz),7.54–7.52(2H,m),7.39–7.37(3H,m),6.41(1H,d,J=16.1 Hz),5.37(1H,td,J=7.8 Hz,3.9 Hz),5.16(1H,d,J=1.0 Hz),5.04 (1H,t,J=8.8 Hz),4.72(1H,s),4.39(1H,dq,J=10.7 Hz,6.4 Hz), 4.22(1H,s),3.17–3.08(3H,m),2.85(1H,s),2.31(1H,dd,J=11.7 Hz,7.3 Hz),2.22(1H,td,J=12.2 Hz,2.4 Hz),2.12–1.83(6H,m), 1.74(1H,m),1.64(3H,s),1.46(3H,d,J=6.4 Hz),1.40(1H,q,J= 11.2 Hz),1.23(1H,dd,J=12.2 Hz,8.8 Hz),1.10(1H,t,J=12.2 Hz),1.02(3H,s),0.96(3H,d,J=6.4 Hz),0.92(3H,d,J=6.4 Hz)

Example 16

Preparation of 1,13a-dihydroxy-11-isopropyl-4,7,8a-trimethyl-13-methylene-2-oxo-1,2,4,4a,5,7a,8,8a,9, 10,11,11a,12,12a,13,13a-hexadecahydroindeno[5', 6':4,5]cycloocta [1,2-c]pyran-10yl 3-phenyl-propanoate [Compound (17)]

Compound (16) (15.0 mg) was dissolved in 5 ml of methanol, and a catalytic amount of 10% palladium-carbon was added, and the mixture was stirred under a hydrogen atmosphere at room temperature for 2 hours. The reaction mixture was filtered, and the filtrate was concentrated under reduced pressure to obtain a crude product. The crude product was charged onto silica gel column (Kieselgel 60 made by Merck & Co., Inc., 1.5ϕ×25 cm), and developed with n-hexane-ethyl acetate (2:1). Fractions containing the objective substance were concentrated under reduced pressure to obtain 9.7 mg of Compound (17).

Rf value; 0.57 [Kieselgel 60$F_{254}$ made by Merck & Co., Inc. was used; developing solvent: n-hexane-ethyl acetate (1:1)]

Mass analysis; [FAB-MS] m/z: 551 (M+H)$^+$

Nuclear magnetic resonance spectrum;

$^1$H-NMR(δ ppm,400 MHz, CDCl$_3$): 7.30–7.26(2H,m), 7.21–7.18(3H,m),5.22(1H,td,J=7.8 Hz,3.9 Hz),5.14(1H,d,J= 1.0 Hz),5.05(1H,t,J=8.8 Hz),4.70(1H,s),4.38(1H,dq,J=11.2 Hz,6.3 Hz),4.22(1H,brs),3.16–3.05(3H,m),2.94(2H,t,J=7.8 Hz),2.84(1H,s),2.59(2H,t,J=7.8 Hz),2.22–2.15 (2H,m), 2.07–1.91(4H,m),1.81(1H,dt,J=12.7 Hz,3.4 Hz),1.75–1.64 (2H,m),1.63(3H,s),1.46(3H,d,J=6.3 Hz),1.36(1H,q,J=12.7 Hz),1.10–0.99(2H,m),0.96(3H,d,J=5.9 Hz),0.82 (3H,d,J=6.4 Hz)

Example 17

Preparation of 1,13a-dihydroxy-11-isopropyl-4,7,8a-trimethyl-13-methylene-2-oxo-1,2,4,4a,5,7a,8,8a,9, 10,11,11a,12,12a,13,13a-hexadecahydroindeno[5', 6':4,5]cycloocta [1,2-c]pyran-10yl 2-pyrazinecarboxylate [Compound (18)]

Compound (4) (20 mg) was dissolved in 2.0 ml of dry dichloromethane, and 23 mg of 1-ethyl-3-(3-dimethylaminopropyl)-carbodiimide hydrochloride, 14.8 mg of dimethylaminopyridine and 14.9 mg of pyrazinecarboxylic acid were added, and the mixture was stirred at room temperature for 2 hours. After the reaction, the reaction mixture was concentrated under reduced pressure, the residue was dissolved in 2 ml of methanol, 400 μl of 1.0 molar hydrochloric acid was added, and the mixture was stirred at room temperature for 1 hour. After the reaction, the reaction mixture was concentrated under reduced pressure, the concentrate was extracted with 50 ml of ethyl acetate and 50 ml of water, and the resulting ethyl acetate layer was concentrated under reduced pressure. The resulting residue was charged onto silica gel column (Kieselgel 60 made by Merck & Co., Inc., 1.50ϕ×30 cm), and developed with chloroform-methanol (50:1). Fractions containing the objective substance were concentrated under reduced pressure to obtain 22.6 mg of Compound (18).

Rf value; 0.07 [Kieselgel 60$F_{254}$ made by Merck & Co., Inc. was used; developing solvent: n-hexane-ethyl acetate (1:1)]

Mass analysis; [FAB-MS] m/z: 525 (M+H)$^+$

Nuclear magnetic resonance spectrum;

$^1$H-NMR(δ ppm,400 MHz, CDCl$_3$): 9.29(1H,d,J=1.5 Hz), 8.75(2H,m),5.61(1H,dt,J=7.8 Hz,3.9 Hz),5.16(1H,d,J=1.0 Hz),5.05(1H,t,J=8.8 Hz),4.72(1H,s),4.39(1H,dq,J=10.7 Hz,6.3 Hz),4.23(1H,s),3.16–3.10(3H,m),2.83(1H,brs),2.40 (1H,dd,J=11.7 Hz,7.3 Hz),2.25–2.15(2H,m),2.08–1.91(4H, m),1.88–1.76(2H,m),1.64(3H,s),1.46(3H,d,J=6.3 Hz), 1.43–1.34(2H,m),1.12(1H,t,J=12.2 Hz),1.05(3H,s),0.97(3H, d,J=6.4 Hz),0.94(3H,d,J=6.4 Hz)

Example 18

Preparation of 1,13a-dihydroxy-11-isopropyl-4,7,8a-trimethyl-13-methylene-2-oxo-1,2,4,4a,5,7a,8,8a,9, 10,11,11a,12,12a,13,13a-hexadecahydroindeno[5', 6':4,5]cycloocta [1,2-c]pyran-10yl 2-chloronicotinate [Compound (19)]

Compound (4) (20 mg) was dissolved in 2.0 ml of dry dichloromethane, and 23.0 mg of 1-ethyl-3-(3-dimethylaminopropyl)-carbodiimide hydrochloride, 14.8 mg of dimethylaminopyridine and 18.8 mg of 2-chloronicotinoic acid were added, and the mixture was stirred at room temperature for 2 hours. After the reaction, the reaction mixture was concentrated under reduced pressure, the residue was dissolved in 2 ml of methanol, 400 μl of 1.0 molar hydrochloric acid was added, and the mixture was stirred at room temperature for 1 hour. After the reaction, the reaction mixture was concentrated under reduced pressure, the concentrate was extracted with 10 ml of ethyl acetate and 10 ml of water, and the resulting ethyl acetate layer was concentrated under reduced pressure. The residue was charged onto silica gel column (Kieselgel 60 made by Merck & Co., Inc., 1.5ϕ×30 cm), and developed with nhexane-ethyl acetate (1:1). Fractions containing the objective substance were concentrated under reduced pressure to obtain 18.0 mg of Compound (19).

Rf value; 0.20 [Kieselgel 60F$_{254}$ made by Merck & Co., Inc. was used; developing solvent: n-hexane-ethyl acetate (1:1)]

Mass analysis; [FAB-MS] m/z: 558 (M+H)$^+$

Nuclear magnetic resonance spectrum;

$^1$H-NMR($\delta$ ppm,400 MHz, CDCl$_3$): 8.51(1H,dd,J=4.9 Hz,2.0 Hz),8.10(1H,dd,J=7.8 Hz,2.0 Hz),7.33(1H,dd,J=7.8 Hz,4.9 Hz),5.51(1H,td,J=7.8 Hz,3.9 Hz),5.16(1H,d,J=1.0 Hz),5.05(1H,t,J=9.3Hz),4.72(1H,s),4.38(1H,dq,J=10.7 Hz,6.4 Hz),4.22(1H,d,J=3.9 Hz),3.16–3.08(3H,m),2.87(1H, d,J=8.8 Hz),2.39(1H,dd,J=12.2 Hz,7.3 Hz),2.22(1H,td,J= 12.2 Hz,2.9 Hz),2.14–1.91(5H,m),1.86(1H,dt,J=12.7 Hz,- 2.9 Hz),1.77(1H,m),1.64(3H,s),1.46(3H,d,J=6.4 Hz),1.40 (1H,q,J=12.7 Hz),1.33(1H,dd,J=12.2 Hz,8.3 Hz),1.11(1H,t, J=12.2 Hz),1.03(3H,s),0.97(3H,d,J=6.4 Hz),0.96(3H,d,J= 6.4 Hz)

Example 19

Preparation of 1,13a-dihydroxy-11-isopropyl-4,7,8 a-trimethyl-13-methylene-2-oxo-1,2,4,4a,5,7a,8,8a, 9,10,11,11a,12,12a,13,13a-hexadecahydroindeno[5', 6':4,5]cycloocta [1,2-c]pyran-10yl tetrahydro-2-furancarboxylate [Compound (20)]

Compound (4) (20 mg) was dissolved in 2.0 ml of dry dichloromethane, and 23.0 mg of 1-ethyl-3-(3-dimethylaminopropyl)-carbodiimide hydrochloride, 14.8 mg of dimethylaminopyridine and 13.9 mg of tetrahydro-2-furancarboxylic acid were added, and the mixture was stirred at room temperature for 2 hours . After the reaction, the reaction mixture was concentrated under reduced pressure, the residue was dissolved in 2 ml of methanol, 400 $\mu$l of 1.0 molar hydrochloric acid was added, and the mixture was stirred at room temperature for 1 hour. After the reaction, the reaction mixture was concentrated under reduced pressure, the concentrate was extracted with 10 ml of ethyl acetate and 10 ml of water, and the resulting ethyl acetate layer was concentrated under reduced pressure. The residue was charged onto silica gel column (Kieselgel 60 made by Merck & Co., Inc., 1.5$\phi$×30 cm), and developed with n-hexane-ethyl acetate (1:1). Fractions containing the objective substance were concentrated under reduced pressure to obtain 19.6 mg of Compound (20).

Rf value; 0.24 [Kieselgel 60F$_{254}$ made by Merck & Co., Inc. was used; developing solvent: n-hexane-ethyl acetate (1:1)]

Mass analysis; [FAB-MS] m/z: 517 (M+H)$^+$

Nuclear magnetic resonance spectrum;

$^1$H-NMR($\delta$ ppm,400 MHz, CDCl$_3$): 5.27(1H,td,J=7.8 Hz,3.9 Hz),5.14(1H,d,J=1.0 Hz),5.04(1H,t,J=8.8 Hz),4.70 (1H,s),4.44–4.34(2H,m),4.21(1H,d,J=3.9 Hz),4.02(1H,m), 3.91(1H,m),3.15– 3.05(3H,m),2.83(1H,s),2.27–2.16(3H,m), 2.08–2.01(2H,m),2.00–1.87(5H,m),1.84–1.66(3H,m),1.63 (3H,s),1.46(3H,d, J=6.4 Hz),1.37(1H,q,J=12.7 Hz),1.16(1H, td,J=11.2 Hz,2.0 Hz),1.07(1H,t,J=12.7 Hz),0.98(3H,s),0.93 (3H,d,J=5.9 Hz),0.87(3H,dd,J=5.9 Hz,3.4 Hz)

Example 20

Preparation of 1,13a-dihydroxy-11-isopropyl-4,7,8a-trimethyl-13-methylene-2-oxo-1,2,4,4a,5,7a,8,8a,9, 10,11,11a,12,12a,13,13a-hexadecahydroindeno[5', 6':4,5]cycloocta (1,2-c]pyran-10yl 2-chloro-6-methylnicotinate [Compound (21)]

Compound (4) (20 mg) was dissolved in 2.0 ml of dry dichloromethane, and 23.0 mg of 1-ethyl-3-(3-dimethylaminopropyl)-carbodiimide hydrochloride, 14.8 mg of dimethylaminopyridine and 20.6 mg of 2-chloro-6-methylnicotinic acid were added, and the mixture was stirred at room temperature for 2 hours . After the reaction, the reaction mixture was concentrated under reduced pressure, the residue was dissolved in 2 ml of methanol, 400 $\mu$l of 1.0 molar hydrochloric acid was added, and the mixture was stirred at room temperature for 1 hour. After the reaction, the reaction mixture was concentrated under reduced pressure, the concentrate was extracted with 10 ml of ethyl acetate and 10 ml of water, and the resulting ethyl acetate layer was concentrated under reduced pressure. The residue was charged onto silica gel column (Kieselgel 60 made by Merck & Co., Inc., 1.5$\phi$×30 cm), and developed with chloroform-methanol (30:1). Fractions containing the objective substance were concentrated under reduced pressure to obtain 24.6 mg of Compound (21).

Rf value; 0.34 [Kieselgel 60F$_{254}$ made by Merck & Co., Inc. was used; developing solvent: n-hexane-ethyl acetate (1:1)]

Mass analysis; [FAB-MS] m/z: 572 (M+H)$^+$

Nuclear magnetic resonance spectrum;

$^1$H-NMR($\delta$ ppm,400 MHz, CDCl$_3$): 8.02(1H,d,J=7.8 Hz), 7.15(1H,d,J=7.8 Hz),5.49(1H,td,J=7.8 Hz,3.9 Hz),5.16(1H, d,J=1.0 Hz),5.04(1H,t,J=8.8 Hz),4.72(1H,s),4.38(1H,dq,J= 10.7 Hz, 6.4 Hz),4.22(1H,d,J=2.9 Hz),3.16–3.08(3H,m), 2.85(1H,s), 2.58(3H,s),2.38(1H,dd,J=12.2 Hz,7.3 Hz),2.22 (1H,td,J=12.7 Hz,2.9 Hz),2.14–1.91(5H, m),1.86(1H,dt,J= 12.7 Hz,2.9 Hz),1.76(1H, m),1.64(3H,s),1.46(3H,d,J=6.4 Hz),1.40(1H,q,J=12.7 Hz),1.32(1H,dd,J=11.7 Hz,8.3 Hz), 1.11(1H, t,J=12.2 Hz),1.03(3H,s),0.97(3H,d,J=6.8 Hz),0.95 (3H,d,J=7.3 Hz)

Example 21

Preparation of 1,13a-dihydroxy-11-isopropyl-4,7,8a-trimethyl-13-methylene-2-oxo-1,2,4,4a,5,7a,8,8a,9, 10,11,11a,12,12a,13,13a-hexadecahydroindeno[5', 6':4,5]cycloocta [1,2-c]pyran-10-yl nicotinate [Compound (22)]

Compound (4) (20 mg) was dissolved in 2.0 ml of dry dichloromethane, and 23.0 mg of 1-ethyl-3-(3-dimethylaminopropyl)-carbodiimide hydrochloride, 14.8 mg of dimethylaminopyridine and 14.5 mg of nicotinic acid were added, and the mixture was stirred at room temperature for 2 hours. After the reaction, the reaction mixture was concentrated under reduced pressure, the residue was dissolved in 2 ml of methanol, 400 $\mu$l of 1.0 molar hydrochloric acid was added, and the mixture was stirred at room temperature for 1 hour. After the reaction, the reaction mixture was concentrated under reduced pressure, the concentrate was extracted with 10 ml of ethyl acetate and 10 ml of water, and the resulting ethyl acetate layer was concentrated under reduced pressure. The residue was charged onto silica gel column (Kieselgel 60 made by Merck & Co., Inc., 1.5$\phi$×30 cm), and developed with chloroform-methanol (50:1). Fractions containing the objective substance were concentrated under reduced pressure to obtain 25.0 mg of Compound (22).

Rf value; 0.12 [Kieselgel 60F$_{254}$ made by Merck & Co., Inc. was used; developing solvent: n-hexane-ethyl acetate (1:1)]

Mass analysis; [FAB-MS] m/z: 524 (M+H)$^+$

Nuclear magnetic resonance spectrum;

$^1$H-NMR($\delta$ ppm,400 MHz, CDCl$_3$): 9.21(1H,d,J=1.5 Hz), 8.77(1H,dd,J=4.9 Hz,1.5 Hz),8.28(1H,dt,J=7.8 Hz,1.5 Hz), 7.39(1H,dd,J=7.8 Hz,4.9 Hz),5.50(1H,td,J=7.8 Hz,3.9 Hz), 5.16(1H,d,J=1.0 Hz),5.05(1H,t,J=8.3 Hz),4.73(1H,s),4.39 (1H,dq,J=11.2 Hz,6.4 Hz),4.23(1H,s),3.17–3.11(3H,m),2.92 (1H,brs),2.37(1H,dd,J=12.2 Hz,7.3 Hz),2.23(1H,td,J=12.2 Hz,2.9 Hz),2.14(1H,td,J=12.7 Hz,2.9 Hz),2.08–1.92(4H,m), 1.88(1H,dt,J=12.7 Hz,3.4 Hz),1.82–1.73(1H,m),1.64(3H,s), 1.46(3H,d,J=6.4 Hz),1.41(1H,q,J=12.7 Hz),1.30(1H,dd,J= 11.7 Hz,8.3 Hz),1.12(1H,t,J=12.2 Hz),1.04(3H,s),0.97(3H, d,J=6.3 Hz),0.92(3H,d,J=6.8 Hz)

Example 22

Preparation of 1,13a-dihydroxy-11-isopropyl-4,7,8a-trimethyl-13-methylene-2-oxo-1,2,4,4a,5,7a,8,8a,9, 10,11,11a,12,12a,13,13a-hexadecahydroindeno[5', 6':4,5]cycloocta [1,2-c]pyran-10-yl 4-fluorobenzoate [Compound (23)]

Compound (4) (20 mg) was dissolved in 2.0 ml of dry dichloromethane, and 23.0 mg of 1-ethyl-3-(3-dimethylaminopropyl)-carbodiimide hydrochloride, 14.8 mg of dimethylaminopyridine and 16.8 mg of 4-fluorobenzoic acid were added, and the mixture was stirred at room temperature for 2 hours. After the reaction, the reaction mixture was concentrated under reduced pressure, the residue was dissolved in 2 ml of methanol, 400 $\mu$l of 1.0 molar hydrochloric acid was added, and the mixture was stirred at room temperature for 1 hour. After the reaction, the reaction mixture was concentrated under reduced pressure, the concentrate was extracted with 10 ml of ethyl acetate and 10 ml of water, and the resulting ethyl acetate layer was concentrated under reduced pressure. The residue was charged onto silica gel column (Kieselgel 60 made by Merck & Co., Inc., 1.5$\phi$×30 cm), and developed with chloroform-methanol (50:1). Fractions containing the objective substance were concentrated under reduced pressure to obtain 22.3 mg of Compound (23).

Rf value; 0.61 [Kieselgel 60$F_{254}$ made by Merck & Co., Inc. was used; developing solvent: n-hexane-ethyl acetate (1:1)]

Mass analysis; [FAB-MS] m/z: 563 (M+Na)$^+$

Nuclear magnetic resonance spectrum;

$^1$H-NMR($\delta$ ppm,400 MHz, CDCl$_3$): 8.04(2H,dd,J=8.8 Hz,5.4 Hz),7.10(2H,t,J=8.8 Hz),5.46(1H,td,J=7.8 Hz,3.9 Hz),5.16(1H,d,J=1.0 Hz),5.05(1H,t,J=8.8 Hz),4.72(1H,s), 4.39(1H,dq,J=10.7 Hz,6.4 Hz),4.23(1H,s),3.17–3.13(3H,m), 2.85(1H,s),2.35(1H,dd,J=11.7 Hz,7.3 Hz),2.23(1H,td,J= 12.2 Hz,2.9 Hz),2.13(1H,td,J=12.7 Hz,2.9 Hz),2.08–1.91 (4H,m),1.87(1H,dt,J=12.7 Hz,3.4 Hz),1.77(1H,m),1.64(3H, s),1.46(3H,d,J=6.4 Hz),1.41(1H,q,J=12.7 Hz),1.28(1H,dd, J=11.7 Hz,8.3 Hz),1.10(1H,t,J=12.2 Hz),1.03(3H,s),0.97 (3H,d,J=6.3 Hz),0.92(3H,d,J=6.4 Hz)

Example 23

Preparation of 1,13a-dihydroxy-11-isopropyl-4,7,8a-trimethyl-13-methylene-2-oxo-1,2,4,4a,5,7a,8,8a,9, 10,11,11a,12,12a,13,13a-hexadecahydroindeno[5', 6':4,5]cycloocta [1,2-c]pyran-10-yl 6-methylnicotinate [Compound (24)]

Compound (4) (20 mg) was dissolved in 2.0 ml of dry dichloromethane, and 23.0 mg of 1-ethyl-3-(3-dimethylaminopropyl)-carbodiimide hydrochloride, 14.8 mg of dimethylaminopyridine and 16.5 mg of 6-methylnicotinic acid were added, and the mixture was stirred at room temperature for 2 hours. After the reaction, the reaction mixture was concentrated under reduced pressure, the residue was dissolved in 2 ml of methanol, 400 $\mu$l of 1.0 molar hydrochloric acid was added, and the mixture was stirred at room temperature for 1 hour. After the reaction, the reaction mixture was concentrated under reduced pressure, the concentrate was extracted with 10 ml of ethyl acetate and 10 ml of water, and the resulting ethyl acetate layer was concentrated under reduced pressure. The residue was charged onto silica gel column (Kieselgel 60 made by Merck & Co., Inc., 1.5$\phi$×30 cm), and developed with chloroform-methanol (50:1). Fractions containing the objective substance were concentrated under reduced pressure to obtain 24.5 mg of Compound (24).

Rf value; 0.14 [Kieselgel 60$F_{254}$ made by Merck & Co., Inc. was used; developing solvent: n-hexane-ethyl acetate (1:1)]

Mass analysis; [FAB-MS] m/z: 538 (M+H)$^+$

Nuclear magnetic resonance spectrum;

$^1$H-NMR($\delta$ ppm,400 MHz,CDCl$_3$): 9.08(1H,d,J=2.0 Hz), 8.15(1H,dd,J=8.3 Hz,2.0 Hz),7.23(1H,d,J=8.3 Hz),5.48(1H, td,J=7.8 Hz,3.9 Hz),5.16(1H,d,J=1.0 Hz),5.05(1H,t,J=9.8 Hz),4.73(1H,s),4.39(1H,dq,J=11.2 Hz,6.4 Hz),4.23(1H,s), 3.17–3.11(3H,m),2.86(1H,brs),2.62(3H,s),2.35(1H,dd,J= 12.2 Hz,7.3 Hz),2.23(1H,td,J=9.8 Hz,2.9 Hz),2.14(1H,td,J= 9.8 Hz,2.9 Hz),2.08–1.92(4H,m),1.87(1H,dt,J=12.7 Hz,2.9 Hz),1.77(1H,m),1.64(3H,s),1.46(3H,d,J=6.4 Hz),1.41(1H,q, J=12.7 Hz),1.29(1H,dd,J=12.2 Hz,8.3 Hz),1.12(1H,t,J=12.2 Hz),1.04(3H,s),0.97(3H,d,J=6.4 Hz),0.91(3H,d,J=6.8 Hz)

Example 24

Preparation of 1,13a-dihydroxy-11-isopropyl-4,7,8a-trimethyl-13-methylene-2-oxo-1,2,4,4a,5,7a,8,8a,9, 10,11,11a,12,12a,13,13a-hexadecahydroindeno[5', 6':4,5]cycloocta [1,2-c]pyran-10-yl 2-methylnicotinate [Compound (25)]

Compound (4) (20 mg) was dissolved in 2.0 ml of dry dichloromethane, and 23.0 mg of 1-ethyl-3-(3-dimethylaminopropyl)-carbodiimide hydrochloride, 14.8 mg of dimethylaminopyridine and 16.5 mg of 2-methylnicotinic acid were added, and the mixture was stirred at room temperature for 2 hours. After the reaction, the reaction mixture was concentrated under reduced pressure, the residue was dissolved in 2 ml of methanol, 400 $\mu$l of 1.0 molar hydrochloric acid was added, and the mixture was stirred at room temperature for 1 hour. After the reaction, the reaction mixture was concentrated under reduced pressure, the concentrate was extracted with 10 ml of ethyl acetate and 10 ml of water, and the resulting ethyl acetate layer was concentrated under reduced pressure. The residue was charged onto silica gel column (Kieselgel 60 made by Merck & Co., Inc., 1.5$\phi$×30 cm), and developed with chloroform-methanol (50:1). Fractions containing the objective substance were concentrated under reduced pressure to obtain 24.5 mg of Compound (25).

Rf value; 0.12 [Kieselgel 60$F_{254}$ made by Merck & Co., Inc. was used; developing solvent: n-hexane-ethyl acetate (1:1)]

Mass analysis; [FAB-MS] m/z: 538 (M+H)$^+$

Nuclear magnetic resonance spectrum;

$^1$H-NMR($\delta$ ppm,400 MHz, CDCl$_3$): 8.61(1H,dd,J=4.9 Hz,2.0 Hz),8.14(1H,dd,J=7.8 Hz,2.0 Hz),7.21(1H,dd,J=7.8 Hz,4.9 Hz),5.48(1H,td,J=7.8 Hz,3.9 Hz),5.16(1H,d,J=1.0 Hz),5.05(1H,t,J=8.8 Hz),4.73(1H,s),4.39(1H,dq,J=10.7 Hz,6.4 Hz),4.23(1H,s),3.17–3.08(1H,m),2.93(1H,brs),2.84 (1H,s),2.38(1H,dd,J=12.2 Hz,7.3 Hz),2.23(1H,td,J=12.2

Hz,2.4 Hz),2.14–1.91(5H,m),1.87(1H,dt,J=12.7 Hz,3.4 Hz), 1.82–1.68(1H,m),1.64(3H,s),1.46(3H,d,J=6.4 Hz),1.41(1H, q,J=12.7 Hz),1.28(1H,dd,J=12.2 Hz,8.8 Hz),1.11(1H,t,J= 12.2 Hz),1.04(3H,s),0.96(3H,d,J=6.3 Hz),0.94 (3H,d,J=6.4 Hz)

Example 25

Preparation of 1,13a-dihydroxy-11-isopropyl-4,7,8a-trimethyl-13-methylene-2-oxo-1,2,4,4a,5,7a,8,8a,9, 10,11,11a,12,12a,13,13a-hexadecahydroindeno[5', 6':4,5]cycloocta [1,2-c]pyran-10-yl 6-chloronicotinate [Compound (26)]Compound (4) (20 mg) was dissolved in 2.0 ml of dry dichloromethane, and 23.0 mg of 1-ethyl-3-(3-dimethylaminopropyl)-carbodiimide hydrochloride, 14.8 mg of dimethylaminopyridine and 18.9 mg of 6-chloronicotinic acid were added, and the mixture was stirred at room temperature for 2 hours. After the reaction, the reaction mixture was concentrated under reduced pressure, the residue was dissolved in 2 ml of methanol, 400 μl of 1.0 molar hydrochloric acid was added, and the mixture was stirred at room temperature for 1 hour. After the reaction, the reaction mixture was concentrated under reduced pressure, the concentrate was extracted with 10 ml of ethyl acetate and 10 ml of water, and the resulting ethyl acetate layer was concentrated under reduced pressure. The residue was charged onto silica gel column (Kieselgel 60 made by Merck & Co., Inc., 1.5ϕ×30 cm), and developed with chloroform-methanol (50:1). Fractions containing the objective substance were concentrated under reduced pressure to obtain 23.8 mg of Compound (26).

Rf value; 0.52 [Kieselgel 60$F_{254}$ made by Merck & Co., Inc. was used; developing solvent: n-hexane-ethyl acetate (1:1)]

Mass analysis; [FAB-MS] m/z: 558 (M+H)$^+$

Nuclear magnetic resonance spectrum;

$^1$H-NMR(δ ppm,400 MHz, CDCl$_3$): 8.97(1H,d,J=2.4 Hz), 8.22(1H,dd,J=8.3 Hz,2.4 Hz),7.41(1H,d,J=8.3 Hz),5.49(1H, td,J=7.8 Hz,3.9 Hz),5.16(1H,d,J=1.5 Hz),5.05(1H,t,J=8.8 Hz),4.72(1H,s),4.39(1H,dq,J=11.2 Hz,6.4 Hz),4.23(1H,s), 3.16–3.10(3H,m),2.86(1H,s),2.35(1H,dd,J=11.7 Hz,7.3 Hz), 2.22(1H,t,J=12.7 Hz),2.14(1H,t,J=12.7 Hz),2.08–1.92(4H, m),1.87(1H,d,J=12.7 Hz),1.77(1H,m),1.64(3H,s),1.46(3H, d,J=6.4 Hz),1.41(1H,q,J=12.7 Hz),1.29(1H,dd,J=11.7 Hz,8.3 Hz),1.11(1H,t,J=12.7 Hz),1.04(3H,s),0.97(3H,d,J= 6.4 Hz),0.91(3H,d,J=6.8 Hz)

Example 26

Preparation of 1,13a-dihydroxy-11-isopropyl-4,7,8a-trimethyl-13-methylene-2-oxo-1,2,4,4a,5,7a,8,8a,9, 10,11,11a,12,12a,13,13a-hexadecahydroindeno[5', 6':4,5]cycloocta [1,2-c]pyran-10-yl 6-methylpicolinate [Compound (27)]

Compound (4) (20 mg) was dissolved in 2.0 ml of dry dichloromethane, and 23.0 mg of 1-ethyl-3-(3-dimethylaminopropyl)-carbodiimide hydrochloride, 14.8 mg of dimethylaminopyridine and 16.5 mg of 6-methylpicolinic acid were added, and the mixture was stirred at room temperature for 2 hours. After the reaction, the reaction mixture was concentrated under reduced pressure, the residue was dissolved in 2 ml of methanol, 400 μl of 1.0 molar hydrochloric acid was added, and the mixture was stirred at room temperature for 1 hour. After the reaction, the reaction mixture was concentrated under reduced pressure, the concentrate was extracted with 10 ml of ethyl acetate and 10 ml of water, and the resulting ethyl acetate layer was concentrated under reduced pressure. The residue was charged onto silica gel column (Kieselgel 60 made by Merck & Co., Inc., 1.5ϕ×30 cm), and developed with chloroform-methanol (50:1). Fractions containing the objective substance were concentrated under reduced pressure to obtain 22.0 mg of Compound (27).

Rf value; 0.16 [Kieselgel 60$F_{254}$ made by Merck & Co., Inc. was used; developing solvent: n-hexane-ethyl acetate (1:1)]

Mass analysis; [FAB-MS] m/z: 538 (M+H)$^+$

Nuclear magnetic resonance spectrum;

$^1$H-NMR(δ ppm,400 MHz, CDCl$_3$): 7.86(1H,d,J=7.8 Hz), 7.69(1H,t,J=7.8 Hz),7.31(1H,d,J=7.8 Hz),5.54(1H,td,J=7.8 Hz,3.9 Hz),5.16(1H,d,J=1.0 Hz),5.04(1H,t,J=8.8 Hz),4.72 (1H,s),4.39(1H,dq,J=10.7 Hz,6.4 Hz),4.22(1H,s),3.16–3.12 (3H,m),2.86(1H,s),2.66(3H,s),2.39(1H,dd,J=12.2 Hz,7.3 Hz),2.23(1H,td,J=12.2 Hz,2.9 Hz),2.15(1H,td,J=12.7 Hz,2.9 Hz),2.07–1.91(4H,m),1.86(1H,dt,J=12.7 Hz,3.4 Hz),1.76 (1H,m),1.64(3H,s),1.46(3H,d,J=6.4 Hz),1.41(1H,q,J=12.7 Hz),1.32(1H,dd,J=12.2 Hz,8.3 Hz),1.11(1H,t,J=12.7 Hz), 1.04(3H,s),0.97(3H,d,J=6.3 Hz),0.94 (3H,d,J=6.8 Hz)

Example 27

Preparation of 1,13a-dihydroxy-11-isopropyl-4,7,8a-trimethyl-13-methylene-2-oxo-1,2,4,4a,5,7a,8,8a,9, 10,11,11a,12,12a,13,13a-hexadecahydroindeno[5', 6':4,5]cycloocta [1,2-c]pyran-10-yl 4-cyanobenzoate [Compound (28)]

Compound (4) (20 mg) was dissolved in 2.0 ml of dry dichloromethane, and 23.0 mg of 1-ethyl-3-(3-dimethylaminopropyl)-carbodiimide hydrochloride, 14.8 mg of dimethylaminopyridine and 17.7 mg of 4-cyanobenzoic acid were added, and the mixture was stirred at room temperature for 2 hours. After the reaction, the reaction mixture was concentrated under reduced pressure, the residue was dissolved in 2 ml of methanol, 400 μl of 1.0 molar hydrochloric acid was added, and the mixture was stirred at room temperature for 1 hour. After the reaction, the reaction mixture was concentrated under reduced pressure, the concentrate was extracted with 10 ml of ethyl acetate and 10 ml of water, and the resulting ethyl acetate layer was concentrated under reduced pressure. The residue was charged onto silica gel column (Kieselgel 60 made by Merck & Co., Inc., 1.5ϕ×30 cm), and developed with chloroform-methanol (50:1). Fractions containing the objective substance were concentrated under reduced pressure to obtain 23.0 mg of Compound (28).

Rf value; 0.47 [Kieselgel 60$F_{254}$ made by Merck & Co., Inc. was used; developing solvent: n-hexane-ethyl acetate (1:1)]

Mass analysis; m/z: 570 (M+H)$^+$

Nuclear magnetic resonance spectrum;

$^1$H-NMR(δ ppm,400 MHz, CDCl$_3$): 8.12(2H,d,J=8.3 Hz), 7.74(2H,d,J=8.3 HZ),5.49(1H,td,J=7.8 Hz,3.9 Hz),5.16(1H, d,J=1.0 Hz),5.05(1H,t,J=8.8 Hz),4.73(1H,s),4.39(1H,dq,J= 11.2 Hz,6.4 Hz),4.23(1H,s),3.16–3.10(3H,m),2.86(1H,s), 2.37(1H,dd,J=11.7 Hz,7.3 Hz),2.22(1H,td,J=12.7 Hz,2.4 Hz),2.13(1H,td,J=12.7 Hz,2.4 Hz),2.08–1.92(4H,m),1.87 (1H,dt,J=12.7 Hz,2.9 Hz),1.77(1H,m),1.64(3H,s),1.46(3H, d,J=6.4 Hz),1.41(1H,q,J=12.7 Hz),1.28(1H,dd,J=11.7 Hz,8.3 Hz),1.11(1H,t,J=12.7 Hz),1.04(3H,s),0.97(3H,d,J= 6.4 Hz),0.91(3H,d,J=6.4 Hz)

Example 28

Preparation of 1,13a-dihydroxy-11-isopropyl-4,7,8a-trimethyl-13-methylene-2-oxo-1,2,4,4a,5,7a,8,8a,9, 10,11,11a,12,12a,13,13a-hexadecahydroindeno[5', 6':4,5]cycloocta [1,2-c]pyran-10-yl 2,3-dimethoxybenzoate [Compound (29)]

Compound (4) (20 mg) was dissolved in 2.0 ml of dry dichloromethane, and 23.0 mg of 1-ethyl-3-(3-dimethylaminopropyl)-carbodiimide hydrochloride, 14.8 mg of dimethylaminopyridine and 21.9 mg of 2,3-dimethoxybenzoic acid were added, and the mixture was stirred at room temperature for 2 hours. After the reaction, the reaction mixture was concentrated under reduced pressure, the residue was dissolved in 2 ml of methanol, 400 µl of 1.0 molar hydrochloric acid was added, and the mixture was stirred at room temperature for 1 hour. After the reaction, the reaction mixture was concentrated under reduced pressure, the concentrate was extracted with 10 ml of ethyl acetate and 10 ml of water, and the resulting ethyl acetate layer was concentrated under reduced pressure. The residue was charged onto silica gel column (Kieselgel 60 made by Merck & Co., Inc., 1.5ϕ×30 cm), and developed with chloroform-methanol (50:1). Fractions containing the objective substance were concentrated under reduced pressure to obtain 24.0 mg of Compound (29).

Rf value; 0.35 [Kieselgel 60$F_{254}$ made by Merck & Co., Inc. was used; developing solvent: n-hexane-ethyl acetate (1:1)]

Mass analysis; [FAB-MS] m/z: 583 (M+H)$^+$

Nuclear magnetic resonance spectrum;

$^1$H-NMR(δ ppm,400 MHz, CDCl$_3$): 7.27(1H,m), 7.10–7.03(2H,m),5.47(1H,td,J=7.8 Hz,4.4 Hz),5.16(1H,s), 5.04(1H,t,J=9.3 Hz),4.72(1H,s),4.39(1H,dq,J=11.2 Hz,6.3 Hz),4.22(1H,s),3.90(3H, s),3.88(3H,s),3.16–3.08(3H,m), 2.83(1H,s),2.39(1H,dd,J=12.2 Hz,7.3 Hz),2.22(1H,td,J= 12.2 Hz,2.9 Hz),2.12–1.90(5H,m),1.85(1H,dt,J=13.2 Hz,3.4 Hz),1.77(1H,m),1.64(3H,s),1.46(3H,d,J=6.3 Hz),1.40(1H, m),1.30(1H,dd,J=11.7 Hz,8.3 Hz),1.10(1H,t,J=12.2 Hz), 1.03(3H,s),0.96(6H,d,J=6.3 Hz)

Example 29

Preparation of 1,13a-dihydroxy-11-isopropyl-4,7,8a-trimethyl-13-methylene-2-oxo-1,2,4,4a,5,7a,8,8a,9, 10,11,11a,12,12a,13,13a-hexadecahydroindeno[5', 6':4,5]cycloocta [1,2-c]pyran-10-yl 3-quinolinecarboxylate [Compound (30)]

Compound (4) (20 mg) was dissolved in 2.0 ml of dry dichloromethane, and 23.0 mg of 1-ethyl-3-(3-dimethylaminopropyl)-carbodiimide hydrochloride, 14.8 mg of dimethylaminopyridine and 20.8 mg of 3-quinolinecarboxylic acid were added, and the mixture was stirred at room temperature for 2 hours. After the reaction, the reaction mixture was concentrated under reduced pressure, the residue was dissolved in 2 ml of methanol, 400 µl of 1.0 molar hydrochloric acid was added, and the mixture was stirred at room temperature for 1 hour. After the reaction, the reaction mixture was concentrated under reduced pressure, the concentrate was extracted with 10 ml of ethyl acetate and 10 ml of water, and the resulting ethyl acetate layer was concentrated under reduced pressure. The residue was charged onto silica gel column (Kieselgel 60 made by Merck & Co., Inc., 1.5ϕ×30 cm), and developed with chloroform-methanol (50:1). Fractions containing the objective substance were concentrated under reduced pressure to obtain 22.6 mg of Compound (30).

Rf value; 0.24 [Kieselgel 60$F_{254}$ made by Merck & Co., Inc. was used; developing solvent: n-hexane-ethyl acetate (1:1)]

Mass analysis; [FAB-MS] m/z: 574 (M+H)$^+$

Nuclear magnetic resonance spectrum;

$^1$H-NMR(δ ppm,400 MHz, CDCl$_3$): 9.44(1H,d,J=2.4 Hz), 8.82(1H,d,J=1.5 Hz),8.18(1H,d,J=8.3 Hz),7.95(1H,dd,J=8.3 Hz,1.0 Hz),7.84(1H,ddd,J=13.7 Hz,6.8 Hz,1.5 Hz),7.63(1H, ddd,J=13.7 Hz,J=6.8 Hz,J=1.0 Hz),5.57(1H,td,J=7.8 Hz,3.9 Hz),5.18(1H,d,J=1.0 Hz),5.05(1H,t,J=9.3 Hz),4.74(1H,s), 4.40(1H,dq,J=11.2 Hz,6.4 Hz),4.24(1H,s),3.18–3.12(3H,m), 2.91(1H,s),2.41(1H,dd,J=11.7 Hz,7.3 Hz),2.28–2.16(2H,m), 2.09–1.88(5H,m),1.79(1H,m),1.65(3H,s),1.47(3H,d,J=6.4 Hz),1.44(1H,q,J=11.7 Hz),1.36(1H,dd,J=11.7 Hz,8.3 Hz), 1.15(1H,t,J=12.7 Hz),1.07(3H,s),0.99(3H,d,J=6.3 Hz),0.95 (3H,d,J=6.3 Hz)

Example 30

Preparation of 1,13a-dihydroxy-11-isopropyl-4,7,8a-trimethyl-13-methylene-2-oxo-1,2,4,4a,5,7a,8,8a,9, 10,11,11a,12,12a,13,13a-hexadecahydroindeno[5', 6':4,5]cycloocta [1,2-c]pyran-10-yl (E)-2-phenyl-1-ethene-1sulfonate [Compound (31)]

Compound (2) (50 mg) was dissolved in 1.0 ml of dry pyridine, and 36.4 mg of trans-β-styrenesulfonyl chloride and 21.9 mg of dimethylaminopyridine were added, and the mixture was stirred at room temperature. For making the reaction progress, 3 hours later, 36.4 mg of trans-β-styrenesulfonyl chloride and 21.9 mg of dimethylaminopyridine were added, and the mixture was stirred for further 6 hours. The reaction mixture was concentrated under reduced pressure, and the concentrate was charged onto silica gel column (Kieselgel 60 made by Merck & Co., Inc., 1.5ϕ×25 cm), and developed with n-hexane-ethyl acetate (2:1). Fractions containing the objective substance were concentrated under reduced pressure to obtain 12.2 mg of Compound (31).

Rf value; 0.27 [Kieselgel 60$F_{254}$ made by Merck & Co., Inc. was used; developing solvent: n-hexane-ethyl acetate (1:1)]

Mass analysis; [FAB-MS] m/z: 585 (M+H)$^+$

Nuclear magnetic resonance spectrum;

$^1$H-NMR(δ ppm,400 MHz, CDCl$_3$): 7.59(1H,d,J=15.6 Hz),7.50(2H,dd,J=7.2 Hz,2.0 Hz),7.46–7.42(3H,m),6.73 (1H,d,J=15.6 Hz),5.12(1H,d,J=1.0 Hz),5.10(1H,td,J=7.8 Hz,3.9 Hz),5.04(1H,t,J=9.8 Hz),4.70(1H,s),4.36(1H,dq,J= 10.8 Hz,6.4 Hz),4.21(1H,s),3.14–3.05(2H,m),2.93(1H,brs), 2.28(1H,dd,J=12.2 Hz,7.3 Hz),2.17(1H,dt,J=12.2 Hz,2.4 Hz),2.08–2.01(1H,m),1.98–1.87(3H,m),1.82(1H,dt,J=12.7 Hz,3.4 Hz),1.72(1H,m),1.61(3H,s),1.55(1H,dd,J=12.2 Hz,7.8 Hz),1.45(3H,d,J=6.4 Hz),1.33(1H,q,J=12.7 Hz),1.10 (1H,dd,J=12.7 Hz,12.2 Hz),0.99(3H,d,J=6.8),0.95(3H,d,J= 6.3 Hz),0.93(3H,s)

Example 31

Preparation of 1,13a-dihydroxy-11-isopropyl-4,7,8a-trimethyl-13 -methylene-2-oxo-1,2,4,4a,5,7a,8,8a,9, 10,11,11a,12,12a,13,13a-hexadecahydroindeno[5', 6':4,5]cycloocta [1,2-c]pyran-10-yl 1butanesulfonate [Compound (32)]

Compound (2) (30 mg) was dissolved in 1.0 ml of dry pyridine, and 11.1 µl of 1 butanesulfonyl chloride and 10.5 mg of dimethylaminopyridine were added, and the mixture was stirred at room temperature. For making the reaction progress, 5 hours later, 11.1 μl of 1butanesulfonyl chloride was added, and the mixture was stirred for further 3 hours. The reaction mixture was concentrated under reduced pressure, the concentrate was charged onto silica gel column (Kieselgel 60 made by Merck & Co., Inc., 1.5ϕ×25 cm), and developed with n-hexane-ethyl acetate (2:1). Fractions containing the objective substance were concentrated under reduced pressure to obtain 3.1 mg of Compound (32).

Rf value; 0.43 [Kieselgel 60$F_{254}$ made by Merck & Co., Inc. was used; developing solvent: n-hexane-ethyl acetate (1:1)]

Mass analysis; [FAB-MS] m/z: 539 (M+H)$^+$

Nuclear magnetic resonance spectrum;

$^1$H-NMR(δ ppm,400 MHz, CDCl$_3$): 5.18(1H,td,J=7.8 Hz,3.9 Hz),5.14(1H,d,J=1.0 Hz),5.05(1H,t,J=9.3 Hz),4.71 (1H,s),4.38(1H,dq,J=11.2 Hz,6.4 Hz),4.21(1H,s),3.15–3.03 (5H,m),2.82(1H,brs),2.30(1H,dd,J=12.2 Hz,7.3 Hz),2.19 (1H,td,J=9.3 Hz,2.9 Hz),2.08–1.92(4H,m),1.88–1.69(5H, m),1.63(3H,s),1.53(1H,dd,J=12.2 Hz,7.8 Hz),1.46(5H,m), 1.36(1H,q,J=12.7 Hz),1.11(1H,t,J=12.7 Hz),1.01(3H,d,J= 6.8 Hz),0.97(3H,d,J=7.8 Hz),0.96(3H,s),0.96(3H,t,J=7.3 Hz)

Example 32

Preparation of 1,13a-dihydroxy-11-isopropyl-4,7,8a-trimethyl-13-methylene-2-oxo-1,2,4,4a,5,7a,8,8a,9,10,11,11a,12,12a,13,13a-hexadecahydroindeno[5',6':4,5]cycloocta [1,2-c]pyran-10-yl N-ethylcarbamate [Compound (33)]

Compound (2) (30 mg) was dissolved in 2.0 ml of dry toluene, and 9.4 μof ethyl isocyanate and 50 μl of dibutyltin diacetate were added, and the mixture was stirred at room temperature. For making the reaction progress, 1.5 hours and 3 hours later, 9.4 μl and 6.4 μl of ethyl isocyanate were added, respectively, and the mixture was stirred for further 17 hours. The reaction mixture was concentrated under reduced pressure, and the concentrate was charged onto silica gel column (Kieselgel 60 made by Merck & Co., Inc., 1.5ϕ×25 cm) and developed with n-hexane-ethyl acetate (2:1). Fractions containing the objective substance were concentrated under reduced pressure to obtain the objective substance of crude purification. For further purification, the crude substance was subjected to reverse-phase chromatography (Chromatorex ODS made by FUJI SILYSIA CHEMICAL LTD., 2.0ϕ×25 cm, water-acetonitrile (3:7), 10.0 ml/min), and fractions containing the objective substance were concentrated under reduced pressure to obtain 22.0 mg of Compound (33).

Rf value; 0.32 [Kieselgel 60$F_{254}$ made by Merck & Co., Inc. was used; developing solvent: n-hexane-ethyl acetate (1:1)]

Mass analysis; [FAB-MS] m/z: 490 (M+H)$^+$

Nuclear magnetic resonance spectrum;

$^1$H-NMR(δ ppm,400 MHz,CDCl$_3$):5.14(1H,d,J=1.0 Hz), 5.14(1H,brs),5.03(1H,t,J=8.8 Hz),4.70(1H,s),4.52(1H,brs), 4.38(1H,dq,J=10.7 Hz,6.4 Hz),4.21(1H,s),3.21–3.02(5H,m), 2.84(1H,brs),2.25–2.16(2H,m),2.04(1H,dd,J=10.7 Hz,7.3 Hz),1.98–1.90(3H,m),1.81(1H,td,J=12.7 Hz,2.9 Hz),1.69 (2H,m), 1.63(3H,s),1.46(3H,d,J=6.4 Hz),1.36(1H,q,J=12.7 Hz),1.19(1H,dd,J=12.2 Hz,8.8 Hz),1.13(3H,t,J=7.3 Hz), 1.07(1H,t,J=12.2 Hz),0.97(3H,s),0.93(3H,d,J=5.9 Hz),0.92 (3H,d,J=5.9 Hz)

Example 33

Preparation of 1,13a-dihydroxy-11-isopropyl-4,7,8a-trimethyl-13-methylene-2-oxo-1,2,4,4,5,7a,8,8a,9,10,11,11a,12,12a,13,13a-hexadecahydroindoin [5',6':4,5]cycloocta [1,2-c]pyran-10-yl N-n-propylcarbamate [Compound (34)]

Compound (2) (30 mg) was dissolved in 0.7 ml of dry toluene, and 8.0 μl of n-propyl isocyanate and 38 μl of dibutyltin diacetate were added, and the mixture was stirred at room temperature for 22 hours. The reaction mixture was concentrated under reduced pressure, and the concentrate was charged onto silica gel column (Kieselgel 60 made by Merck & Co., Inc., 1.5ϕ×23 cm) and developed with n-hexane-ethyl acetate (3:1). Fractions containing the objective substance were concentrated under reduced pressure to obtain 27.2 mg of Compound (34).

Rf value; 0.50 [Kieselgel 60$F_{254}$ made by Merck & Co., Inc. was used; developing solvent: n-hexane-ethyl acetate (1:1)]

Mass analysis; [FAB-MS] m/z: 504 (M+H)$^+$

Nuclear magnetic resonance spectrum;

$^1$H-NMR(δ ppm,400 MHz, CDCl$_3$):5.13(2H,s),5.03(1H, t,J=8.8 Hz),4.70(1H,s),4.57(1H,brs),4.37(1H,dq,J=11.2 Hz,6.4 Hz),4.21(1H,s),3.16–3.05(5H,m),2.25–2.17(2H,m), 2.07–1.90(4H,m),1.81(1H,brd,J=12.7 Hz),1.69(2H,m),1.63 (3H,s),1.50(2H,q,J=14.6 Hz,7.3 Hz),1.45(3H,d,J=6.4 Hz), 1.36(1H,q,J=12.7 Hz),1.18(1H,dd,J=11.7 Hz,8.3 Hz),1.06 (1H,t,J=12.2 Hz),0.97 (3H,s),0.9–0.89(9H,m)

Example 34

Preparation of 1,13a-dihydroxy-11-isopropyl-4,7,8a-trimethyl-13-methylene-2-oxo-1,2,4,4a,5,7a,8,8a,9,10,11,11a,12,12a,13,13a-hexadecahydroindeno[5',6':4,5]cycloocta [1,2-c]pyran-10-yl N-butylcarbamate [Compound (35)]

Compound (2) (30 mg) was dissolved in 2.0 ml of dry toluene, and 9.7 μl of butyl isocyanate and 50 μl of dibutyltin diacetate were added, and the mixture was stirred at room temperature. For making the reaction progress, 2.5 hours later, 9.7 μl of butyl isocyanate was added, and the mixture was stirred for further 2.5 hours. The reaction mixture was concentrated under reduced pressure, and the concentrate was charged onto silica gel column (Kieselgel 60 made by Merck & Co., Inc., 1.5ϕ×25 cm) and developed with n-hexane-ethyl acetate (2:1). Fractions containing the objective substance were concentrated under reduced pressure to obtain 28.0 mg of Compound (35).

Rf value; 0.44 [Kieselgel 60$F_{254}$ made by Merck & Co., Inc. was used; developing solvent: n-hexane-ethyl acetate (1:1)]

Mass analysis; [FAB-MS] m/z: 518 (M+H)$^+$

Nuclear magnetic resonance spectrum;

$^1$H-NMR(δ ppm,400 MHz, CDCl$_3$): 5.14(1H,d,J=1.0 Hz), 5.14(1H,brs),5.03(1H,t,J=9.3 Hz),4.70(1H,s),4.56(1H,brs), 4.38(1H,dq,J=10.7 Hz,6.4 Hz),4.22(1H,s),3.16–3.05(5H,m), 2.2–22.16(2H,m),2.0–1.90(4H,m),1.82(1H,brd,J=12.7 Hz), 1.68(2H,m),1.62(3H,s),1.50–1.43(2H,m),1.45(3H,d,J=6.4 Hz),1.40–1.29(3H,m),1.18(1H,dd,J=11.7 Hz,8.3 Hz),1.06 (1H,t,J=12.2 Hz),0.96(3H,s),0.93–0.90(9H,m)

Example 35

Preparation of 1,13a-dihydroxy-11-isopropyl-4,7,8a-trimethyl-13-methylene-2-oxo-1,2,4,4a,5,7a,8,8a,9,10,11,11a,12,12a,13,13a-hexadecahydroindeno[5',6':4,5]cycloocta [1,2-c]pyran-10-yl N-pentylcarbamate [Compound (36)]

Compound (2) (30 mg) was dissolved in 2.0 ml of dry toluene, and 13.9 μl of pentyl isocyanate and 50 μl of dibutyltin diacetate were added, and the mixture was stirred at room temperature. For making the reaction progress, 2 hours later, 13.9 μl of pentyl isocyanate was added, and the mixture was stirred for further 16 hours. The reaction mixture was concentrated under reduced pressure, and the concentrate was charged onto silica gel column (Kieselgel 60 made by Merck & Co., Inc., 1.5φ×25 cm) and developed with n-hexane-ethyl acetate (3:1) and then (2:1). Fractions containing the objective substance were concentrated under reduced pressure to obtain 26.5 mg of Compound (36).

Rf value; 0.39 [Kieselgel 60F$_{254}$ made by Merck & Co., Inc. was used; developing solvent: n-hexane-ethyl acetate (2:1)]

Mass analysis; [FAB-MS] m/z: 532 (M+H)$^+$

Nuclear magnetic resonance spectrum;

$^1$H-NMR(δ ppm,400MHz, CDCl$_3$): 5.14(2H,s),5.03(1H,t,J=8.8 Hz),4.70(1H,s),4.55(1H,t,J=5.4 Hz),4.38(1H,dq,J=11.2 Hz,6.4 Hz),4.21(1H,s),3.16–3.05(5H,m),2.88(1H,brs), 2.24–2.16(2H,m),2.06–1.90(4H,m),1.81(1H,brd,J=12.7 Hz),1.69(2H,t,J=5.4 Hz),1.62(3H,s),1.48(1H,m),1.45(3H,d,J=6.4 Hz),1.37(1H,t,J=12.7 Hz),1.36–1.24(5H,m),1.18(1H,dd,J=11.7 Hz,8.3 Hz),1.06(1H,t,J=12.7 Hz),0.97(3H,s), 0.93–0.86(9H,m)

Example 36

Preparation of 1,13a-dihydroxy-11-isopropyl-4,7,8a-trimethyl-13-methylene-2-oxo-1,2,4,4a,5,7a,8,8a,9, 10,11,11a,12,12a,13,13a-hexadecahydroindeno[5', 6':4,5]cycloocta [1,2-c]pyran-10-yl N-octylcarbamate [Compound (37)]

Compound (2) (30 mg) was dissolved in 0.7 ml of dry toluene, and 15.1 μl of octyl isocyanate and 38 μl of dibutyltin diacetate were added, and the mixture was stirred at room temperature for 2 hours. The reaction mixture was concentrated under reduced pressure, and the concentrate was charged onto silica gel column (Kieselgel 60 made by Merck & Co., Inc., 1.5φ×23 cm) and developed with n-hexane-ethyl acetate (3:1). Fractions containing the objective substance were concentrated under reduced pressure to obtain 28.9 mg of Compound (37).

Rf value; 0.55 [Kieselgel 60F$_{254}$ made by Merck & Co., Inc. was used; developing solvent: n-hexane-ethyl acetate (1:1)]

Mass analysis; [FAB-MS] m/z: 574 (M+H)$^+$

Nuclear magnetic resonance spectrum;

$^1$H-NMR(δ ppm,400 MHz, CDCl$_3$): 5.14(2H,s),5.03(1H,t,J=8.8 Hz),4.70(1H,s),4.55(1H,brs),4.38(1H,dq,J=10.7 Hz,6.4 Hz),4.22(1H,s),3.16–3.05(6H,m),2.24–2.17(2H,m), 2.04(1H,dd,J=10.7 Hz,3.4 Hz),1.98–1.90(3H,m),1.81(1H, brd,J=12.7 Hz),1.69(2H,m),1.63(3H,s),1.49(2H,m),1.46 (3H,d,J=6.4 Hz),1.36(1H,q,J=12.7 Hz),1.31–1.27(10H,m), 1.18(1H,dd,J=11.7 Hz,8.3 Hz),1.06(1H,t,J=12.2 Hz),0.97 (3H,s),0.93(3H,d,J=5.4 Hz),0.92(3H,d,J=6.4 Hz),0.88(3H,t, J=6.8 Hz)

Example 37

Preparation of 1,13a-dihydroxy-11-isopropyl-4,7,8-atrimethyl-13 -methylene-2-oxo-1,2,4,4a,5,7a,8,8a, 9,10,11,11a,12,12a,13,13a-hexadecahydroindeno[5', 6':4,5]cycloocta [1,2-c]pyran-10-yl N-isopropylcarbamate [Compound (38)]

Compound (2) (30 mg) was dissolved in 2.0. ml of dry toluene, and 8.5 μl of isopropyl isocyanate and 50 μl of dibutyltin diacetate were added, and the mixture was stirred at room temperature. For making the reaction progress, 2 hours later and 3.5 hours later, 8.5 μl portions of butyl isocyanate were added, respectively, and the mixture was stirred for further 1.5 hours. The reaction mixture was concentrated under reduced pressure, and the concentrate was charged onto silica gel column (Kieselgel 60 made by Merck & Co., Inc., 1.5φ×25 cm) and developed with n-hexane-ethyl acetate (3:2). Fractions containing the objective substance were concentrated under reduced pressure to obtain 25.0 mg of Compound (38).

Rf value; 0.41 [Kieselgel 60F$_{254}$ made by Merck & Co., Inc. was used; developing solvent: n-hexane-ethyl acetate (1:1)]

Mass analysis; [FAB-MS] m/z: 504 (M+H)$^+$

Nuclear magnetic resonance spectrum;

$^1$H-NMR(δ ppm,400 MHz, CDCl$_3$): 5.14(1H,d,J=1.5 Hz), 5.14(1H,brs),5.03(1H,t,J=8.3 Hz),4.70(1H,s),4.41–4.34(2H, m),4.21(1H,d,J=3.9 Hz),3.78(1H,m),3.17(1H,d,J=3.9 Hz), 3.13–3.04(1H,m),2.88(1H,brs),2.25–2.16(1H,m),2.08–1.90 (1H,m),1.81(1H,dt,J=12.7 Hz,3.4 Hz),1.69(2H,brm),1.63 (3H,s),1.45(3H,d,J=6.4 Hz),1.36(1H,q,J=12.7 Hz),1.18(1H, dd,J=12.2 Hz,8.8 Hz),1.14(6H,d,J=6.8 Hz),1.06(1H,t,J=12.7 Hz),0.96(3H,s),0.93(3H,d,J=6.3 Hz),0.92(3H,d,J=6.3 Hz)

Example 38

Preparation of 1,13a-dihydroxy-11-isopropyl-4,7,8 a-trimethyl-13-methylene-2-oxo-1,2,4,4a,5,7a,8,8a, 9,10,11,11a,12,12a,13,13a-hexadecahydroindeno[5', 6':4,5]cycloocta [1,2-c]pyran-10-yl N-(4-fluorophenyl)carbamate [Compound (39)]

Compound (2) (30 mg) was dissolved in 2.0 ml of dry toluene, and 11.9 μl of p-fluorophenyl isocyanate and 50 μl of dibutyltin diacetate were added, and the mixture was stirred at room temperature. For making the reaction progress, 2 hours later, 11.9 μl of p-fluorophenyl isocyanate was added, and the mixture was stirred for further 16 hours. The reaction mixture was concentrated under reduced pressure, and the concentrate was charged onto silica gel column (Kieselgel 60 made by Merck & Co., Inc., 1.5φ×25 cm) and developed with n-hexane-ethyl acetate (3:2). Fractions containing the objective substance were concentrated under reduced pressure to obtain 29.5 mg of Compound (39).

Rf value; 0.29 [Kieselgel 60F$_{254}$ made by Merck & Co., Inc. was used; developing solvent: n-hexane-ethyl acetate (1:1)]

Mass analysis; [FAB-MS] m/z: 556 (M+H)$^+$

Nuclear magnetic resonance spectrum;

$^1$H-NMR(δ ppm,400 MHz, CDCl$_3$): 7.34(2H,m),7.00(2H, t,J=8.8 Hz),6.50(1H,brs),5.25(1H,dt,J=7.8 Hz,3.4 Hz),5.15 (1H,d,J=1.0 Hz),5.04(1H,t,J=8.3 Hz),4.71(1H,s),4.39(1H, dq,J=10.8 Hz,6.4 Hz),4.22(1H,s),3.16–3.07(3H,m),2.85(1H, s),2.28(1H,dd,J=11.7 Hz,7.3 Hz),2.23(1H,td,J=12.7 Hz,3.4 Hz),2.07–1.92 (4H,m),1.83(1H,dt,J=12.7 Hz,2.9 Hz), 1.77–1.72(2H,m),1.64(3H,s),1.46(3H,d,J=6.4 Hz),1.38(1H, q,J=12.7 Hz),1.25(1H,dd,J=11.7 Hz,8.8 Hz),1.08(1H,t,J=12.7 Hz),0.99(3H,s),0.95(6H,d,J=5.9 Hz)

Example 39

Preparation of 1,13a-dihydroxy-11-isopropyl-4,7,8a-trimethyl-13-methylene-2-oxo-1,2,4,4a,5,7a,8,8a,9, 10,11,11a,12,12a,13,13a-hexadecahydroindeno[5', 6':4,5]cycloocta [1,2-c]pyran-10-yl N-benzylcarbamate [Compound (40)]

Compound (2) (30 mg) was dissolved in 2.0 ml of dry toluene, and 13.3 μl of benzyl isocyanate and 50 μl of dibutyltin diacetate were added, and the mixture was stirred at room temperature for 21 hours. The reaction mixture was concentrated under reduced pressure, and the concentrate was charged onto silica gel column (Kieselgel 60 made by Merck & Co., Inc., 1.5φ×25 cm) and developed with n-hexane-ethyl acetate (2:1). Fractions containing the objective substance were concentrated under reduced pressure to obtain 20.2 mg of Compound (40).

Rf value; 0.30 [Kieselgel 60F$_{254}$ made by Merck & Co., Inc. was used; developing solvent: n-hexane-ethyl acetate (1:1)]

Mass analysis; [FAB-MS] m/z: 552 (M+H)$^+$

Nuclear magnetic resonance spectrum;

$^1$H-NMR(δ ppm,400 MHz, CDCl$_3$): 7.35–7.32(2H,m), 7.31–7.26(3H,m),5.19(1H,brdt,J=6.8 Hz,2.4 Hz),5.14(1H,d, J=1.0 Hz),5.03(1H,t,J=8.3 Hz),4.91(1H,brs),4.70(1H,s), 4.41–4.29(3H,m),4.21(1H,d,J=3.4 Hz),3.17(1H,d,J=3.4 Hz),3.13–3.05(2H,m),2.89(1H,s),2.25(1H,dd,J=12.2 Hz,6.8 Hz),2.20(1H,td,J=12.7 Hz,3.4 Hz),2.07–1.90(4H,m),1.81 (1H,dt,J=12.7 Hz,3.4 Hz),1.70(2H,m),1.63(3H,s),1.45(3H, d,J=6.3 Hz),1.36(1H,q,J=12.7 Hz),1.23(1H,brs),1.06(1H,t, J=12.7 Hz),0.97(3H,s),0.93(6H,brs)

Example 40

Preparation of 1,13a-dihydroxy-11-isopropyl-4,7,8a-trimethyl-13-methylene-2-oxo-1,2,4,4a,5,7a,8,8a,9, 10,11,11a,12,12a,13,13a-hexadecahydroindeno[5', 6':4,5]cycloocta [1,2-c]pyran-10-yl N-allylcarbamate [Compound (41)]

Compound (2) (30 mg) was dissolved in 2.0 ml of dry toluene, and 7.6 μl of allyl isocyanate and 50 μl of dibutyltin diacetate were added, and the mixture was stirred at room temperature. For making the reaction progress, 2 hours later, 7.6 μl of allyl isocyanate was added, and the mixture was stirred for further 3 hours. The reaction mixture was concentrated under reduced pressure, and the concentrate was charged onto silica gel column (Kieselgel 60 made by Merck & Co., Inc., 1.5φ×25 cm) and developed with n-hexane-ethyl acetate (2:1). Fractions containing the objective substance were concentrated under reduced pressure to obtain 24.5 mg of Compound (41).

Rf value; 0.30 [Kieselgel 60F$_{254}$ made by Merck & Co., Inc. was used; developing solvent: n-hexane-ethyl acetate (1:1)]

Mass analysis; [FAB-MS] m/z: 502 (M+H)$^+$

Nuclear magnetic resonance spectrum;

$^1$H-NMR(δ ppm,400 MHz, CDCl$_3$): 5.84(1H,m), 5.19–5.09(3H,m),5.13(1H,d,J=1.0 Hz),5.03(1H,t,J=8.8 Hz), 4.70(1H,s),4.67(1H,brs),4.37(1H,dq,J=11.2 Hz,6.3 Hz),4.21 (1H,d,J=3.9 Hz),3.78(2H,brs),3.26(1H,dd,J=4.4 Hz,2.0 Hz), 3.15–3.05(2H,m),2.96(1H,brs),2.25–2.16(2H,m),2.06–1.90 (4H,m),1.82(1H,dt,J=12.7 Hz,3.4 Hz),1.69(2H,m),1.62(3H, s),1.45(3H,d,J=6.4 Hz),1.35(1H,q,J=12.7 Hz),1.19(1H,dd, J=11.7 Hz,8.3 Hz),1.06(1H,t,J=12.7 Hz),0.96(3H,s),0.92 (3H,d,J=5.9 Hz),0.91(3H,d,J=5.9 Hz)

Example 41

Preparation of 1,13a-dihydroxy-11-isopropyl-4,7,8a-trimethyl-13-methylene-2-oxo-1,2,4,4a,5,7a,8,8a,9, 10,11,11a,12,12a,13,13a-hexadecahydroindeno[5', 6':4,5]cycloocta [1,2-c]pyran-10-yl N-tetrahydro-2H-pyran-2-ylcarbamate [Compound (42)]

Compound (2) (30 mg) was dissolved in 2.0 ml of dry toluene, and 12.6 μl of tetrahydropyran-2-yl isocyanate and 50 μl of dibutyltin diacetate were added, and the mixture was stirred at room temperature. For making the reaction progress, 2 hours later, 12.6 μl of tetrahydropyran-2-yl isocyanate was added, band the mixture was stirred for further 3 hours. The reaction mixture was concentrated under reduced pressure, and the concentrate was charged onto silica gel column (Kieselgel 60 made by Merck & Co., Inc., 1.5φ×25 cm) and developed with n-hexane-ethyl acetate (2:1) and then (1:1). Fractions containing the objective substance were concentrated under reduced pressure to obtain 25.2 mg of Compound (42).

Rf value; 0.22 [Kieselgel 60F$_{254}$ made by Merck & Co., Inc. was used; developing solvent: n-hexane-ethyl acetate (1:1)]

Mass analysis; [FAB-MS] m/z: 546 (M+H)$^+$

Nuclear magnetic resonance spectrum;

$^1$H-NMR(δ ppm,400 MHz, CDCl$_3$): 5.18–5.13(3H,m), 5.03(1H,t,J=8.8 Hz),4.84(1H,m),4.70(1H,s),4.37(1H,dq,J= 10.7 Hz,6.3 Hz),4.21(1H,s),3.97(1H,m),3.57(1H,m), 3.15–3.04(2H,m),2.26–2.16(2H,m),2.06–1.92(4H,m), 1.90–1.78(3H,m),1.69(3H,m),1.62(3H,s),1.50(2H,m),1.45 (3H,d,J=6.3 Hz),1.40–1.34(2H,m),1.21(1H,dd,J=12.2 Hz,8.3 Hz),1.05(1H,t,J=12.2 Hz),0.96(3H,s),0.92–0.90(6H, m)

Example 42

Preparation of 1,13a-dihydroxy-11-isopropyl-4,7,8a-trimethyl-13-methylene-2-oxo-1,2,4,4a,5,7a,8,8a,9, 11a,12,12a,13,13a-hexadecahydroindeno[5',6':4,5] cycloocta [1,2-c]pyran-10-yl N-phenylcarbamate [Compound (43)]

Compound (2) (30 mg) was dissolved in 0.7 ml of dry toluene, and 9.2 μl of phenyl isocyanate and 38 μl of dibutyltin diacetate were added, and the mixture was stirred at room temperature for 22 hours. The reaction mixture was concentrated under reduced pressure, and the concentrate was charged onto silica gel column (Kieselgel 60 made by Merck & Co., Inc., 1.5φ×25 cm) and developed with n-hexane-ethyl acetate (2:1). Fractions containing the objective substance were concentrated under reduced pressure to obtain 19.2 mg of Compound (43).

Rf value; 0.46 [Kieselgel 60F$_{254}$ made by Merck & Co., Inc. was used; developing solvent: n-hexane-ethyl acetate (1:1)]

Mass analysis; [FAB-MS] m/z: 538 (M+H)$^+$

Nuclear magnetic resonance spectrum;

$^1$H-NMR(δ ppm,400 MHz, CDCl$_3$): 7.38(2H,d,J=7.3 Hz), 7.30(2H,t,J=7.3 Hz),7.05(1H,t,J=7.3 Hz),6.54(1H,s),5.26 (1H,td,J=7.8 Hz,3.4 Hz),5.15(1H,d,J=1.5 Hz),5.04(1H,t,J= 8.3 Hz),4.71(1H,s),4.39(1H,dq,J=11.2 Hz,6.4 Hz),4.22(1H, s),3.17–3.07(3H,m),2.86(1H,brs),2.29(1H,dd,J=12.2 Hz,7.3 Hz),2.21(1H,td,11.2 Hz,2.4 Hz),2.09–1.91(4H,m),1.84(1H, dt,J=12.7 Hz,3.4 Hz),1.80–1.67(2H,m),1.63(3H,s),1.46(3H, d,J=6.4 Hz),1.38(1H,q,J=12.7 Hz),1.26(1H,dd,J=12.2 Hz,8.3 Hz),1.09(1H,t,J=123.2 Hz),1.00(3H,s),0.95(6H,d,J= 5.9 Hz)

Example 43

Preparation of 10-({[(ethoxycarbonyl)amino] carbonyl}oxy)- 1,13a-dihydroxy-11-isopropyl-4,7, 8a-trimethyl-13-methylene -2-oxo-1,2,4,4a,5,7a,8, 8a,9,10,11,11a,12,12a,13,13a-hexadecahydroindeno [5',6':4,5]cycloocta[1,2-c]pyran [Compound (44)]

Compound (2) (30 mg) was dissolved in 0.7 ml of dry toluene, and 10.0 μl of ethyl isocyanate formate and 38 μl of dibutyltin diacetate were added, and the mixture was stirred at room temperature. For making the reaction progress, 3 hours later, 10.0 µl of ethyl isocyanate formate was added, and the mixture was stirred for further 15 hours. The reaction mixture was concentrated under reduced pressure, and the concentrate was charged onto silica gel column (Kieselgel 60 made by Merck & Co., Inc., 1.5φ×25 cm) and developed successively with n-hexane-ethyl acetate (2:1→1:2). Fractions containing the objective substance were concentrated under reduced pressure to obtain a crude product. This was subjected to high performance liquid chromatography (Chromatorex ODS made by FUJI SILYSIA CHEMICAL LTD., 2.0 cmφ×25 cm) and eluted with 60% acetonitrile, and fractions containing the objective substance were concentrated under reduced pressure to obtain 11.0 mg of Compound (44).

Rf value; 0.47 [Kieselgel 60F$_{254}$ made by Merck & Co., Inc. was used; developing solvent: n-hexane-ethyl acetate (1:2)]

Mass analysis; [FAB-MS] m/z: 534 (M+H)$^+$

Nuclear magnetic resonance spectrum;

$^1$H-NMR(δ ppm,400 MHz, CDCl$_3$): 6.93(1H,s),5.24(1H, td,J=7.8 Hz,3.4 Hz),5.14(1H,d,J=1.0 Hz),5.04(1H,t,J=8.8 Hz),4.71(1H,s),4.38(1H,dq,J=11.2 Hz,5.9 Hz),4.23(3H,m), 3.15–3.06(3H,m),2.85(1H,s),2.28(1H,dd,J=11.7 Hz,7.3 Hz), 2.20(1H,m),2.09–1.91(4H,m),1.82(1H,dt,J=13.2 Hz,3.4 Hz),1.78–1.67(2H,m), 1.63(3H,s),1.46(3H,d,J=5.9 Hz),1.36 (1H,q,J=13.2 Hz),1.30(3H,t,J=7.3 Hz),1.23(1H,dd,J=11.7 Hz,8.3 Hz),1.07(1H,t,J=12.2 Hz),0.97(3H,s),0.93(3H,d,J= 6.3 Hz),0.91(3H,d,J=5.9 Hz)

Example 44

Preparation of 1,13a-dihydroxy-11-isopropyl-4,7,8a-trimethyl-13-methylene-2-oxo-1,2,4,4a,5,7a,8,8a,9, 10,11,11a,12,12a,13,13a-hexadecahydroindeno[5', 6':4,5]cycloocta [1,2-c]pyran-10-yl N-t-butylcarbamate [Compound (45)]

Compound (2) (30 mg) was dissolved in 0.7 ml of dry toluene, and 9.7 µl of t-butyl isocyanate and 38 µl of dibutyltin diacetate were added, and the mixture was stirred at room temperature. For making the reaction progress, 2 hours later, 7.6 µl of t-butyl isocyanate was added, and the mixture was stirred for further 2 hours. The reaction mixture was concentrated under reduced pressure, and the concentrate was charged onto silica gel column (Kieselgel 60 made by Merck & Co., Inc., 1.5φ×25 cm) and developed with n-hexane-ethyl acetate (2:1). Fractions containing the objective substance were concentrated under reduced pressure to obtain 15.4 mg of Compound (45).

Rf value; 0.54 [Kieselgel 60F$_{254}$ made by Merck & Co., Inc. was used; developing solvent: n-hexane-ethyl acetate (1:1)]

Mass analysis; [FAB-MS] m/z: 518 (M+H)$^+$

Nuclear magnetic resonance spectrum;

$^1$H-NMR(δ ppm,400 MHz, CDCl$_3$): 5.14(1H,d,J=1.0 Hz), 5.12(1H,brs),5.03(1H,t,J=8.8 Hz),4.70(1H,s),4.55(1H,s), 4.38(1H,dq,J=10.7 Hz,6.4 Hz),4.21(1H,s),3.16–3.05(3H,m), 2.87(1H,brs),2.24–2.17(2H,m),2.04(1H,dd,J=10.7 Hz,7.8 Hz), 1.98–1.90(3H,m),1.81(1H,brd,J=12.7 Hz),1.68(2H,m), 1.62(3H,s),1.45(3H,d,J=6.4 Hz),1.36(1H,q,J=12.7 Hz),1.30 (9H,s),1.17(1H,dd,J=12.2 Hz,8.8 Hz),1.06(1H,t,J=12.2 Hz), 0.96(3H,s),0.92(3H,d,J=5.4 Hz),0.91(3H,d,J=5.9 Hz)

Example 45

Preparation of 1,13a-dihydroxy-11-isopropyl-4,7,8a-trimethyl-13-methylene-2-oxo-1,2,4,4a,5,7a,8,8a,9, 10,11,11a,12,12a,13,13a-hexadecahydroindeno[5', 6':4,5]cycloocta [1,2-c]pyran-10-yl N-cyclohexylcarbamate [Compound (46)]

Compound (2) (30 mg) was dissolved in 0.7 ml of dry toluene, and 10.8 µl of cyclohexyl isocyanate and 38 µl of dibutyltin diacetate were added, and the mixture was stirred at room temperature. For making the reaction progress, 2 hours later, 11 µl of cyclohexyl isocyanate was added, and the mixture was stirred for further 2 hours. The reaction mixture was concentrated under reduced pressure, and the concentrate was charged onto silica gel column (Kieselgel 60 made by Merck & Co., Inc., 1.5φ×24 cm) and developed successively with n-hexane-ethyl acetate (4:1→2:1). Fractions containing the objective substance were concentrated under reduced pressure to obtain 21.0 mg of Compound (46).

Rf value; 0.50 [Kieselgel 60F$_{254}$ made by Merck & Co., Inc. was used; developing solvent: n-hexane-ethyl acetate (1:1)]

Mass analysis; [FAB-MS] m/z: 544 (M+H)$^+$

Nuclear magnetic resonance spectrum;

$^1$H-NMR(δ ppm,400 MHz, CDCl$_3$): 5.14(2H,s),5.03(1H, t,J=9.3 Hz),4.70(1H,s),4.47(1H,d,J=7.8 Hz),4.38(1H,dq,J= 10.7 Hz,6.3 Hz),4.22(1H,s),3.46(1H,m),3.25(1H,m),3.10 (2H,m),2.93(1H,brs),2.19(2H,m),2.04(1H,dd,J=10.7 Hz, 7.3 Hz),1.94(6H,m),1.81(1H,m),1.71–1.58(4H,m),1.62(3H,s), 1.45(3H,d,J=6.3 Hz),1.40–1.25(4H,m),1.21–1.03(6H,m), 0.96(3H,s),0.92(3H,d,J=5.4 Hz),0.91(3H,d,J=6.4 Hz)

Example 46

Preparation of 1,13a-dihydroxy-11-isopropyl-4,7,8a-trimethyl-13-methylene-2-oxo-1,2,4,4a,5,7a,8,8a,9, 10,11,11a,12,12a,13,13a-hexadecahydroindeno[5', 6':4,5]cycloocta [1,2-c]pyran-10-yl N-benzoylcarbamate [Compound (47)]

Compound (2) (30 mg) was dissolved in 0.7 ml of dry toluene, and 10.8 µl of benzoyl isocyanate and 38 µl of dibutyltin diacetate were added, and the mixture was stirred at room temperature for 17 hours. The reaction mixture was concentrated under reduced pressure, and the concentrate was charged onto silica gel column (Kieselgel 60 made by Merck & Co., Inc., 1.5φ×23 cm) and developed with n-hexane-ethyl acetate (1:1). Fractions containing the objective substance were concentrated under reduced pressure to obtain 10.7 mg of Compound (47).

Rf value; 0.50 [Kieselgel 60F$_{254}$ made by Merck & Co., Inc. was used; developing solvent: n-hexane-ethyl acetate (1:3)]

Mass analysis; [FAB-MS] m/z: 566 (M+H)$^+$

Nuclear magnetic resonance spectrum;

$^1$H-NMR(δ ppm,400 MHz, CDCl$_3$): 8.05(1H,s),7.82(2H, dd,J=7.3 Hz,1.5 Hz),7.59(1H,t,J=7.8 Hz),7.48(2H,dd,J=7.8 Hz,7.3 Hz),5.31(1H,td,7.8 Hz,3.9 Hz),5.14(1H,s),5.04(1H, t,J=8.8 Hz),4.71(1H,s),4.38(1H,dq,J=10.3 Hz,6.3 Hz),4.23 (1H,s),3.16–3.07(2H,m),2.32(1H,dd,J=12.2 Hz,7.3 Hz),2.20 (1H,t,J=12.2 Hz),2.07–1.91(4H,m),1.85–1.70(3H,m),1.63 (3H,s),1.46(3H,d,J=6.3 Hz),1.37(1H,q,J=12.7 Hz),1.28(1H, dd,J=12.2 Hz,7.8 Hz),1.08(1H,t,12.2 Hz),0.99(3H,s),0.95 (6H,d,J=9 Hz)

Example 47

Preparation of 10-{[(ethylamino)carbothioyl]oxy}-1,13a-dihydroxy-11-isopropyl-4,7,8a-trimethyl-13-methylene-2-oxo-1,2,4,4a,5,7a,8,8a,9,10,11,11a,12, 12a,13,13a-hexadecahydroindeno[5',6':4,5]cycloocta [1,2-c]pyran [Compound (48)]

Compound (2) (30 mg) was dissolved in 0.7 ml of dry toluene, and 7.5 µl of ethyl isocyanate and 38 µl of dibutyltin diacetate were added, and the mixture was stirred at room temperature. For making the reaction progress, 2 hours later, the reaction temperature was made to be 60° C. and the mixture was stirred for further 22 hours. The reaction mixture was concentrated under reduced pressure, and the concentrate was charged onto silica gel column (Kieselgel 60 made by Merck & Co., Inc., 1.5φ×23 cm) and developed with n-hexane-ethyl acetate (2:1). Fractions containing the objective substance were concentrated under reduced pressure to obtain 2.4 mg of a crude product.

This was subjected to high performance liquid chromatography (Chromatorex ODS made by FUJI SILYSIA CHEMICAL LTD., 2.0φ×25 cm) and eluted with 80% acetonitrile, and fractions containing the objective substance were concentrated under reduced pressure to obtain 1.0 mg of Compound (48).

Rf value; 0.44 [Kieselgel 60F$_{254}$ made by Merck & Co., Inc. was used; developing solvent: n-hexane-ethyl acetate (1:1)]

Mass analysis; [FAB-MS] m/z: 506 (M+H)$^+$

Nuclear magnetic resonance spectrum;

$^1$H-NMR(δ ppm,400 MHz, CDCl$_3$): 6.07(1H,brs),5.75 (1H,td,J=7.8 Hz,3.9 Hz),5.15(1H,s),5.04(1H,t,J=8.8 Hz), 4.71(1H,s),4.39(1H,dq,J=11.2 Hz,6.4 Hz),4.22(1H,s),3.56 (2H,m),3.15–3.05(3H,m),2.82(1H,brs),2.42(1H,dd,J=11.7 Hz,7.3 Hz),2.21(1H,brs),2.10–1.87(4H,m),1.86–1.66(3H, m),1.63(3H,s),1.46(3H,d,J=6.4 Hz),1.43–1.34(1H,m), 1.25–1.20(4H,m),1.06(1H,t,J=11.7 Hz),1.01(3H,s),0.93(3H, d,J=5.9 Hz),0.92(3H,d,J=6.4 Hz)

Example 48

Preparation of 1,13a-dihydroxy-10-[(3-hydroxy-3,5-dimethylheptyl)oxy]-11-isopropyl-4,7,8a-trimethyl-13-methylene-2-oxo-4,4a,5,7a,8,8a,9,10,11,11a,12, 12a,13,13a-tetradecahydroindeno[5',6':4,5]cycloocta [1,2-c]pyran-2(1H)-one [Compound (50)]

(Step 1)

Compound (1) (1 g) was dissolved in 7.4 ml of diethyl ether, and the solution was added dropwise at 0° C. to a solution of 198 mg of lithium aluminum hydride in 10 ml of diethyl ether. For making the reaction further progress, the temperature was raised to room temperature, and 198 mg of lithium aluminum hydride was added. After 12 hours, the reaction mixture was poured in cold water, and the mixture was made to pH 3 with 1N hydrochloric acid and extracted with ethyl acetate. The ethyl acetate layer was washed with water and saturated brine, dried over anhydrous sodium sulfate, and concentrated under reduced pressure. The concentrate was charged onto silica gel column (Kieselgel 60 made by Merck & Co., Inc., 2.4φ×33 cm), and developed successively with n-hexane-ethyl acetate (4:1→2:1→3:2). Fractions containing the objective alcohol were concentrated under reduced pressure to obtain 229.1 mg of a side chain alcohol. This alcohol (77.4 mg) was dissolved in 2.4 ml of dry chloroform, 83 μl of 2,6-lutidine and 88 μl of trifluoromethanesulfonic anhydride were successively added, and reaction was carried out at 0° C. for 10 minutes to obtain a side chain triflate (49).

(Step 2)

Compound (2) (25 mg) was dissolved in 1.2 ml of dry dichloromethane, and 800 μl of the side chain triflate (49) was added dropwise at 0° C., and reaction was carried out for 1 hour and then at room temperature for 4 hours. The reaction mixture was charged onto silica gel column (Kieselgel 60 made by Merck & Co., Inc., 1.5φ×24 cm), and developed successively with n-hexane-ethyl acetate (4:1→3:1→2:1). Fractions containing the objective substance were concentrated under reduced pressure to obtain 1.9 mg of Compound (50).

Mass analysis; [FAB-MS] m/z: 561 (M+H)$^+$

Nuclear magnetic resonance spectrum;

$^1$H-NMR(δ ppm,400 MHz, CDCl$_3$): 5.13(1H,s),5.03(1H, brs),4.69(1H,s),4.38(1H,dq,J=11.2 Hz,6.4 Hz),4.21(1H,s), 3.94(1H,m),3.65(1H,m),3.57(1H,m),3.51(1H,s),3.16–3.04 (3H,m),2.79(1H,s),2.56(1H,s),2.18(1H,td,J=12.2 Hz,2.9 Hz),2.10–2.02(2H,m),2.00–1.90(3H,m),1.88–1.77(3H,m), 1.69–1.48(3H,m),1.63(3H,s),1.46(d,J=6.4 Hz),1.43–1.22 (4H,m),1.26(3H,d,J=1.5 Hz),1.21(3H,s),1.18(1H,dd,J=13.2 Hz,7.3 Hz),1.08(1H,t,J=12.2 Hz),0.96(3H,d,J=6.8 Hz),0.95 (3H,d,J=6.8 Hz),0.93(3H,d,J=5.9 Hz),0.87(3H,t,7.3 Hz)

Example 49

Preparation of N-(1,13a-dihydroxy-11-isopropyl-4, 7,8a-trimethyl-13-methylene-2-oxo-1,2,4,4a,5,7a,8, 8a,9,10,11,11a,12,12a,13,13a-hexadecahydroindeno [5',6':4,5]cycloocta [1,2-c]pyran-10-yl)-N'-butylurea [Compound (53)]

(Step 1)

Preparation of 10-iodo-13a-hydroxy-11-isopropyl-4, 7,8a-trimethyl-13-methylene-1-(tetrahydro-2H-pyran-2-yloxy) -4,4a,5,7a,8,8a,9,10,11,11a,12,12a, 13,13a-hexadecahydroindeno[5',6':4,5]cycloocta[1, 2-c]pyran-2(1H)-one [Compound (51)]

Compound (4) (30 mg) was dissolved in 2.0 ml of dry toluene, and 31.3 mg of triphenylphosphine and 18.8 μl of diethyl azodicarboxylate were added and finally 7.4 μl of methyl iodide was added, and the mixture was stirred at room temperature for 2 hours. The reaction mixture was charged as such onto silica gel column (Kieselgel 60 made by Merck & Co., Inc., 1.5φ×25 cm), and developed with n-hexane-ethyl acetate (3:1). Fractions containing the objective substance were concentrated under reduced pressure, the residue was dissolved in 0.1 ml of ethyl acetate, 0.3 ml of n-hexane was added, and the mixture was allowed to stand for 30 minutes to deposit crystals. The crystals were filtered to obtain 17.2 mg of Compound (51).

Rf value; 0.51 [Kieselgel 60F$_{254}$ made by Merck & Co., Inc. was used; developing solvent: n-hexane-ethyl acetate (2:1)]

Mass analysis; [FAB-MS] m/z: 613 (M+H)$^+$

Nuclear magnetic resonance spectrum;

$^1$H-NMR(δ ppm, 400 MHz, CDCl$_3$): 5.11(1H,s),5.02(1H, t,J=9.3 Hz),4.79–4.74(2H,m),4.65(1H,dd,J=7.4 Hz,2.5 Hz), 4.35–4.31(2H,m),4.16(1H,s),4.00(1H,d,J=11.2 Hz),3.55 (1H,m),3.09(1H,dd,J=14.2 Hz,9.3 Hz),2.94(1H,t,J=10.3), 2.46(1H,dd,J=14.7 Hz,2.9 Hz),2.26–2.15 (2H,m),2.04–1.85 (6H,m),1.76(1H,t,J=9.8 Hz),1.68–1.61(4H,m),1.56–1.49 (6H,m),1.42(3H,d,J=6.4 Hz),1.23(3H,s),1.07(3H,d,J=6.8 Hz),1.04(3H,d,J=5.9 Hz),0.90(1H,t,J=12.2 Hz)

(Step 2)

Preparation of 10-azido-13a-hydroxy-11-isopropyl-4,7,8a-trimethyl-13-methylene-1-(tetrahydro-2H-pyran-2-yloxy) -4,4a,5,7a,8,8a,9,10,11,11a,12,12a, 13,13a-hexadecahydroindeno[5',6':4,5]cycloocta[1, 2-c]pyran-2(1H)-one [Compound (52)]

Compound (51) (15 mg) was dissolved in 1.0 ml of dry dimethylformamide, 4.3 mg of sodium azide was added, and the mixture was stirred at room temperature. For making the reaction progress, 3 hours later, 4.3 mg of sodium azide and 50 μl of 15-crown-5-ether were added, and the mixture was stirred for further 15 hours. The reaction mixture was added into 50 ml of ethyl acetate, and the mixture was washed three times with 50 ml portions of water. The ethyl acetate layer was concentrated, and the concentrate was charged onto silica gel column (Kieselgel 60 made by Merck & Co., Inc., 1.5φ×25 cm), and developed with n-hexane-ethyl acetate (3:1). Fractions containing the objective substance were concentrated under reduced pressure to obtain 5.7 mg of Compound (52).

Rf value; 0.55 [Kieselgel 60$F_{254}$ made by Merck & Co., Inc. was used; developing solvent: n-hexane-ethyl acetate (2:1)]

Mass analysis; [FAB-MS] m/z: 528 (M+H)$^+$

Nuclear magnetic resonance spectrum;

$^1$H-NMR(δ ppm,400 MHz, CDCl$_3$): 5.10(1H,s),5.04(1H, t,J=8.8 Hz),4.76(1H,s),4.64(1H,dd,J=7.3 Hz,2.9 Hz),4.45 (1H,m),4.33(1H,dq,J=10.8 Hz,6.4 Hz),4.15(1H,s),4.00(1H, dt,J=11.2 Hz,4.4 Hz),3.79(1H,td,J=7.3 Hz,4.4 Hz),3.54(1H, td,J=11.2 Hz,2.9 Hz),3.16–3.04(2H,m),2.19(1H,td,J=12.7 Hz,2.9 Hz),2.02–1.83(8H,m),1.72–1.66(2H,m),1.62(3H,s), 1.61–1.46(4H,m),1.42(3H,d,J=6.4 Hz),1.34–1.24(2H,m), 1.07(1H,t,J=12.7 Hz),0.97(3H,d,J=5.9 Hz),0.96(3H,d,J=5.9 Hz),0.95(3H,s)

(Step 3) Preparation of Compound (53)

Compound (52) (70 mg) was dissolved in a mixed solvent of 1.0 ml of tetrahydrofuran and 0.1 ml of water, 69.7 mg of triphenylphosphine was added, and the mixture was refluxed for 4 hours. The reaction mixture was added to 50 ml of methanol, and the mixture was washed with 100 ml of hexane. The resulting methanol layer was concentrated to obtain 118 mg of a crudely purified product.

The crudely purified product (28 mg) was dissolved in 1.0 ml of dry toluene, and 7.6 μl of butyl isocyanate was added, and the mixture was stirred at room temperature for 1 hour. After the reaction, 1.0 ml of methanol and 19.3 mg of p-toluenesulfonic acid hydrate was added to the reaction mixture, and the mixture was stirred at room temperature for 1 hour. Then, the reaction mixture was concentrated, and the concentrate was charged onto silica gel column (Kieselgel 60 made by Merck & Co., Inc., 1.5φ×25 cm), and developed with chloroform-methanol (20:1). Fractions containing the objective substance were concentrated under reduced pressure to obtain 10.3 mg of Compound (53).

Rf value; 0.34 [Kieselgel 60$F_{254}$ made by Merck & Co., Inc. was used; developing solvent: chloroform-methanol (10:1)]

Mass analysis; [FAB-MS] m/z: 517 (M+H)$^+$

Nuclear magnetic resonance spectrum;

$^1$H-NMR(δ ppm,400 MHz, CDCl$_3$): 5.14(1H,d,J=1.0 Hz), 5.03(1H,t,J=8.8 Hz),4.70(1H,s),4.38(1H,dq,J=11.2 Hz,6.4 Hz),4.23–4.11(4H,m),3.24(1H,brs),3.16–3.03(4H,m),2.91 (1H,brs),2.20(1H,td,J=12.7 Hz,2.9 Hz),2.13(1H,dd,J=11.7 Hz,7.3 Hz),2.04(1H,dd,J=10.7 Hz,7.3 Hz),1.98–1.90(3H, m),1.80(1H,dt,J=12.7 Hz,2.9 Hz),1.72(1H,m),1.63(3H,s), 1.51–1.45(5H,m),1.44–1.30(4H,m),1.08–1.03(2H,m),0.98 (3H,s),0.96–0.90(9H,m)

Example 50

Preparation of N'-(1,13a-dihydroxy-11-isopropyl-4, 7,8a-trimethyl-13-methylene-2-oxo-1,2,4,4a,5,7a,8, 8a,9,10,11,11a,12,12a,13,13a-hexadecahydroindeno [5',6':4,5]cycloocta [1,2-c]pyran-10-yl)-3-hydroxy-3, 5-dimethylheptanamide [Compound (54)]

Compound (52) (70 mg) was dissolved in a mixed solvent of 1.0 ml of tetrahydrofuran and 0.1 ml of water, 69.7 mg of triphenylphosphine was added, and the mixture was refluxed for 4 hours. The reaction mixture was added to 50 ml of methanol, and the mixture was washed with 100 ml of hexane. The resulting methanol layer was concentrated to obtain 118 mg of a crudely purified product.

The crudely purified product (28 mg) was dissolved in 1.0 ml of dry dichloromethane, and 14.0 mg of dicyclohexylcarbodiimide, 8.3 mg of dimethylaminopyridine and 10.9 mg of 3-hydroxy-3,5-dimethylheptanoic acid were added, and the mixture was stirred at room temperature for 2 hours. After the reaction, 1.0 ml of methanol and 32.1 mg of p-toluenesulfonic acid hydrate were added to the reaction mixture, and the mixture was stirred at room temperature for 2 hours. Then, the reaction mixture was concentrated, and the concentrate was charged onto silica gel column (Kieselgel 60 made by Merck & Co., Inc., 1.5φ×25 cm), and developed with chloroform-methanol (20:1). Fractions containing the objective substance were concentrated under reduced pressure to obtain 6.0 mg of Compound (54).

Rf value; 0.47 [Kieselgel 60$F_{254}$ made by Merck & Co., Inc. was used; developing solvent: chloroform-methanol (10:1)]

Mass analysis; [FAB-MS] m/z: 574 (M+H)$^+$

Nuclear magnetic resonance spectrum;

$^1$H-NMR(δ ppm,400 MHz, CDCl$_3$): 5.84(1H,d,J=8.3 Hz), 5.14(1H,d,J=1.0 Hz),5.03(1H,t,J=8.8 Hz),4.71(1H,s), 4.44–4.34(2H,m),4.23(1H,brs),4.21(1H,s),3.14–3.02(2H, m),2.91(1H,brs),2.32(1H,d,J=14.7 Hz),2.22–2.13(3H,m), 2.04(1H,dd,J=10.7 Hz,7.3 Hz),1.99–1.88(3H,m),1.82(1H, dt,J=12.7 Hz,2.9 Hz),1.73(1H,m),1.63(3H,s),1.57–1.50(2H, m),1.46(3H,d,J=6.4 Hz),1.43–1.24(4H,m),1.22(3H,s),1.18 (1H,m),1.05–0.99(2H,m),0.99(3H,s),0.95–0.92(9H,m),0.86 (3H,t,J=7.3 Hz)

Example 51

Preparation of (E)-N$^1$-(1,13a-dihydroxy-11-isopropyl-4,7,8a-trimethyl-13-methylene-2-oxo-1,2, 4,4a,5,7a,8,8a,9,10,11,11a,12,12a,13,13a-hexadecahydroindeno[5',6':4,5]cycloocta [1,2-c] pyran-10-yl)-2-butenamide [Compound (61)]

(Step 1)

Preparation of 1,13a-dihydroxy-11-isopropyl-4,7,8a-trimethyl-13-methylene-4a,5,7a,8,8a,9,11,11a,12, 12a, 13,13a-dodecahydroindeno[5',6':4,5]cycloocta [1,2-c]pyrane-2,10(1H,4H)-dione [Compound (55)]

Compound (1) (1377 mg) was dissolved in 16.3 ml of dimethylformamide, a 1 molar solution of pyridinium dichromate in dimethylformamide was added under ice cooling over a period of 3 hours and 45 minutes. Then, the mixture was portioned with diethyl ether and water, and the ether layer was washed with 0.1 molar hydrochloric acid and then water, and dried over anhydrous magnesium sulfate. Then, the solution was concentrated under reduced pressure, and the concentrate was charged onto silica gel column (Kieselgel 60 made by Merck & Co., Inc., 2.9φ×25 cm), and eluted with hexane-ethyl acetate (1:1). Fractions containing the objective substance were concentrated to obtain 333 mg of Compound (55).

Rf value; 0.53 [Kieselgel 60$F_{254}$ made by Merck & Co., Inc. was used; developing solvent: chloroform-methanol (10:1)]

Mass analysis; [FAB-MS] m/z: 417 (M+H)$^+$
(Step 2)

Preparation of 1-{[1-(t-butyl)-1,1dimethylsilyl]oxy}-13a-hydroxy-11-isopropyl-4,7,8a-trimethyl-1-methylene-4a,5, 7a,8,8a,9,11,11a,12,12a,13,13a-dodecahydroindeno [5',6':4,5]cycloocta[1,2-c]pyrane-2,10(1H,4H)-dione [Compound (56)]

Compound (55) (600 mg) was dissolved in 14.4 ml of anhydrous chloroform, and 670 μl of 2,6-lutidine and 670 μl of t-butyldimethylsilyl trifluoromethanesulfonate were added, and reaction was allowed to progress under ice cooling for 1 hour. The reaction mixture was concentrated under reduced pressure, and the concentrate was charged onto silica gel column (Kieselgel 60 made by Merck & Co., Inc., 2.4φ×24 cm), and eluted with hexane-ethyl acetate (3:1). Fractions containing the objective substance were concentrated to obtain 698 mg of Compound (56).

Rf value; 0.64 [Kieselgel 60F$_{254}$ made by Merck & Co., Inc. was used; developing solvent: chloroform-methanol (10:1)]

Mass analysis; [FAB-MS] m/z: 531 (M+H)$^+$
(Step 3)

Preparation of 1-{[1-(t-butyl)-1,1dimethylsilyl]oxy}-10,13a-dihydroxy-11-isopropyl-4,7,8a-trimethyl-13-methylene-4,4a,5,7a,8,8a,9,10,11,11a,12,12a,13,13a-tetradecahydroindeno[5',6':4,5]cycloocta[1,2-c]pyran-2(1H)-one [Compound (57)]

Compound (56) (250 mg) was dissolved in 9.4 ml of anhydrous tetrahydrofuran, and 480 mg of lithium tributoxyaluminum hydride was added under ice cooling and a nitrogen atmosphere, and reaction was allowed to progress under ice cooling. For making the reaction further progress, 1 hour later and 2 hours later, 480 mg portions were added, respectively, and the mixture was allowed to react at room temperature for 3 hours, and then the reaction was ceased. The reaction mixture was portioned with ethyl acetate and 0.5 molar phosphate buffer (pH 7.0), and the ethyl acetate layer was dried over anhydrous sodium sulfate. The resulting reaction mixture was concentrated under reduced pressure, and the concentrate was charged onto silica gel column (Kieselgel 60 made by Merck & Co., Inc., 2.4φ×23 cm), and eluted with hexane-diisopropyl ether (3:1→2:1). Fractions containing the objective substance were concentrated to obtain 88 mg of Compound (57).

Rf value; 0.57 [Kieselgel 60F$_{254}$ made by Merck & Co., Inc. was used; developing solvent: hexane-diisopropyl ether (1:2)]

Mass analysis; [FAB-MS] m/z: 533 (M+H)$^+$
(Step 4)

Preparation of 10-azido-1-{[1-(t-butyl)-1,1-dimethylsilyl-]oxy}-13a-hydroxy-11-isopropyl-4,7,8a-trimethyl-13-methylene-4,4a,5,7a,8,8a,9,10,11,11a,12,12a,13,13a-tetradecahydroindeno[5',6':4,5]cycloocta[1,2-c]pyran-2(1H)-one [Compound (58)]

Compound (57) (88 mg) was dissolved in 3.5 ml of anhydrous toluene, and 88 mg of triphenylphosphine and 53 μl of diethyl azodicarboxylate were added under ice cooling. The mixture was allowed to react for 50 minutes under a nitrogen atmosphere with the light being blocked off, 70 μl of diphenylphosphoryl azide was added, and the mixture was allowed to react at room temperature for 2 hours. The reaction mixture was charged onto silica gel column (Kieselgel 60 made by Merck & Co., Inc., 1.5φ×48 cm), and eluted with hexane-ethyl acetate (20:1). Fractions containing the objective substance were concentrated to obtain 49.8 mg of Compound (58).

Rf value; 0.54 [Kieselgel 60F$_{254}$ made by Merck & Co., Inc. was used; developing solvent: chloroform-methanol (10:1)]

Mass analysis; [FAB-MS] m/z: 558 (M+H)$^+$
(Step 5)

Preparation of 10-amino-1-{[1-(t-butyl)-1,1-dimethylsilyl]oxy}-13a-hydroxy-11-isopropyl-4,7,8a-trimethyl-13methylene-4,4a,5,7a,8,8a,9,10,11,11a,12,12a,13,13a-tetradecahydroindeno[5',6':4,5]cycloocta[1,2-c]pyran-2(1H)-one [Compound (59)]

Compound (58) (49 mg) was dissolved in 5 ml of tetrahydrofuran and 0.5 ml of water, and 46 mg of triphenylphosphine was added, and the mixture was allowed to react at 70° C. for 18 hours. The reaction mixture was concentrated under reduced pressure, and the concentrate was charged onto Sephadex LH20 column (made by Pharmacia Co., 1.5φ×45 cm), and eluted with methanol. Fractions containing the objective substance were concentrated to obtain 54 mg of Compound (59).

Rf value; 0.48 [Kieselgel 60F$_{254}$ made by Merck & Co., Inc. was used; developing solvent: chloroform-methanol (5:1)]

Mass analysis; [FAB-MS] m/z: 532 (M+H)$^+$
(Step 6)

Preparation of (E)-N$^1$-(1-{[-1-(t-butyl)-1,1-dimethylsilyl]-oxy}-13a-hydroxy-11-isopropyl-4,7,8a-trimethyl-13-methylene-2-oxo-1,2,4,4a,5,7a,8,8a,9,10,11,11a,12,12a,13,13a-hexadecahydroindeno[5',6':4,5]cycloocta[1,2-c]pyran-10-yl)-2-butenamide [Compound (60)]

Compound (59) (10 mg) was dissolved in 0.2 ml of anhydrous dichloromethane, and 4.5 mg of dimethylaminopyridine and 2.9 μl of crotonic anhydride were added, and the mixture was allowed to react at room temperature for 1 hour. The reaction mixture was charged onto silica gel column (Kieselgel 60 made by Merck & Co., Inc., 1.5φ×24 cm), and eluted with hexane-ethyl acetate (3:1). Fractions containing the objective substance were concentrated to obtain 5.7 mg of Compound (60).

Rf value; 0.52 [Kieselgel 60F$_{254}$ made by Merck & Co., Inc. was used; developing solvent: hexane-ethyl acetate (1:1)]

Mass analysis; [FAB-MS] m/z: 600 (M+H)$^+$
(Step 7)Preparation of Compound (61)

Compound (60) (5.6 mg) was dissolved in 0.5 ml of tetrahydrofuran, and 20 μl of 1.0 M tetrabutylammonium fluoride-tetrahydrofuran solution was added, and the mixture was stirred at room temperature for 1 hour. The reaction mixture was charged onto silica gel column (Kieselgel 60 made by Merck & Co., Inc., 1.5φ×24 cm), and eluted with hexane-ethyl acetate (1:2). Fractions containing the objective substance were concentrated to obtain 4.0 mg of Compound (61).

Rf value; 0.13 [Kieselgel 60F$_{254}$ made by Merck & Co., Inc. was used; developing solvent: hexane-ethyl acetate (1:1)]

Mass analysis; [FAB-MS] m/z: 486 (M+H)$^+$
Nuclear magnetic resonance spectrum;
$^1$H-NMR(δ ppm,400 MHz, CDCl$_3$): 6.81(1H,dq,J=15.1 Hz,6.8 Hz),5.73(1H,dd,J=15.1 Hz,2.0 Hz),5.35(1H,d,J=8.8

Hz),5.15(1H,d,J=1.0 Hz),5.03(1H,t,J=8.3 Hz),4.71(1H,s),
4.46–4.34(2H,m),4.21(1H,s),3.15–3.04(2H,m),2.85(1H,
brs),2.24–2.14(2H,m),2.06–1.91(4H,m),1.84(3H,dd,J=6.8
Hz,2.0 Hz),1.80–1.71(3H,m),1.63(3H,s),1.46(3H,d,J=5.9
Hz),1.41–1.27(2H,m),1.04(1H,m),1.00(3H,s),0.92(6H,d,J=6.4 Hz)

Example 52

Preparation of $N^3$-(1,13a-dihydroxy-11-isopropyl-4, 7,8a-trimethyl-13-methylene-2-oxo-1,2,4,4a,5,7a,8, 8a,9,10,11,11a,12,12a,13,13a-hexadecahydroindeno [5',6':4,5]cycloocta-[1,2-c]pyran-10-yl)-2-chloronicotinamide [Compound (63)]

(Step 1)

Preparation of $N^3$-(1-{[1-(t-butyl)-1,1-dimethylsilyl] oxy}-13a-hydroxy-11-isopropyl-4,7,8a-trimethyl-13-methylene-2-oxo-1,2,4,4a,5,7a,8,8a,9,10,11,11a,12, 12a,13,13a-hexadecahydroindeno[5',6':4,5]cycloocta [1,2-c]pyran-10-yl)-2-chloronicotinamide [Compound (62)]

Compound (59) (10 mg) was dissolved in 0.2 ml of anhydrous dichloromethane, and 4.5 mg of dimethylaminopyridine, 7.7 mg of dicyclohexylcarbodiimide and 5.9 mg of 2-chloronicotinic acid were added, and the mixture was allowed to react at room temperature for 2 hours and a half. The reaction mixture was charged onto silica gel column (Kieselgel 60 made by Merck & Co., Inc., 1.5ϕ×23 cm), and eluted successively with hexane-ethyl acetate (6:1→3:1→1:1). Fractions containing the objective substance were concentrated to obtain 4.6 mg of (62).

Rf value; 0.28 [Kieselgel $60F_{254}$ made by Merck & Co., Inc. was used; developing solvent: hexane-ethyl acetate (1:1)]

Mass analysis; [FAB-MS] m/z: 671 (M+H)$^+$ (Step 2) Preparation of Compound (63)

Compound (62) (4.6 mg) was dissolved in 0.37 ml of tetrahydrofuran, and 11 μl of 1.0 M tetrabutylammonium fluoride-tetrahydrofuran solution was added, and the mixture was stirred at room temperature for 30 minutes. The reaction mixture was charged onto silica gel column (Kieselgel 60 made by Merck & Co., Inc., 1.5ϕ×23 cm), and eluted with hexane-ethyl acetate (1:2). Fractions containing the objective substance were concentrated to obtain 2.5 mg of Compound (63).

Rf value; 0.60 [Kieselgel $60F_{254}$ made by Merck & Co., Inc. was used; developing solvent: ethyl acetate]

Mass analysis; [FAB-MS] m/z: 557 (M+H)$^+$

Nuclear magnetic resonance spectrum;

$^1$H-NMR(δ ppm,400 MHz,CDCl$_3$): 8.46(1H,dd,J=4.9 Hz,2.0 Hz),8.08(1H,dd,J=7.3 Hz,2.0 Hz),7.34(1H,dd,J=7.3 Hz,4.9 Hz),6.42(1H,d,J=8.3 Hz),5.16(1h,d,J=1.5 Hz),5.05 (1H,t,J=8.3 Hz),4.72(1H,s),4.59(1H,dt,J=14.2 Hz,8.3 Hz), 4.39(1H,dq,J=11.2 Hz,6.4 Hz),4.22(1H,s),3.15–3.05(3H,m), 2.85(1H,brs),2.30–2.20(2H,m),2.07–1.91(4H,m),1.87–1.67 (3H,m),1.64(3H,s),1.46(3H,d,J=6.4 Hz),1.40(1H,q,J=12.7 Hz),1.30–1.07(2H,m),1.05(3H,s),1.00(3H,d,J=6.4 Hz),0.97 (3H,d,J=6.4 Hz)

Example 53

Preparation of N'-(1,13a-dihydroxy-11-isopropyl-4, 7,8a-trimethyl-13-methylene-2-oxo-1,2,4,4a,5,7a,8, 8a,9,10,11,11a,12,12a,13,13a-hexadecahydroindeno [5',6':4,5]cycloocta[1,2-c]pyran-10-yl)-3-benzo[b] thienylacetamide [Compound (64)]

Compound (52) (330 mg) was dissolved in a mixed solvent of 3.0 ml of tetrahydrofuran and 0.15 ml of water, and 327 mg of triphenylphosphine was added, and the mixture was refluxed for 4 hours. The reaction mixture was added to 100 ml of methanol, and the mixture was washed with 200 ml of hexane. The resulting methanol layer was concentrated to obtain 520 mg of a crudely purified product.

The crudely purified product (35 mg) was dissolved in 1.0 ml of dry dichloromethane, and 28.7 mg of 1-ethyl-3-(3-dimethylaminopropyl)-carbodiimide hydrochloride, 13.7 mg of dimethylaminopyridine and 21.5 mg of benzo[b] thiophene-3-acetic acid were added, and the mixture was stirred at room temperature for 24 hours. After the reaction, 1.0 ml of a hydrochloric acid-methanol solution was added, and the mixture was stirred at room temperature for 1 hour. The reaction mixture was concentrated and added to 50 ml of ethyl acetate, and the mixture was washed with 50 ml of water. The resulting ethyl acetate layer was concentrated, and the concentrate was charged onto silica gel column (Kieselgel 60 made by Merck & Co., Inc., 1.5ϕ×25 cm), and developed with hexane-ethyl acetate (1:1). Fractions containing the objective substance were concentrated under reduced pressure to obtain 3.3 mg of Compound (64).

Rf value; 0.31 [Kieselgel $60F_{254}$ made by Merck & Co., Inc. was used; developing solvent: chloroform-methanol; 20:1]

Mass analysis; [FAB-MS] m/z: 592 (M+H)$^+$

Nuclear magnetic resonance spectrum;

$^1$H-NMR(δ ppm,400 MHz,CDCl$_3$): 7.89(1H,m),7.71(1H, m),7.41(2H,m),7.32(1H,s),5.32(1H,brd,J=8.8 Hz),5.10(1H, brs),5.00(1H,t,J=9.3 Hz),4.67(1H,brs),4.33(2H,m),4.17(1H, d,J=3.9 Hz),3.79(2H,s),3.05–2.90(3H,m),2.72(1H,brs), 2.20–1.80(5H,m),1.80–1.60(4H,m),1.60(3H,s),1.43(3H,d, J=6.4 Hz),1.28(1H,m),1.09(1H,m),0.94(3H,s),0.84(1H,m), 0.79 (6H,d,J=6.4 Hz)

Example 54

Preparation of N'-(1,13a-dihydroxy-11-isopropyl-4, 7,8a-trimethyl-13-methylene-2-oxo-1,2,4,4a,5,7a,8, 8a,9,10,11,11a,12,12a,13,13a-hexadecahydroindeno [5',6':4,5]cycloocta[1,2-c]pyran-10-yl)-4-chlorophenylacetamide [Compound (65)]

Compound (52) (330 mg) was dissolved in a mixed solvent of 3.0 ml of tetrahydrofuran and 0.15 ml of water, and 327 mg of triphenylphosphine was added, and the mixture was refluxed for 4 hours. The reaction mixture was added to 100 ml of methanol, and the mixture was washed with 200 ml of hexane. The resulting methanol layer was concentrated to obtain 520 mg of a crudely purified product.

The crudely purified product (32 mg) was dissolved in 1.0 ml of dry dichloromethane, and 23 mg of 1-ethyl-3-(3-dimethylaminopropyl)-carbodiimide hydrochloride, 14.6 mg of dimethylaminopyridine and 20.5 mg of p-chlorophenylacetic acid were added, and the mixture was stirred at room temperature for 1 hours. After the reaction, 1.0 ml of methanol and 1.0 ml of a hydrochloric acid-methanol solution were added, and the mixture was stirred at room temperature for 1 hour. The reaction mixture was concentrated and added to 50 ml of ethyl acetate, and the mixture was washed with 50 ml of water. The resulting ethyl acetate layer was concentrated, and the concentrate was charged onto silica gel column (Kieselgel 60 made by Merck & Co., Inc., 1.5ϕ×25 cm), and developed with chloroform-methanol (30:1). Fractions containing the objective substance were concentrated to obtain 12.3 mg of Compound (65).

Rf value; 0.41 [Kieselgel $60F_{254}$ made by Merck & Co., Inc. was used; developing solvent: chloroform-methanol; 20:1]

Mass analysis; [FAB-MS] m/z: 570 (M+H)$^+$

Nuclear magnetic resonance spectrum;

$^1$H-NMR(δ ppm,400 MHz,CDCl$_3$): 7.33(2H,d,J=8.3 Hz), 7.17(2H,d,J=8.3 Hz),5.24(1H,brd,J=8.3 Hz),5.12(1H,d,J= 1.5 Hz),5.02(1H,t,J=9.3 Hz),4.69(1H,brs),4.34(2H,m),4.19 (1H,d,J=4.0 Hz),3.48(2H,s),3.15–2.98(3H,m),2.79(1H,brs), 2.22–1.80(6H,m),1.80–1.60(3H,m),1.59(3H,s),1.45(3H,d, J=6.4 Hz),1.40–1.20(2H,m),0.99(1H,m),0.97(3H,s),0.87 (3H,d,J=6.4 Hz),0.85(3H,t,J=6.4 Hz)

Specific examples of pharmaceutical preparations are shown below citing instances, but the invention should not be limited to these pharmaceutical preparation examples.

Pharmaceutical Preparation Example 1

Compound 10 (10 parts), 15 parts of heavy magnesium oxide and 75 parts of lactose are uniformly mixed to make powdery or finely granular powder having a diameter of 350 μm or less. This powder is encapsulated to make capsules.

Pharmaceutical Preparation Example 2

Compound 10 (45 parts), 15 parts of starch, 16 parts of lactose, 21 parts of crystalline cellulose, 3 parts of polyvinyl alcohol and 30 parts of distilled water are uniformly mixed, pulverized, granulated, dried, and then sieved to make granules having a diameter of 1,410 to 177 μm.

Pharmaceutical Preparation Example 3

Granules are made in the same manner as in Pharmaceutical preparation example 2, 3 parts of calcium stearate is added to 96 parts of these granules, and the mixture is compression molded into tablets having a diameter of 10 mm.

Pharmaceutical Preparation Example

Crystalline cellulose (10 parts) and 3 parts of calcium stearate are added to 90 parts of granules obtained by the process of Pharmaceutical preparation example 2, and the mixture is compression molded into tablets having a diameter of 8 mm, and a mixed suspension of syrup gelatin and precipitated calcium carbonate is added thereto to prepare sugar-coated tablets.

Pharmaceutical Preparation Example 5

Compound 10 (1 part), 49.5 parts of macrogol 4,000 and 49.5 parts of macrogol 400 are mixed and sufficiently kneaded to make a wholly homogeneous ointment.

Pharmaceutical Preparation Example 6

Compound 10 (0.3 part), 2.4 parts of a nonionic surfactant and 97 parts of physiological saline are mixed at an elevated temperature and put into ampoules, and sterilized to prepare an injection.

Reference Example 1

Preparation of BE-49385s 1-1) Preparation of fractions containing BE-49385A and BE-49385B A fungus F49385 strain inoculated on a slant soft agar medium was inoculated into 100 ml of a medium containing 1.0% glucose, 3.0% maltose, 0.3% malt extract, 1.0% wheat germ, 0.5% gluten meal, 0.3% polypeptone, 0.1% sodium nitrate, 0.2% sodium chloride, 0.1% dipotassium hydrogenphosphate, 0.05% magnesium sulfate, 0.00008% zinc sulfate, 0.002% calcium chloride, 0.0002% ferrous sulfate, 0.00004% cuprous chloride, 0.00004% manganese chloride, 0.00004% cobalt chloride, 0.00008% sodium borate and 0.00024% ammonium molybdate (pH 6) in each of six 500-ml conical flasks, and cultured at 28° C. for 96 hours on a rotary shaker (180 turnovers per minute). Two hundred ml of the culture broths were inoculated into 10 L of the above medium in each of three 20-L jar fermenters and cultured at 28° C. for 312 hours.

The resulting culture broths (26.5 L) were sterilized at 90° C. for 10 minutes, the cells were separated by filtration, methanol (20 L) was added to the cells, the mixture was stirred for several hours, and the cells were filtered off to obtain a methanol extract. Acetone (10 L) was added to the cells after the methanol extraction, the mixture was stirred for several hours, and the cells were filtered off to obtain an acetone extract. The methanol extract and the acetone extract were combined together and concentrated up to about 2 L under reduced pressure. To the concentrate were added n-hexane (1 L) and ethyl acetate (1 L) for extraction. The resulting n-hexane/ethyl acetate extract was concentrated under reduced pressure, n-hexane (500 ml) was added to the residue, the mixture was filtered, the filtrate was charged on a silica gel (made by Wako Pure Chemical Industries, Ltd.) column (4.0φ×25 cm) for chromatography, and eluted with n-hexane and a mixed solvent of n-hexane/ ethyl acetate (8:1→1:1). The eluted active fractions were concentrated to dryness under reduced pressure to obtain 1,526 mg of a fraction containing BE-49385A and BE-49385B.

1-1-1) Preparation of a crude product containing BE-49385A

The fraction obtained in 1-1) was dissolved in methanol (5 ml), the solution was charged on a Sephadex LH-20 (made by Pharmacia Co.) column (4.0φ×45 cm) for chromatography, and eluted with 80% methanol. The resulting objective fractions were concentrated under reduced pressure, the concentrate was dissolved in ethanol (3 ml), the solution was charged on a Sephadex LH-20 (made by Pharmacia Co.) column (4.0φ×45 cm) for chromatography, and eluted with ethanol, the eluted active fractions were concentrated under reduced pressure, the concentrate was dissolved in ethanol (6 ml), 0.2 ml portions of the solution were charged onto Develosil ODS-10 columns (made by Nomura Kagaku Co., Ltd., 20φ×50 mm), respectively, and subjected to preparative high performance liquid chromatography using 85% acetonitrile as a mobile phase to obtain 508 mg of a crude substance fraction 2-1 containing BE-49385A.

1-1-1-1) Preparation of BE-49385A

The fraction 2-1 obtained in 1-1-1) was dissolved in toluene (10 ml), the solution was charged on a silica gel (made by Merck & Co., Inc.) column (2.5φ×33 cm) for chromatography, and eluted with a mixed solvent of toluene/ ethyl acetate (9:1→8:1). The objective fractions obtained by the elution were concentrated under reduced pressure. The concentrate was dissolved in ethanol (5 ml), and 0.3 ml portions of the solution were charged onto YMC Pack ODS-A columns (made by YMC Co., 20φ×250 mm), respectively, and subjected to preparative high performance liquid chromatography using 88% acetonitrile as a mobile phase. The objective fractions were concentrated under reduced pressure, water (50 ml) was added to the concentrate, and the mixture was acidified with 1 N hydrochloric acid, extracted with ethyl acetate (50 ml). The ethyl acetate extract was washed with water (50 ml) and concentrated to dryness to obtain 485 mg of white powder of BE-49385A.

INDUSTRIAL APPLICABILITY

The compounds or antifungal compositions of the invention show excellent antifungal activities on fungi against which existing antifungal agents do not sufficiently exert their effects, and thus are useful as antifungal agents.

What is claimed is:

1. A compound represented by the formula [I]

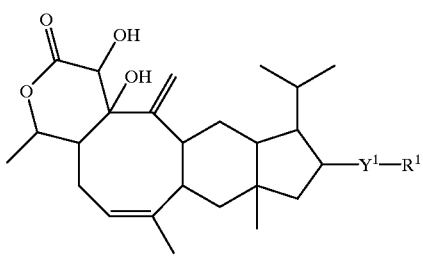

[I]

wherein $Y^1$ represents an oxygen atom, or a group represented by NH, O—CO, O—SO$_2$, O—CO—NH, O—CS—NH, NH—CO, NH—SO$_2$, NH—CO—NH or NH—CS—NH, $R^1$ represents, each unsubstituted, a $C_1$–$C_{16}$ alkyl group, a $C_2$–$C_{10}$ alkenyl group, a $C_3$–$C_6$ alkynyl group, a $C_6$–$C_{12}$ aryl group, a $C_7$–$C_{15}$ aralkyl group, a $C_9$–$C_{15}$ arylalkenyl group, a $C_9$–$C_{15}$ arylalkynyl group, a $C_3$–$C_6$ cycloalkyl group, a $C_3$–$C_6$ cycloalkyl $C_1$–$C_{16}$ alkyl group, a $C_1$–$C_{16}$ alkylcarbonyl group, a $C_1$–$C_{16}$ alkoxycarbonyl group, a $C_6$–$C_{12}$ arylcarbonyl group or a heterocyclic group; or a $C_1$–$C_{16}$ alkyl group, a $C_2$–$C_{10}$ alkenyl group, a $C_3$–$C_6$ alkynyl group, a $C_6$–$C_{12}$ aryl group, a $C_7$–$C_{15}$ aralkyl group, a $C_9$–$C_{15}$ arylalkenyl group, a $C_9$–$C_{15}$ arylalkynyl group, a $C_3$–$C_6$ cycloalkyl group, a $C_3$–$C_6$ cycloalkyl $C_1$–$C_{16}$ alkyl group, a $C_1$–$C_{16}$ alkylcarbonyl group, a $C_1$–$C_{16}$ alkoxycarbonyl group, a $C_6$–$C_{12}$ arylcarbonyl group or a heterocyclic group, each having 1 to 5 substituents selected from the group consisting of a halogen atom, a cyano group, a hydroxy group, a $C_1$–$C_{16}$ alkyl group (excluding the case where $R^1$ is a $C_1$–$C_5$ alkyl group), a $C_1$–$C_{16}$ alkoxy group, a $C_1$–$C_{16}$ alkylcarbonyloxy group, an amino group, a mono-$C_1$–$C_{16}$ alkylamino group, a di-$C_1$–$C_{16}$ alkylamino group, a carboxyl group, a $C_1$–$C_{16}$ alkoxycarbonyl group, an aminocarbonyl group, a sulfo group, a $C_6$–$C_{12}$ aryloxy group, a $C_7$–$C_{15}$ aralkyloxy group and a heterocyclic group;

with the proviso that when $Y^1$ represents O—CO, $R^1$ does not represent a 2,4-dimethylhexyl group, a 2-hydroxy-2,4-dimethylhexyl group, a 1,2-dihydroxy-2,4-dimethylhexyl group, a 1hydroxy-3,5-dimethylheptyl group, a 1,2-dihydroxy-5-methylheptyl group, a 1,2-dihydroxy-3,5-dimethylheptyl group or a 1hydroxy-1-phenylmethyl group, or a pharmacologically acceptable salt or ester thereof;

in the above, the heterocyclic group being an aromatic heterocyclic group or a nonaromatic heterocyclic group, and meaning a 5- to 7-membered monocyclic heterocyclic group containing 1 to 4 hetero atoms selected from the group consisting of a nitrogen atom, an oxygen atom and a sulfur atom, or a condensed ring-type heterocyclic group wherein the above monocyclic heterocyclic group is condensed with the above-mentioned $C_3$–$C_6$ cycloalkyl group, the above-mentioned $C_6$–$C_{12}$ aryl group or another monocyclic heterocyclic group which is the same or different and defined as above.

2. The compound according to claim 1 represented by the formula [I-2]

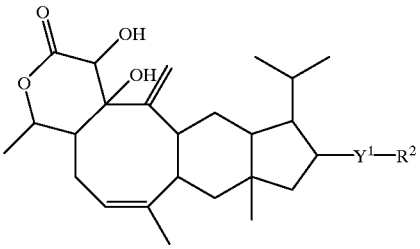

[I-2]

wherein $Y^1$ is as defined in claim 1

$R^2$ represents, each unsubstituted, a $C_1$–$C_5$ alkyl group, a $C_2$–$C_{10}$ alkenyl group, a $C_3$–$C_6$ alkynyl group, a $C_6$–$C_{12}$ aryl group, a $C_7$–$C_{15}$ aralkyl group, a $C_9$–$C_{15}$ arylalkenyl group, a $C_9$–$C_{15}$ arylalkynyl group, a $C_3$–$C_6$ cycloalkyl group, a $C_3$–$C_6$ cycloalkyl $C_1$–$C_{16}$ alkyl group, a $C_1$–$C_{16}$ alkylcarbonyl group, a $C_1$–$C_{16}$ alkoxycarbonyl group, a $C_6$–$C_{12}$ arylcarbonyl group or a heterocyclic group; or a $C_1$–$C_5$ alkyl group, a $C_2$–$C_{10}$ alkenyl group, a $C_3$–$C_6$ alkynyl group, a $C_6$–$C_{12}$ aryl group, a $C_7$–$C_{15}$ aralkyl group, a $C_9$–$C_{15}$ arylalkenyl group, a $C_9$–$C_{15}$ arylalkynyl group, a $C_3$–$C_6$ cycloalkyl group, a $C_3$–$C_6$ cycloalkyl $C_1$–$C_{16}$ alkyl group, a $C_1$–$C_{16}$ alkylcarbonyl group, a $C_1$–$C_{16}$ alkoxycarbonyl group, a $C_6$–$C_{12}$ arylcarbonyl group or a heterocyclic group, each having 1 to 5 substituents selected from the group consisting of a halogen atom, a cyano group, a hydroxy group, a $C_1$–$C_{16}$ alkyl group (excluding the case where $R^1$ is a $C_1$–$C_5$ alkyl group), a $C_1$–$C_{16}$ alkoxy group, a $C_1$–$C_{16}$ alkylcarbonyloxy group, an amino group, a mono-$C_1$–$C_{16}$ alkylamino group, a di-$C_1$–$C_{16}$ alkylamino group, a carboxyl group, a $C_1$–$C_{16}$ alkoxycarbonyl group, an aminocarbonyl group, a sulfo group, a $C_6$–$C_{12}$ aryloxy group, a $C_7$–$C_{15}$ aralkyloxy group and a heterocyclic group, or a pharmacologically acceptable salt or ester thereof.

3. The compound according to claim 2 wherein $R^2$ is unsubstituted or has 1 to 3 substituents, or a pharmacologically acceptable salt or ester thereof.

4. The compound according to claim 3 wherein $R^2$ is unsubstituted or has 1 or 2 substituents, or a pharmacologically acceptable salt or ester thereof.

5. The compound according to claim 2 represented by the formula [I-3]

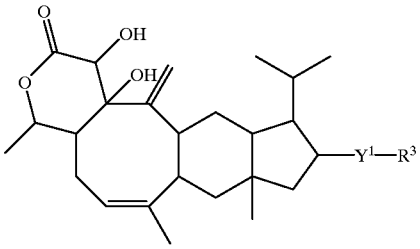

[I-3]

wherein $Y^1$ is as defined in claim 2

$R^3$ represents a group selected from the group consisting of, each unsubstituted, a $C_1$–$C_5$ alkyl group, a $C_2$–$C_{10}$ alkenyl group, a phenyl group, a phenyl $C_1$–$C_9$ alkyl group, a phenyl $C_3$–$C_5$ alkenyl group, a $C_3$–$C_6$ cycloalkyl, a $C_1$–$C_{16}$ alkylcarbonyl group, a $C_1$–$C_{16}$ alkoxycarbonyl group, a benzoyl group and a heterocyclic group; or a group selected from the group consisting of a $C_1$–$C_5$ alkyl group, a $C_2$–$C_{10}$ alkenyl group, a phenyl group, a phenyl $C_1$–$C_9$ alkyl group, a phenyl $C_3$–$C_5$ alkenyl group, a $C_3$–$C_6$ cycloalkyl, a $C_1$–$C_{16}$ alkylcarbonyl group, a $C_1$–$C_{16}$ alkoxycarbonyl group, a benzoyl group and a heterocyclic group, each having 1 or 2 substituents selected from the group consisting of a halogen atom, a cyano group, a $C_1$–$C_3$ alkoxy group and a $C_1$–$C_3$ alkyl group (excluding the case where $R^3$ is a $C_1$–$C_5$ alkyl group), or a pharmacologically acceptable salt or ester thereof.

6. The compound according to claim 5 wherein the heterocyclic group is selected from the group consisting of a pyridyl group, a quinolyl group, a tetrahydropyranyl group, a tetrahydrofuranyl group, a benzothienyl group, a benzofuryl group and an indolyl group, or a pharmacologically acceptable salt or ester thereof.

7. The compound according to claim 2 represented by the formula [I-4]

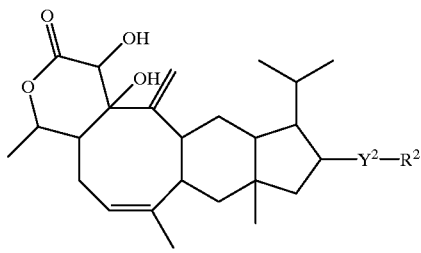

[I-4]

wherein $R^2$ is as defined in claim 2, and $Y^2$ represents an oxygen atom, O—CO, O—SO$_2$, O—CO—NH, O—CS—NH or NH—CO,
or a pharmacologically acceptable salt or ester thereof.

8. The compound according to claim 5 represented by the formula [I-5]

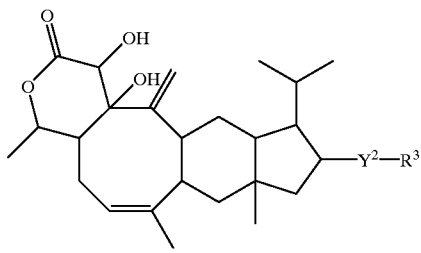

[I-5]

wherein $Y^2$ and $R^3$ are as defined in claim 7 and claim 5, respectively,
or a pharmacologically acceptable salt or ester thereof.

9. The compound according to claim 7 represented by the formula [I-6]

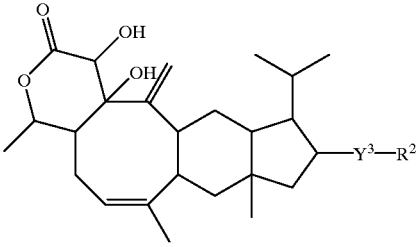

[I-6]

wherein $R^2$ is as defined in claim 7, and $Y^3$ represents O—CO, O—CO—NH or NH—CO,
or a pharmacologically acceptable salt or ester thereof.

10. The compound according to claim 8 represented by the formula [I-7]

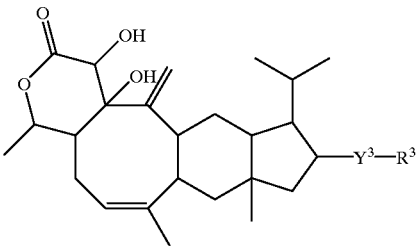

[I-7]

wherein $Y^3$ and $R^3$ are as defined in claim 9 and claim 8, respectively,
or a pharmacologically acceptable salt or ester thereof.

11. An antifungal agent containing as an effective ingredient a compound represented by the formula [I]

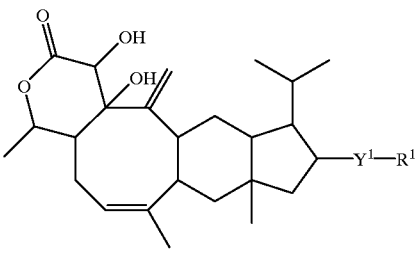

[I]

wherein $Y^1$ and $R^1$ are as defined in claim 1,
or a pharmacologically acceptable salt or ester thereof.

* * * * *